US007384635B2

(12) United States Patent
Holm et al.

(10) Patent No.: US 7,384,635 B2
(45) Date of Patent: Jun. 10, 2008

(54) PROTEIN VARIANTS OF NATURALLY OCCURRING ALLERGENS

(75) Inventors: Jens Holm, Copenhagen N (DK); Jorgen N. Larsen, Graested (DK)

(73) Assignee: Alk-Abello A/S, Horsholm (DK)

( * ) Notice: Subject to any disclaimer, the term of this patent is extended or adjusted under 35 U.S.C. 154(b) by 401 days.

(21) Appl. No.: 10/698,855

(22) Filed: Oct. 31, 2003

(65) Prior Publication Data

US 2004/0171116 A1    Sep. 2, 2004

Related U.S. Application Data

(60) Provisional application No. 60/422,983, filed on Nov. 1, 2002.

(30) Foreign Application Priority Data

Nov. 1, 2002    (DK) ............................... 2002 01686

(51) Int. Cl.
*A61K 39/35*    (2006.01)
*A61K 39/36*    (2006.01)
*A61K 39/00*    (2006.01)
*C07K 14/00*    (2006.01)
(52) U.S. Cl. ............................... 424/184.1; 424/185.1; 424/275.1; 530/350
(58) Field of Classification Search ...................... None
See application file for complete search history.

(56) References Cited

U.S. PATENT DOCUMENTS

| | | | | |
|---|---|---|---|---|
| 5,583,046 A | * | 12/1996 | Valenta et al. | ......... 435/252.33 |
| 6,187,311 B1 | * | 2/2001 | Nishiyama et al. | ...... 424/191.1 |
| 2003/0039660 A1 | * | 2/2003 | King et al. | .............. 424/185.1 |

FOREIGN PATENT DOCUMENTS

| | | |
|---|---|---|
| WO | WO-02/40676 A2 | 5/2002 |
| WO | WO-02/070665 A2 | 9/2002 |

OTHER PUBLICATIONS

King, T.P., et al. 2001. Recombinant Allergens with Reduced Allergenicity but Retaining Immunogenicity of the Natural Allergens: Hybrids of Yellow Jacket and Paper Wasp Venom Allergen Antigen 5s. J. Immunol. 166(10):6057-6065.*
Son, D.Y., et al. 1999. Pollen-related food allergy: cloning and immunological analysis of isoforms and mutants of Mal d 1, the major apple allergen, and Bet v 1, the major birch pollen allergen. Eur. J. Nutr. 38:201-215.*
Sergel, T.A., et al. 2000 J Virol 74(11): 5101-5107.*
Yuan, S-M., et al. 1998 Proteins 30: 136-143.*
Blumenthal, M.N., et al. in Allergens and Allergen Immunotherapy, 2004 Marcel Dekker, Inc. pp. 37-50.*
Reese, G., et al. 2005 The Journal of Immunology 175: 8354-8364.*
Niu, C-K., et al. 2006 Respiratory Medicine, E-pub on Jan. 3, 2006, 10 pages.*

Liang, S., et al. "Grafting of Protein-Protein Interaction Epitope", Journal of Biomolecular Structure & Dynamics, vol. 17, Issue No. 5, Apr. 2000, pp. 821-828.
King, T.P., et al. "Recombinant Allergens with Reduced Allergenicity but Retaining Immunogenicity of the Naterual Allergens: Hybrids of Yellow Jacket and Paper Wasp Venom Allergen Antigen 5s1", Journal of Immunology, vol. 166, No. 10, May 15, 2001, pp. 6057-6065.
Scheurer, S., et al. "Cross-reactivity and epitope analysis of Pru a 1, the major cherry allergen" Molecular Immunology, vol. 36, No. 3, Feb. 1999, pp. 155-167.
Holm, J., et al. "Molecular basis of allergic cross-reactivity between group 1 major allergens from birch and apple", Journal of Chromatography. Biomedical Applications, vol. 756, No. 1-2, May 25, 2001, pp. 307-313.
Uehara, Motoharu, et al. "Sequential IgE epitope analysis of a birch pollen allergen (Bet v1) and an apple allergen (Mal d1)", Allergology International, vol. 50, No. 1, 2001. pp. 57-62.
Punnonen, J. "Molecular Breeding of Allergy Vaccines and Antiallergic Cytokines", International Archives of Allergy and Immunology, vol. 121, No. 3, 2000, pp. 173-182.
Holm, J., et al. "Epitope Grafting: the Shaping of a Conformational Bet v 1 Epitope on Mal d 1, the Major Apple Allergen", Journal of Allergy and Clinical Immunology, vol. 111, No. 4, Apr. 20, 2003, p. 909.
http://www.allergen.org/List.htm; Allergen Nomenclature: International Union of Immunological Societies Allergen Nomenclature Sub-Committee; 39 pages; last visited—Apr. 3, 2006.
*Allergy: Principles and Practice*, Middleton et al. Ed., Mosby, 4th Edition, 1993; Chapter 20 pp. 529-540.
*Essential Allergy*, Mygind et al. Ed., Blackwell Science, 2nd Edition, 1996; Part 3 pp. 81-108.
Burks et al., Eur. J. Biochem, 1997, 245:334-339.
Kundrot et al., "Which strategy for protein crystallization project?" Cell. Mol. Life Sci. 61:525-536, 2004.
Ngo et al, "Computational Complexity, Protein Structure Prediction, and the Levinthal Paradox." The Protein Folding Problem and Tertiary Structure Prediction, Ed. K. Merz and S. Le Grand, Boston: Birkhauser, 1994, 491-495.
Lebecque et al., "Immunologic characterization of monoclonal antibodies that modulate human IgE binding to the major birch pollen allergen Bet v 1." J. Aller. Clin. Immunol. 99(3):374-384, 1997.
Skolnick et al., "From genes to protein structure and function: novel applications of computational approaches in the genomic era." Trends in Biotech. 18:34-39, 2000.
Attwood et al., "The Babel of bioinformatics," Science, 290(5491):471-473.

* cited by examiner

*Primary Examiner*—Karen Cochrane Carlson
*Assistant Examiner*—Marsha Tsay
(74) *Attorney, Agent, or Firm*—Darby & Darby P.C.

(57)    ABSTRACT

The present invention relates to novel recombinant protein variants that are useful as immunotherapeutic components. Also the present invention relates to DNA sequences encoding said protein variants as well as compositions comprising said protein variants.

5 Claims, 47 Drawing Sheets

```
                            10                    20                    30                    40                    50                    60
Lep d 2 (S66499)  G K M T F K D C G H G E V T E L D I S G C S G · D T C V I H R G Q K M T L D A K F A A N Q D T N K V T I K V L A K V A G T
Der p 2 (P49278)  D Q V D V K D C A N H E I K K V L V P G C H G S E P C I I H R G K P F Q L E A V F E A N Q N T K T A K I E I K A S I D G L
                            10                    20                    30                    40                    50                    60

70                    80                    90                   100                   110                   120
Lep d 2 (S66499)  T I Q V P G I L E T D G C K V L K C P I K K G E A L D F N Y G M T I P A I T P K I K · A D V T A E L V G D H G V M A C G T I H G Q · V E
Der p 2 (P49278)  E V D V P G I D P N A C H Y M K C P L V K G Q Q Y D I K Y T W N V P K I A P K S E N V V V T V K V M G D D G V L A C A I A T H A K I R D
                            70                    80                    90                   100                   110                   120
```

Figure 18

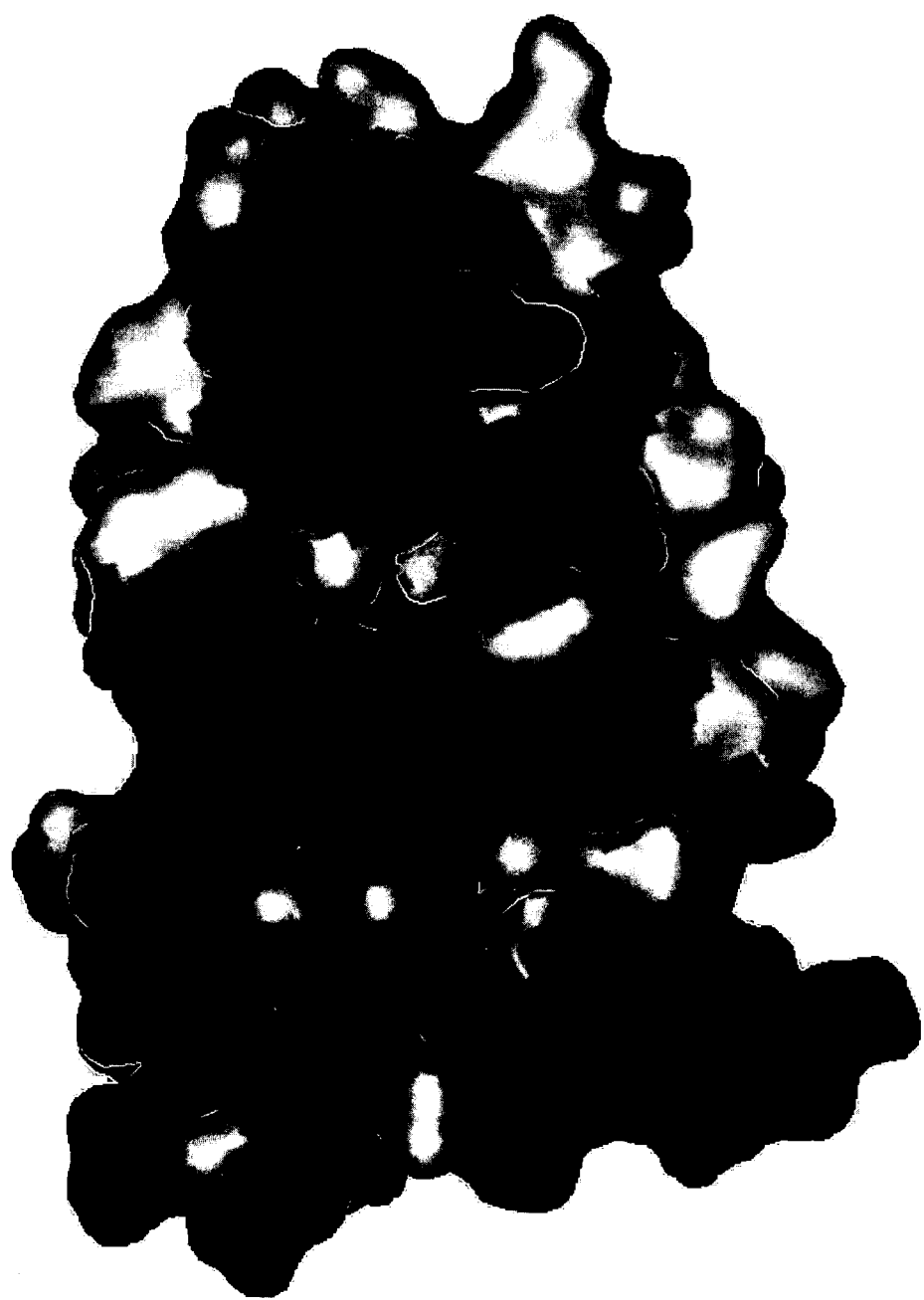
Figure 19A Front (0°)

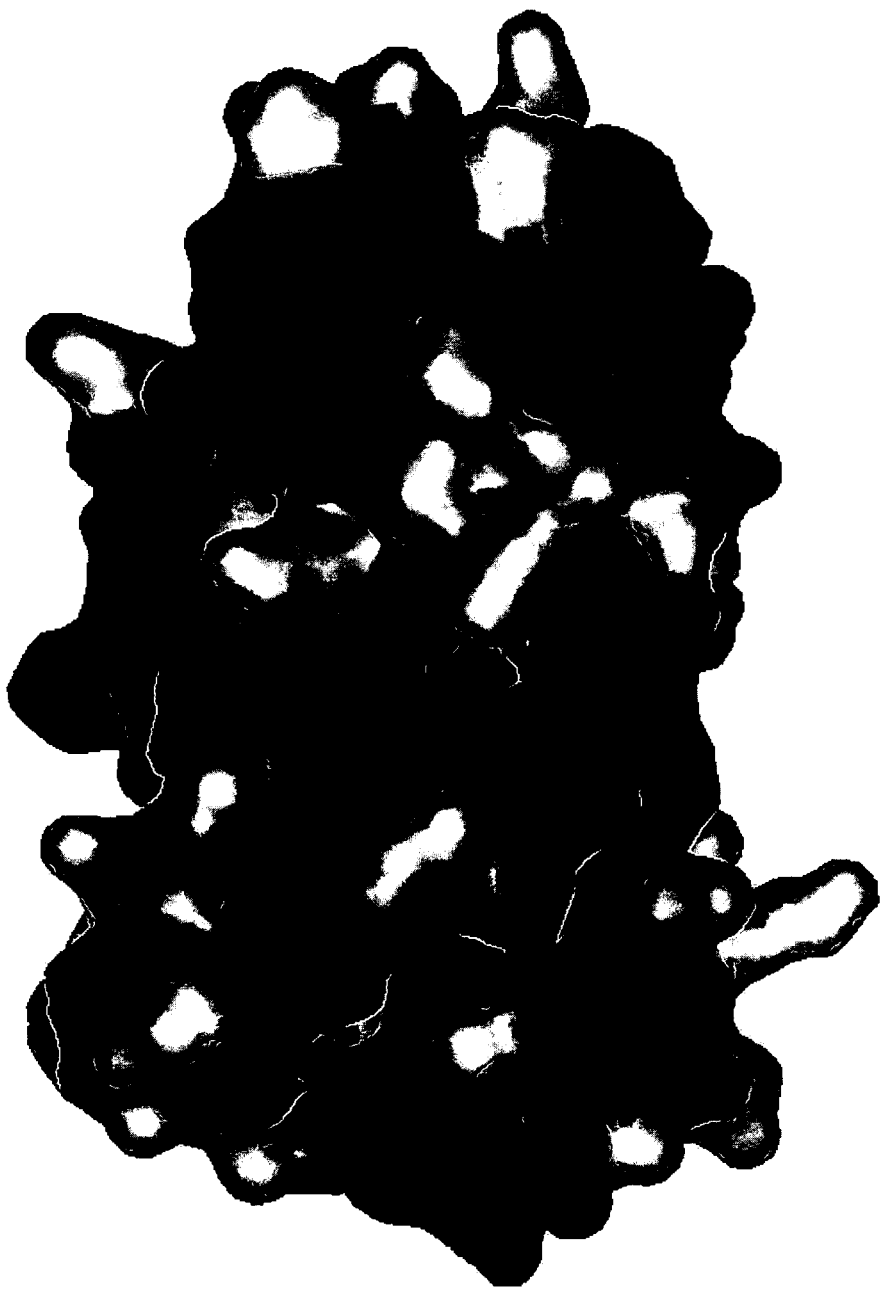
Figure 19B Turn 1 (90°)

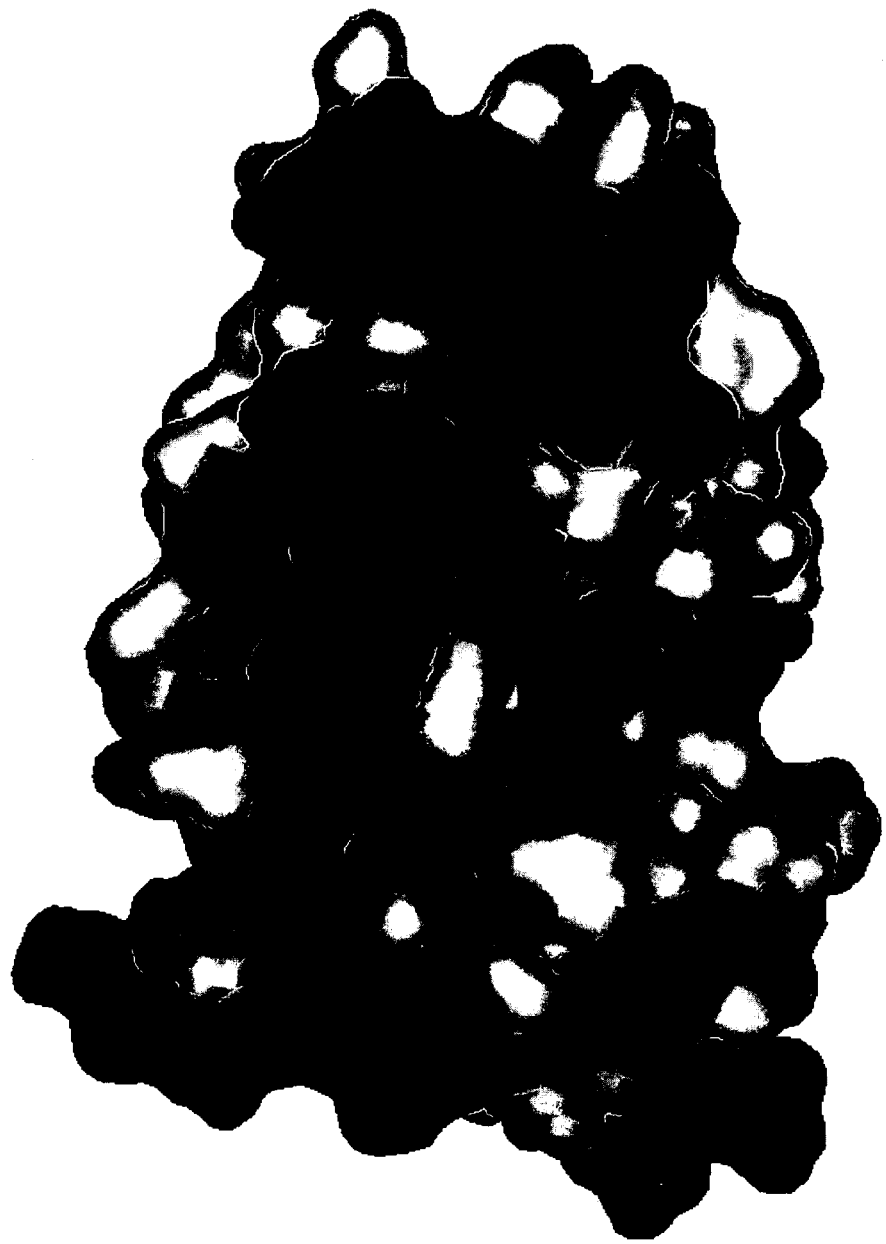
Figure 19C Turn 2 (180°)

Figure 19D Turn 3 (270°)

Figure 20A Grafting Front (0°)

Figure 20B Grafting Turn 1 (90°)

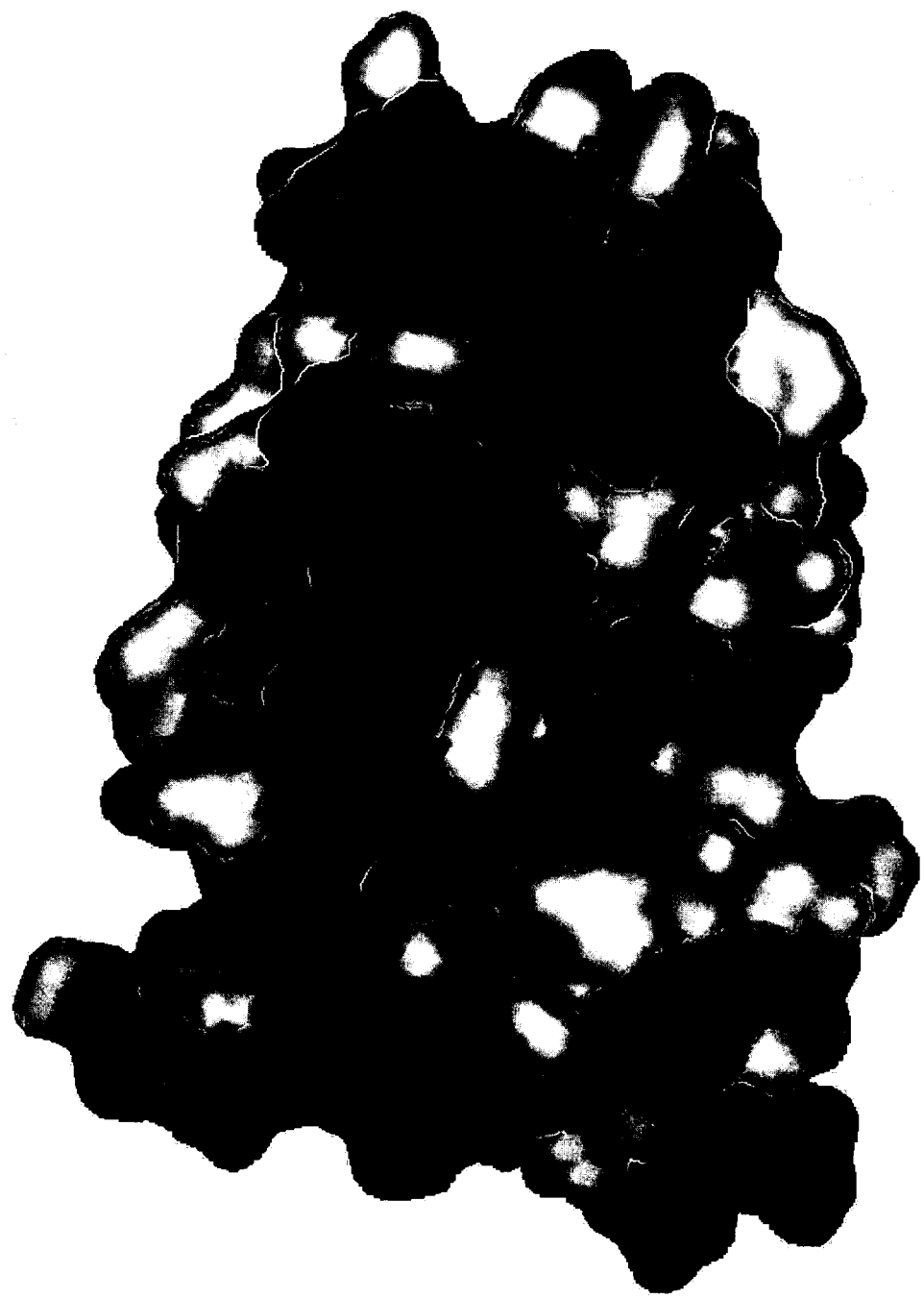
Figure 20C Grafting Turn 2 (180°)

Figure 20D Grafting Turn 3 (270°)

```
                       1           10            20           30            40             50
                       •            •             •            •             •              •
Gly d 2(AJ272216)  G K M K F K D C G K G E V T E L D I T D C S G - D F C V I H R G K P L T L E A K F A A N Q D T K A T I K V L A K V A G
Der p 2 (P49278)   D Q V D V K D C A N H E I K K V L V P G C H G S E P C I I H R G K P F Q L E A V F E A N Q N T K T A K I E I K A S I D G
                       •            •             •            •             •              •
                      10           20            30           40             50             60

60           70            80           90            100            110            120
                       •            •             •            •             •              •              •
Gly d 2(AJ272216)  T P I Q V P G I L E T D G C K F V K C P I K K G D P I D F K Y T T - T V P A I L P K V K A E V T A E L V I G D H G V L A C G R F G R Q - V E -
Der p 2 (P49278)   L E V D V P G I D P N A C H Y M K C P L V K G Q Q Y D I K Y T W N V P K I A P K S E N V V V T V K V M G D D G V L A C A I A T H A K I R D
                       •            •             •            •             •              •              •
                      70           80            90          100            110            120
```

Figure 22

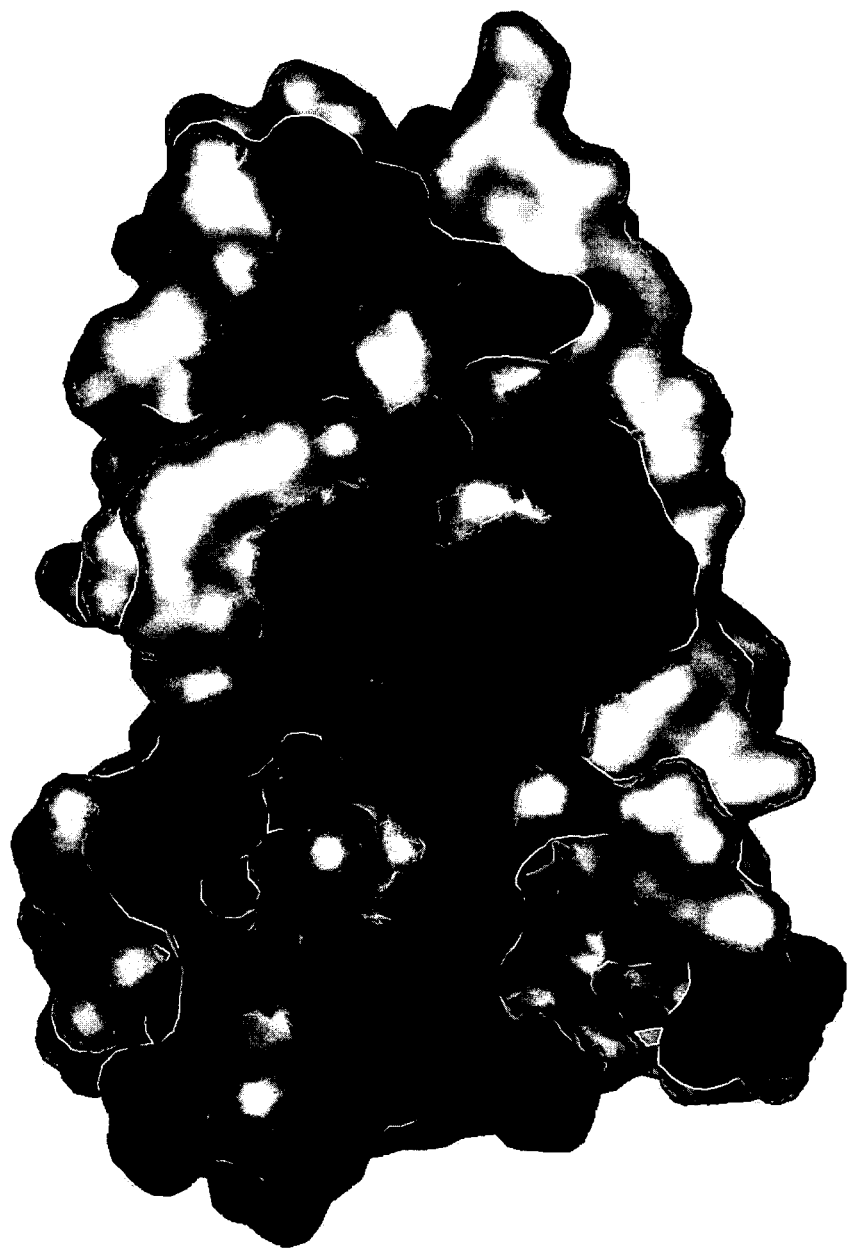
Figure 23 A Front (0°)

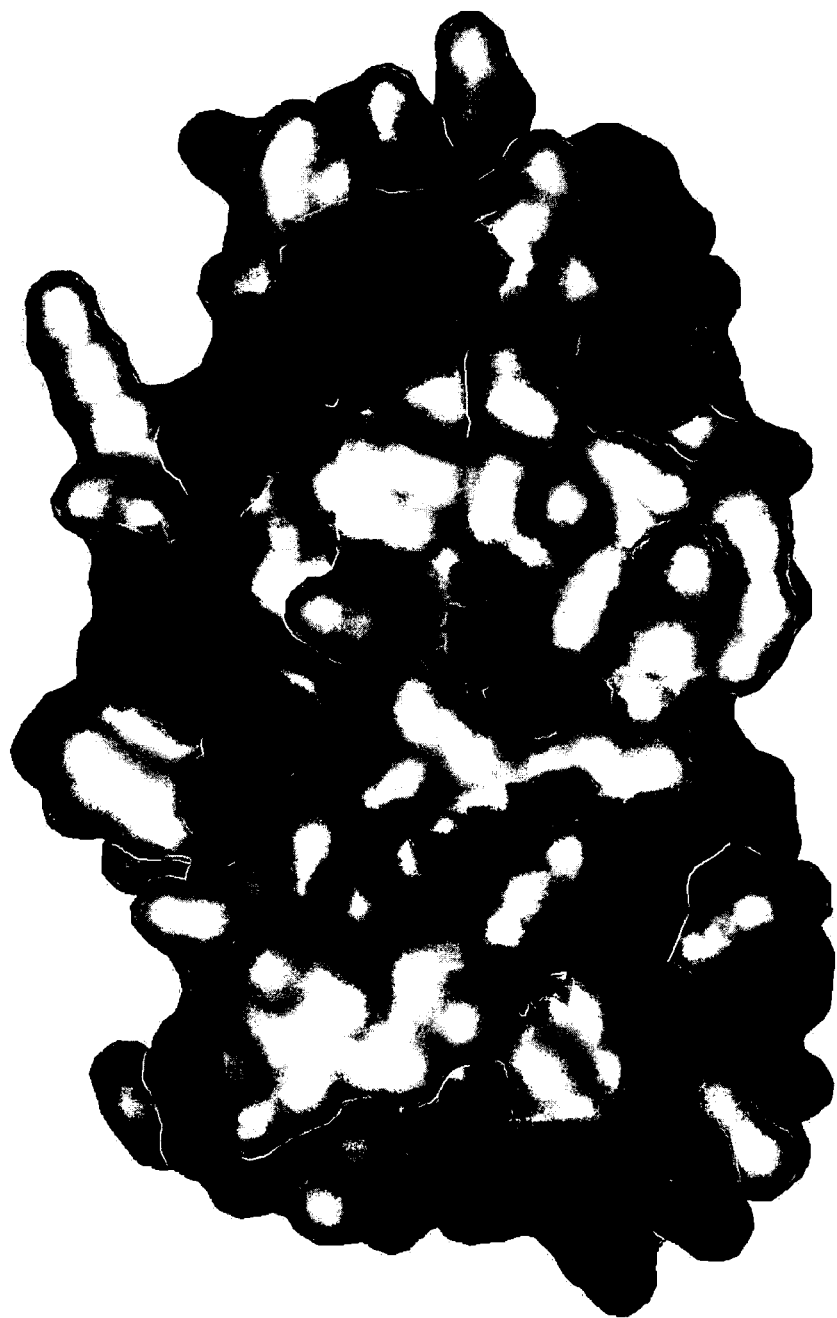
Figure 23B Turn 1 (90°)

Figure 23C Turn 2 (180°)

Figure 23 D Turn 3 (270°)

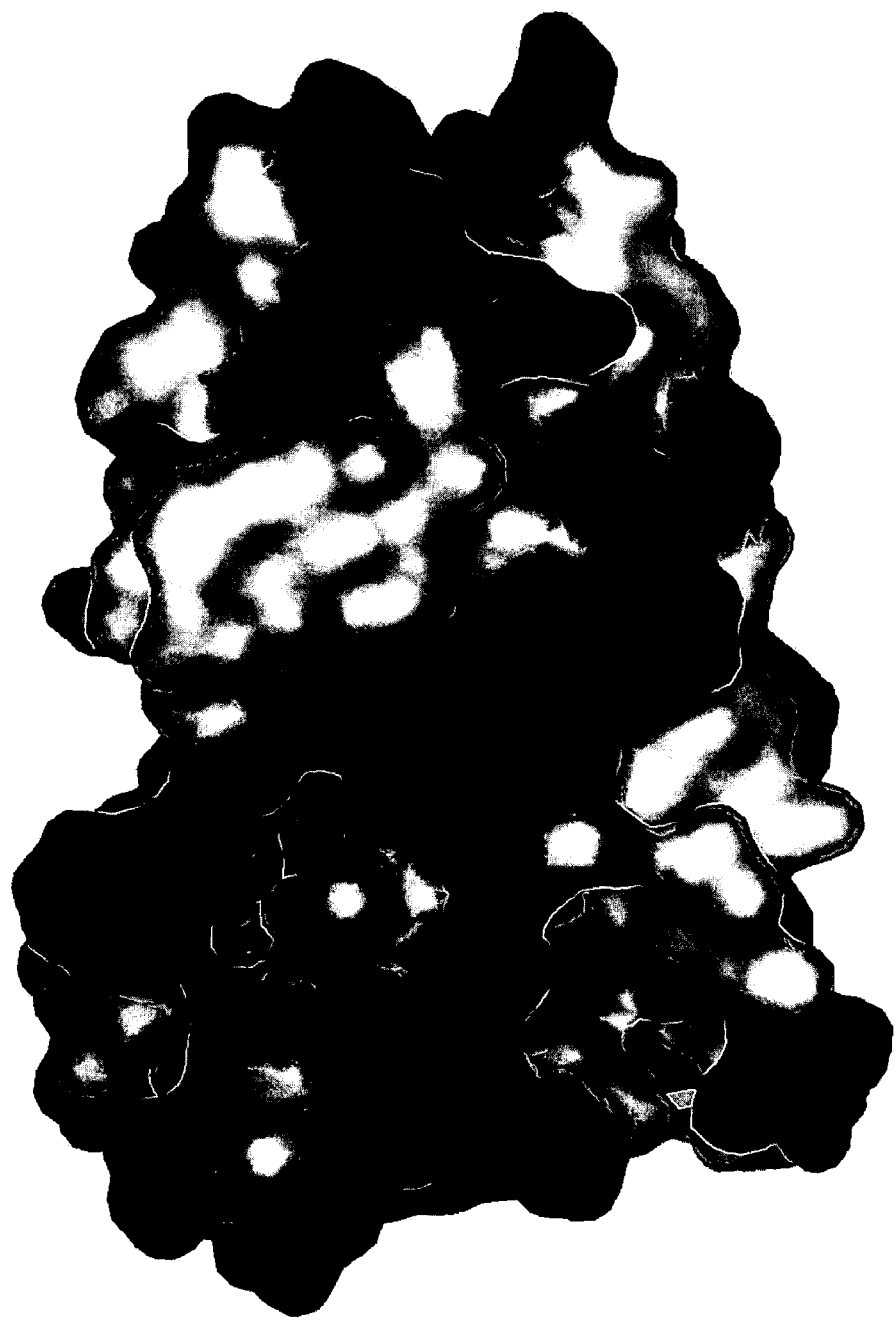
Figure 24A. grafting Front (0°)

Figure 24B grafting Turn 1 (90°)

Figure 24C grafting Turn 2 (180°)

Figure 24D grafting Turn 3 (270°)

```
                           SEQUENCE LISTING

<160> NUMBER OF SEQ ID NOS: 10

<210> SEQ ID NO 1
<211> LENGTH: 158
<212> TYPE: PRT
<213> ORGANISM: Malus x domestica

<400> SEQUENCE: 1

Gly Val Tyr Thr Tyr Glu Asn Glu Tyr Thr Ser Glu Ile Pro Pro Pro
1               5                   10                  15

Arg Leu Phe Lys Ala Phe Val Leu Asp Ala Asp Thr Leu Ile Pro Gln
            20                  25                  30

Ile Ala Pro Gln Ala Ile Lys His Ala Glu Ile Leu Ser Gly Asp Gly
        35                  40                  45

Gly Pro Gly Thr Ile Lys Lys Ile Thr Phe Gly Glu Gly Ser Gln Tyr
    50                  55                  60

Gly Tyr Val Lys His Lys Ile Asp Ser Val Asp Glu Ala Asn Tyr Ser
65                  70                  75                  80

Tyr Ala Tyr Thr Leu Ile Glu Gly Asp Ala Leu Thr Asp Thr Ile Glu
                85                  90                  95

Lys Val Ser Tyr Glu Thr Lys Leu Val Ala Ser Gly Ser Gly Ser Ile
            100                 105                 110

Ile Lys Ser Ile Ser His Tyr His Thr Lys Gly Asp Val Glu Ile Met
        115                 120                 125

Glu Glu His Val Lys Ala Gly Lys Glu Lys Ala His Gly Leu Phe Lys
    130                 135                 140

Leu Ile Glu Ser Tyr Leu Lys Asp His Pro Asp Ala Tyr Asn
145                 150                 155

<210> SEQ ID NO 2
<211> LENGTH: 158
<212> TYPE: PRT
<213> ORGANISM: Malus x domestica

<400> SEQUENCE: 2

Gly Val Tyr Thr Tyr Glu Asn Glu Tyr Thr Ser Glu Ile Pro Pro Pro
1               5                   10                  15

Arg Leu Phe Lys Ala Phe Val Leu Asp Ala Asp Asn Leu Ile Pro Lys
            20                  25                  30

Ile Ala Pro Gln Ala Ile Lys His Ala Glu Asn Ile Glu Gly Asn Gly
        35                  40                  45

Gly Pro Gly Thr Ile Lys Lys Ile Thr Phe Gly Glu Gly Ser Gln Tyr
    50                  55                  60

Lys Tyr Val Lys His Arg Ile Asp Ser Val Asp His Ala Asn Tyr Ser
65                  70                  75                  80

Tyr Ala Tyr Thr Leu Ile Glu Gly Asp Ala Leu Thr Asp Thr Ile Glu
                85                  90                  95

Lys Val Ser Tyr Glu Thr Lys Leu Val Ala Ser Gly Ser Gly Ser Ile
            100                 105                 110

Ile Lys Ser Ile Ser His Tyr His Thr Lys Gly Asp Val Glu Ile Met
```

```
                    115                 120                 125
Glu Glu His Val Lys Ala Gly Lys Glu Lys Ala His Gly Leu Phe Lys
        130                 135                 140
Leu Ile Glu Ser Tyr Leu Lys Asp His Pro Asp Ala Tyr Asn
145                 150                 155

<210> SEQ ID NO 3
<211> LENGTH: 159
<212> TYPE: PRT
<213> ORGANISM: Malus x domestica

<400> SEQUENCE: 3

Gly Val Tyr Thr Tyr Glu Asn Glu Tyr Thr Ser Val Ile Pro Pro Ala
1               5                   10                  15

Arg Leu Phe Lys Ala Phe Val Leu Asp Ala Asp Asn Leu Ile Pro Lys
                20                  25                  30

Ile Ala Pro Gln Ala Ile Lys His Ala Glu Ile Leu Glu Gly Asp Gly
            35                  40                  45

Gly Pro Gly Thr Ile Lys Lys Ile Thr Phe Gly Glu Gly Ser Gln Tyr
        50                  55                  60

Gly Tyr Val Lys His Lys Ile Asp Ser Val Asp Glu Ala Asn Tyr Ser
65                  70                  75                  80

Tyr Ala Tyr Thr Leu Ile Glu Gly Asp Ala Leu Thr Asp Thr Ile Glu
                85                  90                  95

Lys Val Ser Tyr Glu Thr Lys Leu Val Ala Thr Pro Asp Gly Gly Ser
            100                 105                 110

Ile Ile Lys Ser Ile Ser His Tyr His Thr Lys Gly Asp Val Glu Ile
        115                 120                 125

Met Glu Glu His Val Lys Ala Gly Lys Glu Lys Ala His Gly Leu Phe
    130                 135                 140

Lys Leu Ile Glu Ser Tyr Leu Leu Asp His Ser Asp Ala Tyr Asn
145                 150                 155

<210> SEQ ID NO 4
<211> LENGTH: 158
<212> TYPE: PRT
<213> ORGANISM: Arabidopsis thaliana

<400> SEQUENCE: 4

Gly Ala Gln Ser His Ser Leu Glu Ile Thr Ser Ser Val Ser Ala Glu
1               5                   10                  15

Lys Ile Phe Ser Gly Ile Val Leu Asp Val Asp Thr Val Ile Pro Lys
                20                  25                  30

Ala Ala Thr Gly Ala Tyr Lys Ser Val Glu Val Lys Gly Asp Gly Gly
            35                  40                  45

Ala Gly Thr Val Arg Ile Ile Thr Leu Pro Glu Gly Ser Pro Ile Thr
        50                  55                  60

Thr Met Thr Val Arg Thr Asp Ala Val Asn Lys Glu Ala Leu Ser Tyr
65                  70                  75                  80

Asp Ser Thr Val Ile Asp Gly Asp Ile Leu Leu Gly Phe Ile Glu Ser
                85                  90                  95

Ile Glu Thr His Met Val Val Pro Thr Ala Asp Gly Gly Ser Ile
            100                 105                 110

Thr Lys Thr Thr Ala Ile Phe His Thr Lys Gly Asp Ala Val Val Pro
        115                 120                 125

Glu Glu Asn Ile Lys Phe Ala Asp Ala Gln Asn Thr Ala Leu Phe Lys
```

```
                130                 135                 140
Ala Ile Glu Ala Tyr Leu Ile Ala Asn Ser Asp Ala Tyr Asn
145                 150                 155

<210> SEQ ID NO 5
<211> LENGTH: 159
<212> TYPE: PRT
<213> ORGANISM: Betula pendula

<400> SEQUENCE: 5

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
                20                  25                  30

Val Ala Pro Gln Ala Ile Ser Ser Val Glu Asn Ile Glu Gly Asn Gly
            35                  40                  45

Gly Pro Gly Thr Ile Lys Lys Ile Ser Phe Pro Glu Gly Leu Pro Phe
        50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155

<210> SEQ ID NO 6
<211> LENGTH: 153
<212> TYPE: PRT
<213> ORGANISM: Arabidopsis thaliana

<400> SEQUENCE: 6

Gly Ala Gln Ser His Ser Leu Glu Ile Thr Ser Ser Val Ser Ala Glu
1               5                   10                  15

Lys Ile Phe Ser Gly Ile Val Leu Asp Val Asp Thr Val Ile Pro Lys
                20                  25                  30

Ala Ala Thr Gly Ala Tyr Lys Ser Val Glu Val Lys Gly Asp Gly Gly
            35                  40                  45

Ala Gly Thr Val Arg Ile Ile Thr Leu Pro Glu Gly Ser Pro Ile Thr
        50                  55                  60

Thr Met Thr Val Arg Thr Asp Ala Val Asn Lys Glu Ala Leu Ser Tyr
65                  70                  75                  80

Asp Ser Thr Val Ile Asp Gly Asp Ile Leu Leu Gly Phe Ile Glu Ser
                85                  90                  95

Ile Glu Thr His Met Val Val Pro Thr Ala Asp Gly Gly Ser Ile
            100                 105                 110

Thr Lys Thr Thr Ala Ile Phe His Thr Lys Gly Asp Ala Val Val Pro
        115                 120                 125

Glu Glu Asn Ile Lys Phe Ala Asp Ala Gln Asn Thr Ala Leu Phe Lys
    130                 135                 140

Ala Ile Glu Ala Tyr Leu Ile Ala Asn
145                 150
```

<210> SEQ ID NO 7
<211> LENGTH: 125
<212> TYPE: PRT
<213> ORGANISM: Lepidoglyphus destructor

<400> SEQUENCE: 7

Gly Lys Met Thr Phe Lys Asp Cys Gly His Gly Glu Val Thr Glu Leu
1               5                   10                  15

Asp Ile Ser Gly Cys Ser Gly Asp Thr Cys Val Ile His Arg Gly Gln
            20                  25                  30

Lys Met Thr Leu Asp Ala Lys Phe Ala Ala Asn Gln Asp Thr Asn Lys
        35                  40                  45

Val Thr Ile Lys Val Leu Ala Lys Val Ala Gly Thr Thr Ile Gln Val
    50                  55                  60

Pro Gly Leu Glu Thr Asp Gly Cys Lys Val Leu Lys Cys Pro Ile Lys
65                  70                  75                  80

Lys Gly Glu Ala Leu Asp Phe Asn Tyr Gly Met Thr Ile Pro Ala Ile
                85                  90                  95

Thr Pro Lys Ile Lys Ala Asp Val Thr Ala Glu Leu Val Gly Asp His
            100                 105                 110

Gly Val Met Ala Cys Gly Thr Ile His Gly Gln Val Glu
        115                 120                 125

<210> SEQ ID NO 8
<211> LENGTH: 129
<212> TYPE: PRT
<213> ORGANISM: Dermatophagoides pteronyssinus

<400> SEQUENCE: 8

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Cys Ala Ile Ala Thr His Ala Lys Ile Arg
        115                 120                 125

Asp

<210> SEQ ID NO 9
<211> LENGTH: 158
<212> TYPE: PRT
<213> ORGANISM: Malus x domestica

<400> SEQUENCE: 9

Gly Val Tyr Thr Tyr Glu Asn Glu Tyr Thr Ser Glu Ile Pro Pro Pro
1               5                   10                  15

```
                                                              -continued
Arg  Leu  Phe  Lys  Ala  Phe  Val  Leu  Asp  Ala  Asp  Asn  Leu  Ile  Pro  Lys
               20                  25                       30

Ile  Ala  Pro  Gln  Ala  Ile  Lys  His  Ala  Glu  Ile  Leu  Glu  Gly  Asp  Gly
               35                  40                       45

Gly  Pro  Gly  Thr  Ile  Lys  Lys  Ile  Thr  Phe  Gly  Glu  Gly  Ser  Gln  Tyr
     50                       55                  60

Gly  Tyr  Val  Lys  His  Lys  Ile  Asp  Ser  Val  Asp  Glu  Ala  Asn  Tyr  Ser
65                       70                  75                            80

Tyr  Ala  Tyr  Thr  Leu  Ile  Glu  Gly  Asp  Ala  Leu  Thr  Asp  Thr  Ile  Glu
                    85                  90                       95

Lys  Val  Ser  Tyr  Glu  Thr  Lys  Leu  Val  Ala  Ser  Gly  Ser  Gly  Ser  Ile
               100                      105                      110

Ile  Lys  Ser  Ile  Ser  His  Tyr  His  Thr  Lys  Gly  Asp  Val  Glu  Ile  Met
               115                      120                      125

Glu  Glu  His  Val  Lys  Ala  Gly  Lys  Glu  Lys  Ala  His  Gly  Leu  Phe  Lys
          130                       135                      140

Leu  Ile  Glu  Ser  Tyr  Leu  Lys  Asp  His  Pro  Asp  Ala  Tyr  Asn
145                      150                      155

<210> SEQ ID NO 10
<211> LENGTH: 125
<212> TYPE: PRT
<213> ORGANISM: Glycyphagus domesticus

<400> SEQUENCE: 10

Gly  Lys  Met  Lys  Phe  Lys  Asp  Cys  Gly  Lys  Gly  Glu  Val  Thr  Glu  Leu
1               5                        10                       15

Asp  Ile  Thr  Asp  Cys  Ser  Gly  Asp  Phe  Cys  Val  Ile  His  Arg  Gly  Lys
               20                  25                       30

Pro  Leu  Thr  Leu  Glu  Ala  Lys  Phe  Ala  Ala  Asn  Gln  Asp  Thr  Thr  Lys
               35                  40                       45

Ala  Thr  Ile  Lys  Val  Leu  Ala  Lys  Val  Ala  Gly  Thr  Pro  Ile  Gln  Val
     50                       55                  60

Pro  Gly  Leu  Glu  Thr  Asp  Gly  Cys  Lys  Phe  Val  Lys  Cys  Pro  Ile  Lys
65                       70                  75                            80

Lys  Gly  Asp  Pro  Ile  Asp  Phe  Lys  Tyr  Thr  Thr  Thr  Val  Pro  Ala  Ile
                    85                  90                       95

Leu  Pro  Lys  Val  Lys  Ala  Glu  Val  Thr  Ala  Glu  Leu  Val  Gly  Asp  His
               100                      105                      110

Gly  Val  Leu  Ala  Cys  Gly  Arg  Phe  Gly  Arg  Gln  Val  Glu
               115                      120                      125
```

PROTEIN VARIANTS OF NATURALLY OCCURRING ALLERGENS

CROSS REFERENCE TO RELATED APPLICATIONS

The present application claims the benefit of priority under 35 U.S.C. §119(e) of provisional application 60/422,983, filed Nov. 1, 2002, and priority under 35 U.S.C. §119(a)-(d) of Danish patent application no. PA 2002 01686, filed Nov. 1, 2002. Each of the foregoing applications is hereby incorporated herein by reference in its entirety.

FIELD OF THE INVENTION

The present invention relates to immunotherapy, in particular the present invention relates to allergy vaccination strategies employing novel recombinant proteins.

Also, the invention relates to a composition comprising a mixture of the novel recombinant protein variants.

BACKGROUND OF THE INVENTION

Allergy is a major health problem in countries where Western lifestyle is adapted. Furthermore, the prevalence of allergic disease is increasing in these countries. Although allergy in general may not be considered a life-threatening disease, asthma annually causes a significant number of deaths. An exceptional prevalence of about 30% in teenagers conveys a substantial loss in quality of life, working days and money, and warrants a classification among major health problems in the Western world.

Allergy is a complex disease. Many factors contribute to the sensitisation event. Among these is the susceptibility of the individual defined by an as yet insufficiently understood interplay between several genes. Another important factor is allergen exposure above certain thresholds. Several environmental factors may be important in the sensitisation process including pollution, childhood infections, parasite infections, intestinal microorganisms, etc. Once an individual is sensitised and the allergic immune response established, the presence of only minute amounts of allergen is efficiently translated into symptoms.

The natural course of allergic disease is usually accompanied by aggravation at two levels. Firstly, an progression of symptoms and disease severity, as well as disease progression, for example from hay fever to asthma. Secondly, dissemination in offending allergens most often occurs resulting in allergic multi-reactivity. Chronic inflammation leads to a general weakening of the mucosal defense mechanisms resulting in unspecific irritation and eventually destruction of the mucosal tissue. Infants may become sensitised primarily to foods, i.e. milk, resulting in eczema or gastrointestinal disorders; however, most often they outgrow these symptoms spontaneously. These infants are at risk of developing inhalation allergy later in their lives.

The most important allergen sources are found among the most prevalent particles of a certain size in the air we breathe. These sources are remarkably universal and include grass pollens and house dust mite faecal particles, which together are responsible for approximately 50% of all allergies. Of global importance are also animal danders, i.e. cat and dog dander, other pollens, such as mugwort pollens, and micro-fungi, such as Alternaria. On a regional basis yet other pollens may dominate, such as birch pollen in Northern and Central Europe, ragweed in the Eastern and Central United States, and Japanese cedar pollen in Japan. Insects, i.e. bee and wasp venoms, and foods each account for approximately 2% of all allergies.

All IgE-mediated allergic responses are directed towards proteins. In recent years the characterization of allergen molecules has advanced considerably facilitated by the application of modern techniques within molecular and structural biology. These studies have failed to demonstrate the existence of a common structural motif or a biological function shared by all allergens. It must be anticipated that any protein is a potential allergen, and that the most important allergens, i.e. the major allergens, are the most abundant proteins on airborne particles of a size facilitating their presentation to the immune system.

Allergy, i.e. type I hyper-sensitivity, is caused by an inappropriate immunological reaction to foreign non-pathogenic substances. Important clinical manifestations of allergy include asthma, hay fever, eczema, and gastro intestinal disorders. The allergic reaction is prompt and peaks within 20 minutes upon contact with the offending allergen often followed by a late reaction 8-24 hours later. Furthermore, the allergic reaction is specific in the sense that a particular individual is sensitised to particular allergen(s), whereas the individual does not necessarily show an allergic reaction to other substances known to cause allergic disease. The allergic phenotype is characterized by a pronounced inflammation of the mucosa of the target organ and by the presence of allergen specific antibody of the IgE class in the circulation and on the surfaced of mast-cells and basophils.

An allergic attack is initiated by the reaction of the foreign allergen with allergen specific IgE antibodies, when the antibodies are bound to high affinity IgE specific receptors on the surface of mast-cells and basophils. The mast-cells and basophils contain preformed mediators, i.e. histamine, tryptase, and other substances, which are released upon cross-linking of two or more receptor-bound IgE antibodies. IgE antibodies are cross-linked by the simultaneous binding of one allergen molecule. It therefore follows that a foreign substance having only one antibody binding epitope does not initiate an allergic reaction. The cross-linking of receptor bound IgE on the surface of mast-cells also leads to release of signaling molecules responsible for the attraction of eosinophils, allergen specific T-cells, and other types of cells to the site of the allergic response. These cells in interplay with allergen, IgE and effector cells, lead to a renewed flash of symptoms occurring 12-24 hours after allergen encounter.

Allergy disease management comprises diagnosis and treatment including-prophylactic treatments. Diagnosis of allergy is concerned with the demonstration of allergen specific IgE and identification of the allergen source. In many cases a careful anamnesis may be sufficient for the diagnosis of allergy and for the identification of the offending allergen source material. Most often, however, the diagnosis is supported by objective measures, such as skin prick test, blood test, or provocation test. The principle behind the blood test is the demonstration of specific IgE using an array of allergen sources. The therapeutic options fall in three major categories. The first opportunity is allergen avoidance or reduction of the exposure. Whereas allergen avoidance is obvious e.g. in the case of food allergens, it may be difficult or expensive, as for house dust mite allergens, or it may be impossible, as for pollen allergens. The second and most widely used therapeutic option is the prescription of symptomatic drugs. Symptomatic drugs are safe and efficient; however, they do not alter the natural cause of the disease, neither do they control the disease dissemination. The third therapeutic alternative is specific allergy vaccination i.e. specific immuno therapy that in most cases reduces or alleviates the allergic symptoms caused by the allergen in question.

Specific allergy vaccination is a causal treatment for allergic disease. It interferes with basic immunological mechanisms resulting in persistent improvement of the patients' immune status. Thus, the protective effect of specific allergy vaccination extends beyond the treatment period in contrast to symptomatic drug treatment. Some patients receiving the treatment are cured, and in addition, most patients experience a relief in disease severity, or at least an arrest in disease aggravation. Thus, specific allergy vaccination has preventive effects reducing the risk of hay fever developing into asthma, and reducing the risk of developing new sensitivities.

Specific allergy vaccination is, in spite of its virtues, not in widespread use, primarily for two reasons. One reason is the inconveniences associated with the traditional vaccination programme that comprises repeated vaccinations over a several months. The other reason is, more importantly, the risk of allergic side reactions. Ordinary vaccinations against infectious agents are efficiently performed using a single or a few high dose immunizations. This strategy, however, cannot be used for allergy vaccination since a pathological immune response is already ongoing.

Specific allergy vaccination is therefore carried out using multiple immunizations applied over an extended time period. The course is divided in two phases, the up dosing and the maintenance phase. In the up dosing phase increasing doses are applied, typically over a 16 week period, starting with minute doses. When the recommended maintenance dose is reached, this dose is applied for the maintenance phase, typically with injections every six weeks. Following each injection the patient must remain under medical attendance for 20-60 minutes due to the risk of anaphylactic side reactions, which in principle could be life-threatening. In addition, the clinic should be equipped to support emergency treatment. There is no doubt that eliminating the risk for allergic side reactions inherent in the vaccine would facilitate a more general use, possibly even enabling self vaccination at home.

The immunological mechanism underlying successful allergy vaccination is not known in detail. A specific immune response, such as the production of antibodies against a particular pathogen, is known as an adaptive immune response. This response can be distinguished from the innate immune response, which is an unspecific reaction towards pathogens.

An allergy vaccine is bound to address the adaptive immune response, which includes cells and molecules with antigen specificity, such as T-cells and the antibody producing B-cells. B-cells cannot mature into antibody producing cells without help from T-cells of the corresponding specificity. T-cells that participate in the stimulation of allergic immune responses are primarily of the Th2 type. Establishment of a new balance between Th1 and Th2 cells has been proposed to be beneficial and central to the immunological mechanism of specific allergy vaccination. Whether this is brought about by a reduction in Th2 cells, a shift from Th2 to Th1 cells, or an up-regulation of Th1 cells is controversial.

Recently, regulatory T-cells have been proposed to be important for the mechanism of allergy vaccination. According to this model regulatory T-cells, i.e. Th3 or Th1 cells, down-regulate both Th1 and Th2 cells of the corresponding antigen specificity. In spite of these ambiguities it is generally believed that an active vaccine must have the capacity to stimulate allergen specific T-cells, preferably TH1 cells.

With respect to allergen specific antibodies during the course of specific allergy vaccination an important observation is that in spite of clinical improvement there seem to be no corresponding change in IgE. Allergen specific IgE may provisionally rise early in treatment, but then falls back to pre-treatment levels during the treatment and may subsequently show a gradual decrease. Clinical improvement, on the other hand, is steadily increasing during the entire treatment period.

Another important observation is a large increase in allergen specific IgG early in the treatment period. Allergen specific IgG typically increases to concentrations hundreds or thousands times that of IgE. It has been proposed that allergen specific IgG is important for the immunological mechanism of specific allergy vaccination, since it can interfere or 'block' the interaction between IgE and the allergen. According to this model it is likely that IgG needs to undergo affinity maturation and/or increase in concentration by repeated immunizations before it can efficiently compete with IgE for binding to the allergen explaining the steady increase in clinical improvement observed during treatment.

The human immune system has two different ways of specific molecular recognition: via the T-cell receptor present on the surface of T-cells, and via the antibodies, which may be bound to the surface of the B-cells producing them, they may be free in solution, or they may be bound to specific receptors on the surface of a variety of cells in the immune system. Recognition via the T-cell receptor requires that the antigen is internalized and digested, and a fragment of the antigen is presented on the cell surface in complex with major histocompatibility complex (MHC), by an antigen presenting cell. The entire complex is recognized by the T-cell receptor.

The antigen presenting cell can be a professional antigen presenting cell, i.e. a macrophage, dendritic cell or a B-cell. Macrophages and dendritic cells ingest antigen by phagocytosis; whereas B-cells, capture antigen via surface bound antibody for subsequent internalisation and presentation. A T-cell epitope is a polypeptide fragment of 15-20 amino acids.

The B-cell epitope, i.e. antibody binding epitope, is different from the linear T-cell epitopes. Although antibodies that are raised in experimental animals by immunization in Freunds complete adjuvant may bind to linear polypeptide fragments, i.e. sequential epitopes, such antibodies are rarely raised during the natural response to allergens. Antibodies bind to a section of the surface of the correctly folded antigen molecule.

IgE epitopes of naturally occurring allergens are thus envisaged to consist of a number of surface exposed amino acids in a confined surface area that are supported by the backbone and the overall three-dimensional structure of the allergen. Such "epitope amino acids" are almost always found as either single amino acids or in clusters consisting of a few amino acids distributed over a large portion of the primary sequence of the allergen "brought together" on the surface upon folding of the molecule. The antibody binding epitope extends typically over approximately 800-900 $Å^2$, but an even larger area is "masked" by the binding of the antibody. This means that upon binding of an antibody to an epitope, an area of up to 2000 $Å^2$ becomes inaccessible to binding of other antibody molecules.

The affinity of the interaction between the antibody and the antigen is not only dependent on the attracting electrostatic forces, i.e. van der Waal's interactions, hydrogen bonding, and ion bridges, but also on the entropy gained by the almost complete expulsion of water molecules from the interface. Thus, the fit between the contours of the two molecular surfaces may be said to be an important parameter in defining the binding strength of the interaction. It follows that denaturation, i.e. unfolding, of the antigen (or allergen) usually destroys the antibody binding epitope, and binding of antibody will no longer be feasible in a physiological concentration range. It follows also, that if an amino acid in the epitope is substituted with another amino acid it will result in a reduction of the affinity of the interaction. The extent of the reduced antibody binding affinity depends on both the specific substituted amino acid and the antibody in question. It has e.g. been shown that one single amino acid substitution in an antigen can affect the interaction between antigen and antibody by a factor one thousand.

Attempts to improve vaccines for specific allergy vaccination by chemical modification have been performed for over 30 years and include multifarious approaches with one overall objective: to improve safety while not compromising efficacy; or in other words, to reduce IgE binding while not compromising immunogenicity.

Initial approaches included complete denaturation of the allergen. However, human trials have failed to show efficacy, which could be due to the non-efficient generation of a protective immune response. For the purpose of addressing T-cells in the allergic immune response, medium sized synthetic peptides (50-60 amino acids in length) were tested in human trials. Although the peptides showed some effect in very high doses, the trials were terminated due to the appearance of irregular side reactions. From these trials it seems that efficacy is compromised in the absence of antibody binding epitopes in the vaccine.

Other early attempts included chemical modification of allergen extracts either by acetylation (epitope masking), conjugation to large polymers (polyethyleneglycol), or polymerization into large so-called 'allergoids' by formaldehyde or glutaraldehyde. The former two concepts never entered human trials, whereas the 'allergoids' are currently in routine clinical use, however, without the benefit of improved safety. The reason for this is probably that chemical cross-linking randomly destroys some of the epitopes, which necessitates the use of higher doses for optimal efficacy, thereby increasing the level of allergic side effects approximately to the level observed using conventional allergy vaccines.

Approaches to improve allergy vaccines using genetic engineering include various strategies to disrupt the three-dimensional structure of the allergen vaccine molecules. Among these are substitutions of cysteine residues taking part in disulphide bridging. Another strategy is to assemble several naturally occurring amino acid substitutions into one molecule by site directed mutagenesis. A common characteristic of these strategies is to disrupt the tertiary structure of the vaccine, or at least not to consider preservation of the three-dimensional structure important.

Another commonly used approach has been to produce recombinant mutant variants of correctly folded naturally occurring allergens. The mutations are usually selected so as to reduce IgE affinity of the mutant protein.

WO 99/47608 discloses the introduction of articial amino acid substitutions into defined critical positions of the naturally occurring allergen while retaining the α-carbon backbone tertiary structure of the allergen.

WO 02/40676 discloses the introduction of at least 4 primary artificial amino acid substitutions into defined critical positions while retaining the α-carbon backbone tertiary structure of the allergen, wherein each primary mutation is spaced from another primary mutation by at least 15 Å and wherein at least one circular surface region with an area of 800 Å2 comprises no mutation.

J. Biomol. Struc. Dynamics (2000), vol. 17 pages 821-828 (Liang et al.) discloses transferring of a biological function of one protein to another by grafting the functional part of the protein to another appropriate scaffold protein. As a test system, the binding epitope of barstar, the inhibitor of barnase, is grafted onto a smaller molecule.

Protein Science (1994), vol. 3, p. 2351-2357 (Jin & Wells) discloses use of antigen-antibody complexes for studying protein-protein interactions. The binding of human growth hormone hGH to a monoclonal antibody (MAb 3) was studied. Five amino acids of hGH essential for the binding to MAb 3 was grafted onto a non-binding homologue of hGH, human placental lactogen (hPL), which has 86% sequence identity with hGH. Also, two additional framework mutations were introduced. The grafted hPL mutant bound to MAb 3 as well as hGH. Attempts to graft the epitope onto a scaffold protein having a homology with hGH of 23% were not successful.

J. Immunol (2001), vol. 166, p. 6057-6065 (King et al.) discloses hybrid insect venom allergens. The hybrids consist of an insertion of a small portion of the guest allergen of interest, Ves v 5, into a homologous host protein, Pol a 5. Ves v 5 and Pol a 5 have a sequence identity of 59% and a low degree of antigenic cross-reactivity. Hybrids are formed by inserting one portion of about 7 to about 50 amino acids into the allergen. The hybrids are useful for the mapping of B-cell epitope-containing regions of proteins and for use as immunotherapeutic reagents in man. This approach for generating allergen hybrids is however not appropriate for use in allergy vaccination strategies for the following reasons. Firstly, insertion of a peptide fragment from an insect allergen into an insect scaffold protein will in many cases lead to destabilization of the three-dimensional structure of the molecule. Unstable molecules are not suitable for use in vaccination. Secondly, as epitopes almost never consist of a single linear peptide fragment of the allergen, this approach is not suitable for "grafting" three-dimensional epitopes from allergens to scaffold proteins.

OBJECT OF THE INVENTION

The object of the invention is to provide new protein variants of naturally occurring allergens, said protein variants having properties useful in allergy vaccination. Accordingly, it is the aim of the current invention to generate protein variants of scaffold proteins for use as vaccine components, which resemble natural allergens with respect to the overall protein folding pattern and the contours of the surface topography, while at the same time having surface contours that have low or reduced IgE binding capability compared to the allergen. The purpose is to generate surface contours of the scaffold protein having similarity to the naturally occurring allergen in question, in order to enable stimulation of immune responses that will generate protective IgG antibodies with the ability to block IgE binding to the natural allergen and thereby alleviate or cure allergy symptoms.

Previous approaches for obtaining protein variants with improved performance in e.g. allergy vaccines have mainly focused on modification of the naturally occurring allergen in order to reduce IgE binding affinity. A major disadvantage of this approach is that by introducing an increasing number of mutations into the allergen, the risk of destabilizing the three-dimensional structure of the molecule is greatly increased and unstable molecules are certainly not attractive to use as therapeutic vaccine candidates.

The idea behind the present invention is to select a naturally occurring "scaffold protein" with sequence homologies to the natural allergen. The scaffold protein has a folding pattern that resembles that of the natural allergen while at the same time displaying substantially reduced antibody cross-reactivity. In this way it is ensured that the "starting material" is a stable molecule with correct three-dimensional folding pattern and with little or no binding to IgE antibodies specific to the naturally occurring allergen. Introduction of mutations in the scaffold protein, introducing or modulating or eliminating existing antibody binding surface contours or epitopes homologous to structures of the allergen, results in creation of stable protein variants, capable of raising a protective immune response and with a lowered risk of inducing side-effects, since the mutated scaffold protein variant exhibits a lower antibody reactivity compared to the natural allergen The invention is based on the recognition that it is possible to model partly or fully an epitope of an allergen on a scaffold protein, by substituting amino acids of the portion of the scaffold protein surface area corresponding to the epitope by amino acids located in the corresponding position in the primary amino acid sequence of the allergen. In particular, the invention is based on the recognition that even though most epitopes are discontinuous, it is nevertheless possible to create such epitopes fully or partly by selective and specific mutation of key surface amino acids of the epitopes situated at different positions of the primary amino acid sequence. Furthermore, the invention is based on the discovery that such mutated scaffold protein variants may be used in lieu of the native allergens for therapeutic and diagnostic purposes, and that such mutated scaffold proteins have modified properties for binding of antibodies and hence i.e. have the advantage of a reduced risk of inducing anaphylactic reactions when used as an allergy vaccine component.

A more efficient generation of a protective immune response can be achieved by using a mixture of different protein variants, thereby presenting the immune system to several different epitope areas, preferably without presenting more than one epitope area at the same molecule.

One aspect of the present invention comprises introduction of primary mutations in a defined, coherent surface area of up to about 5000 Å$^2$ in order to establish a surface area that mimics an epitope on the natural allergen. The surface area to be mutated is restricted to 5000 Å$^2$ for the purpose of allowing only a single antibody molecule to bind at a time thereby avoiding the risk of effector cell triggering in a vaccination scenario. Preferably, the scaffold protein has little or no measurable binding with allergen specific IgE antibodies and the resulting mutated allergen variant thus preferably only has the ability to bind one antibody molecule.

Another aim of the present invention comprises introduction of mutations for the purpose of establishing several surface areas that mimick allergen epitopes. Also, mutations may be introduced in order to reduce affinity of other surface areas with allergen specific IgE cross-reactivity. Several antibody molecules will thus in theory be able to bind to the mutated protein variant in question, but with greatly reduced affinities compared to binding of these antibodies to the natural allergen. The affinities of the IgE interactions should be reduced to a level limiting or abolishing the risk of triggering effector cell degranulation, while at the same time retaining the capacity to induce formation of protective antibodies reactive with the allergen in question.

B. Histamine release of rMal d1 and mutated rMal d 1 in comparison to rBet v1.2802. rBet v 1.2801 (●), rMal d 1 (2620) (■) or mutated rMal d 1 (2762) [◇] or (2781) [Δ]with 8 and 6 primary mutations, respectively.

Figure 9:
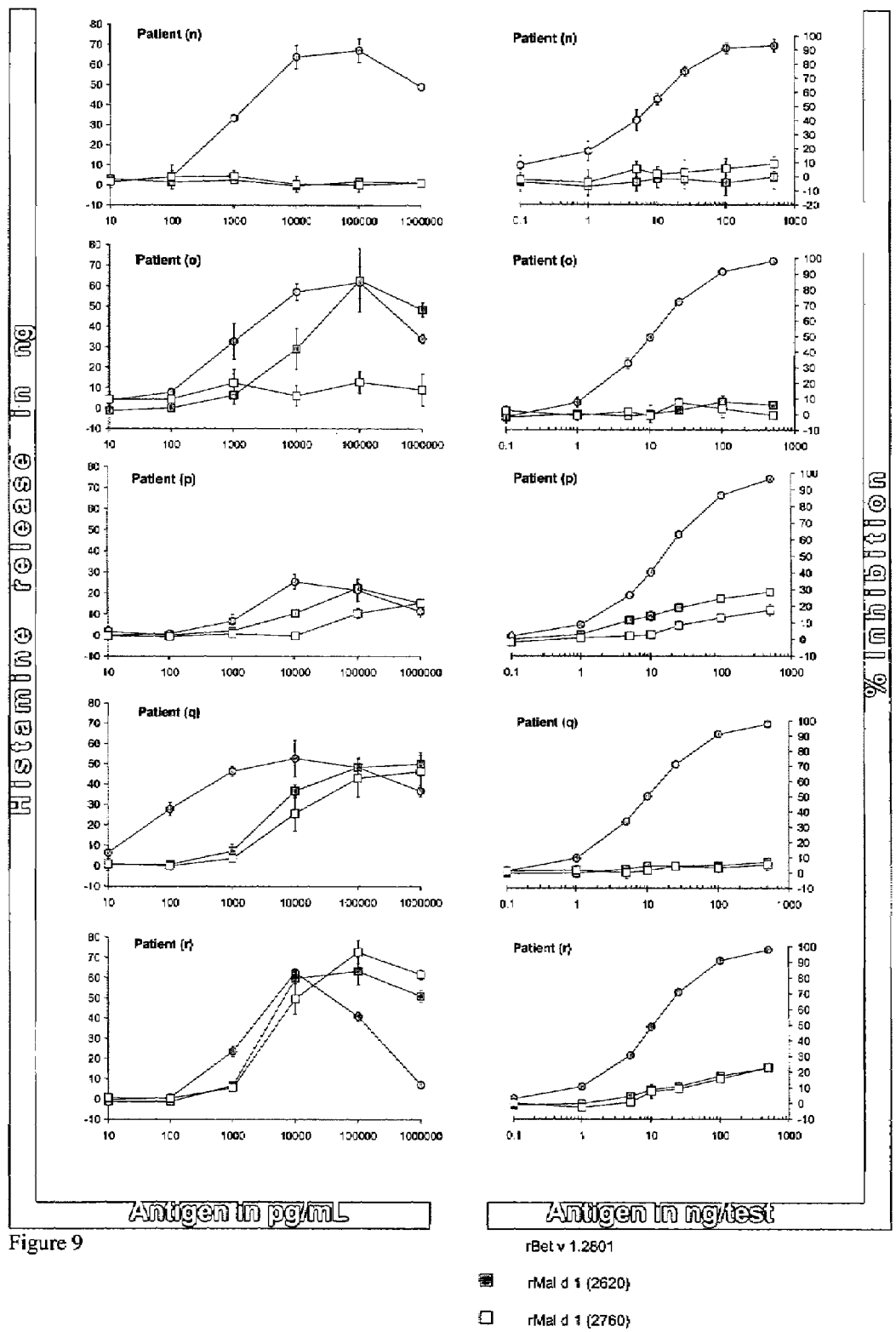

FIG. 9: The graphics show results from IgE-inhibition experiments (right) and histamine release experiments (left) with serum from 5 individual patients. Right side: inhibition curves of binding of human serum IgE to rBet v 1.2801 (●) for rMal d 1 (2620) (■) and mutated rMal d 1 2760 (□). Left side: histamine release of rMal d 1 and mutated rMal d 1 in comparison to rBet v 1.2801

Figure 10A:
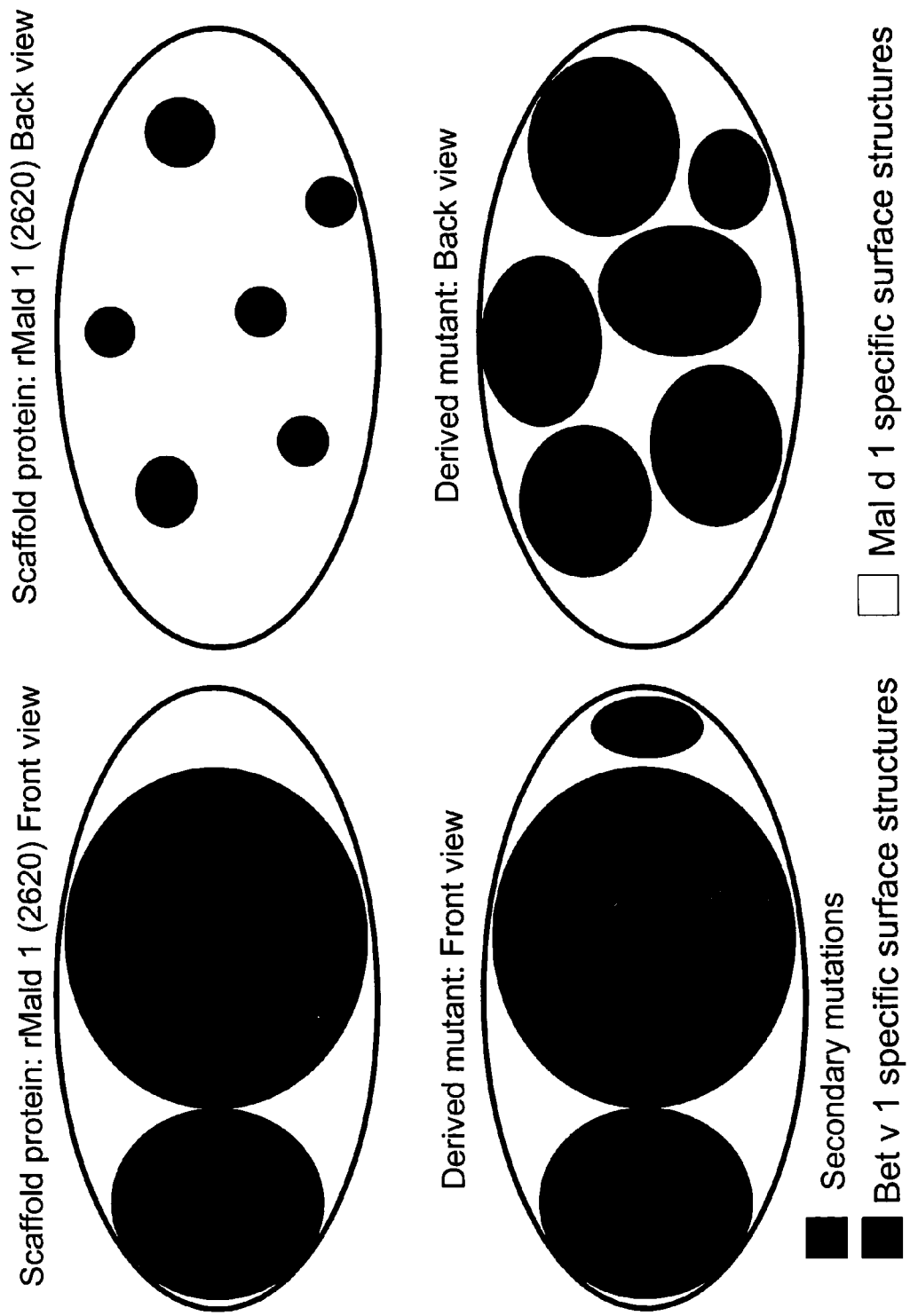

FIGS. 10A and B: Schematic illustration of a scaffold protein and a scaffold variant derived from the scaffold protein by introducing primary and secondary mutations.

FIGS. 11A, B and C: T-cell proliferative response to rMAL d 1 allergens of three individual patients: MCDS12 (A), GUA (B) and AHB21 (C).

Figure 11:
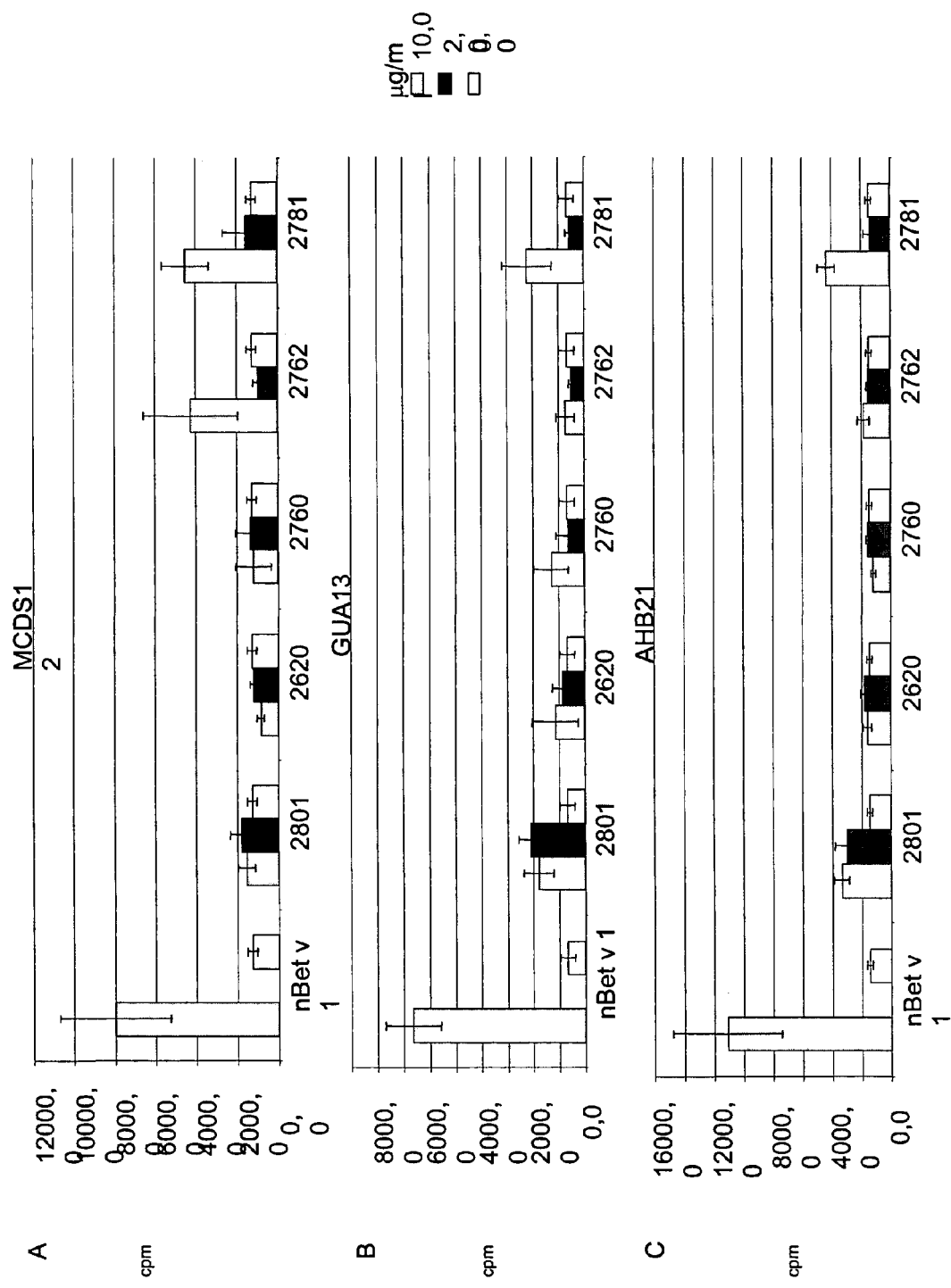
Figure 12:
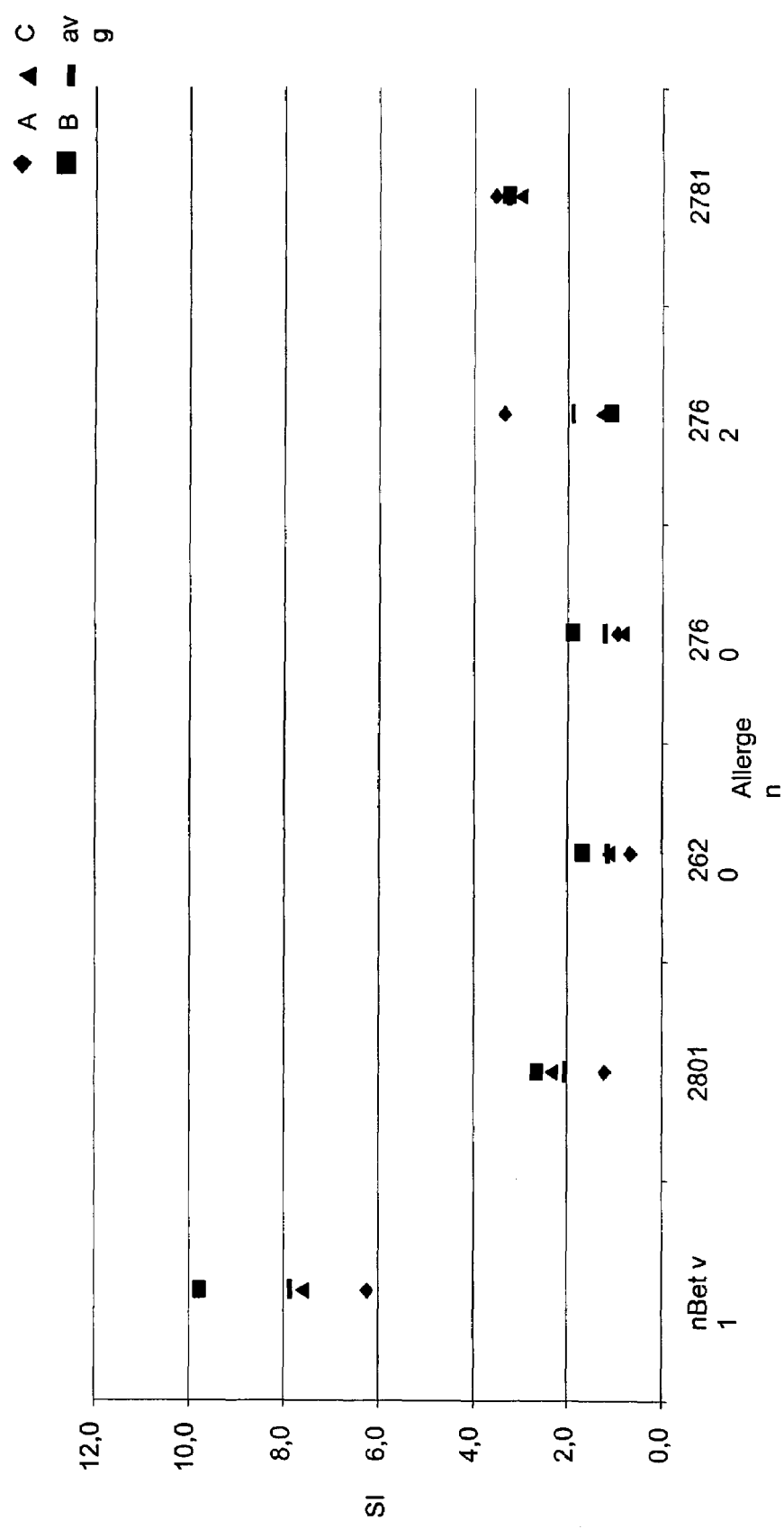

FIG. 12: T-cell stimulation index of the three patients in FIG. 11 (A, B, C).

Figure 13:
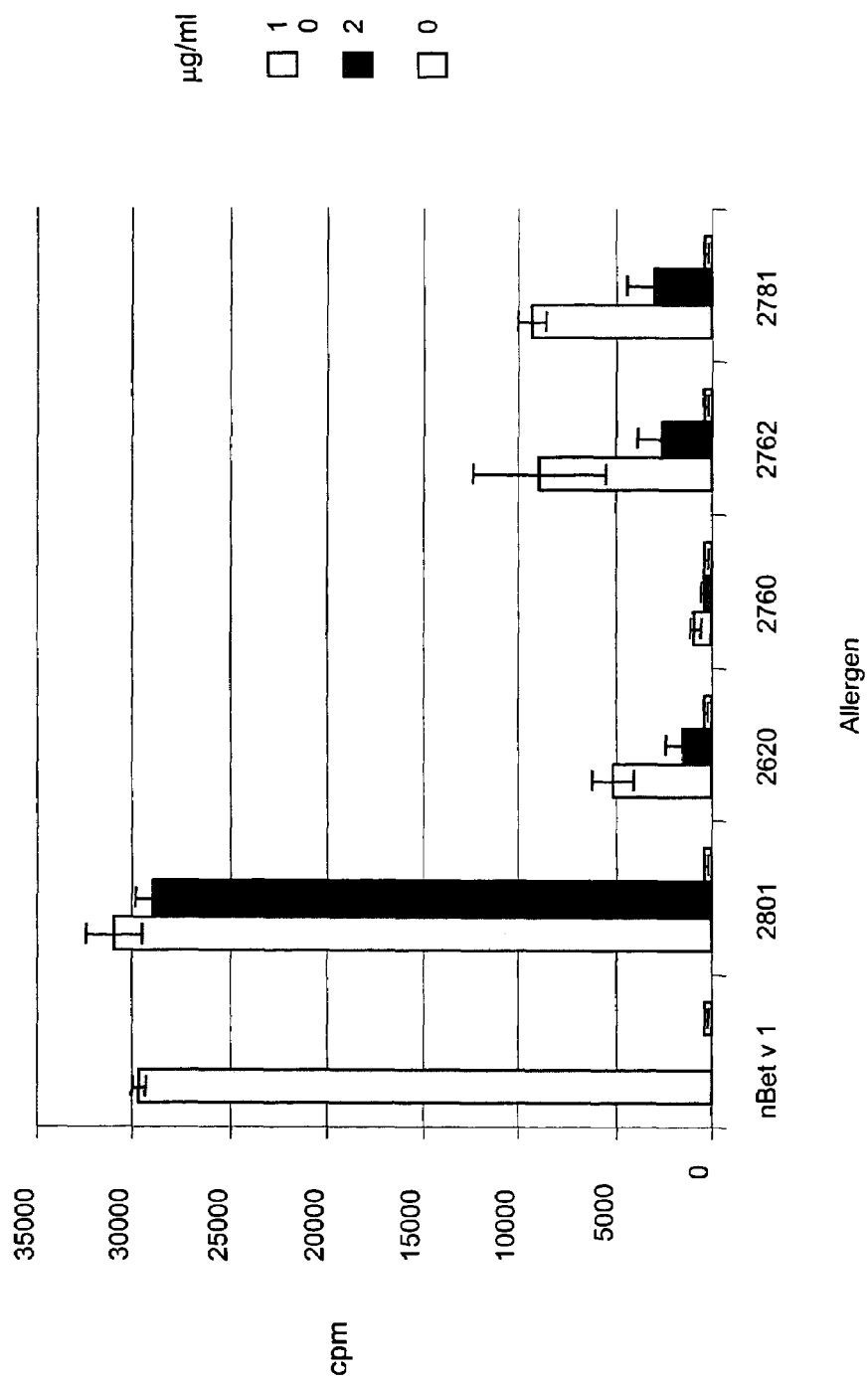

FIG. 13: T-cell proliferative response of Bet v 1 specific T-cell line.

Figure 14:
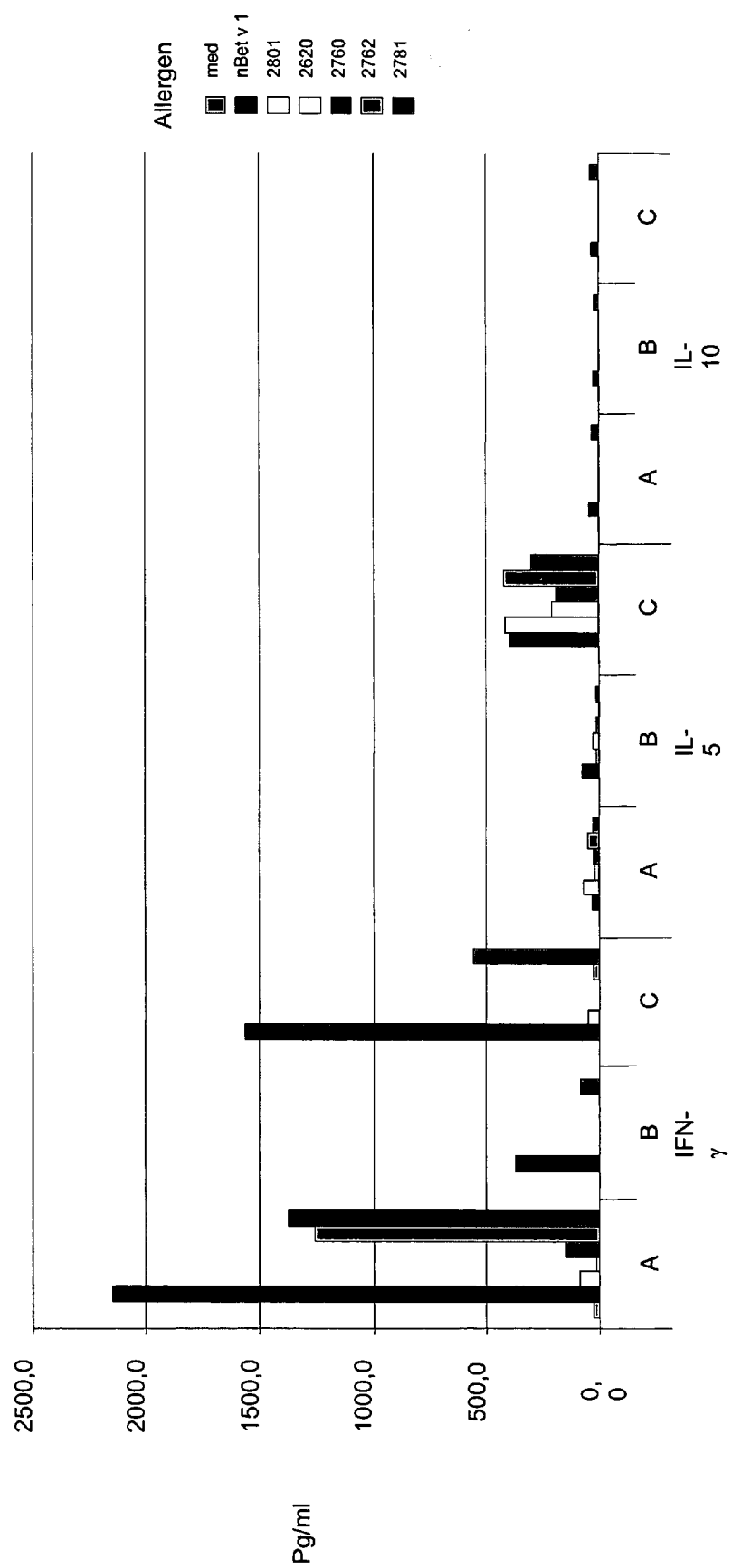

FIG. 14: Cytokine response to Mal d 1 allergens in PBL cultures.

Figure 15:
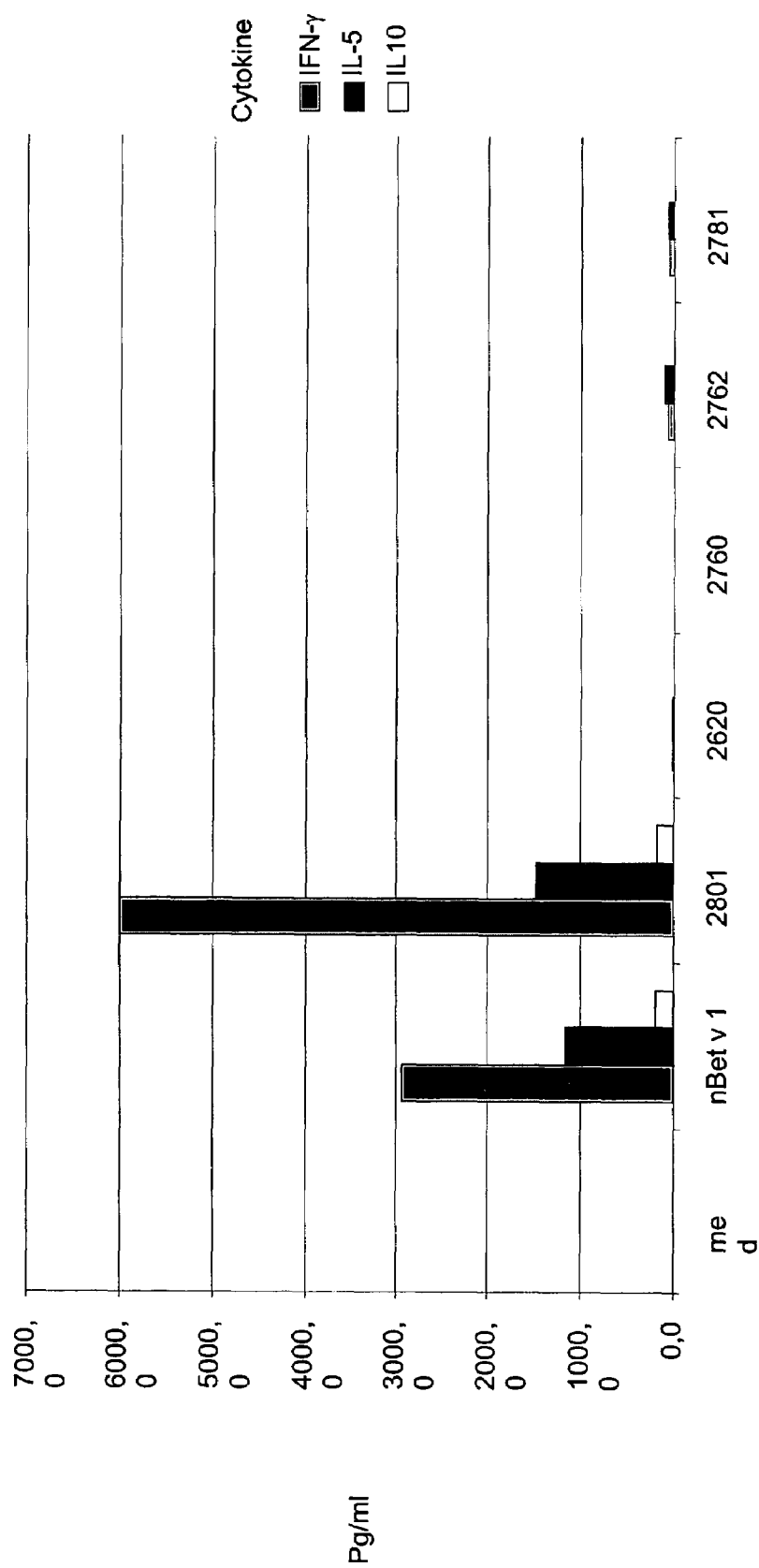

FIG. 15: Cytokine response to Mal d 1 allergens in Bet v1-specific T-cell lines.

Figure 16:
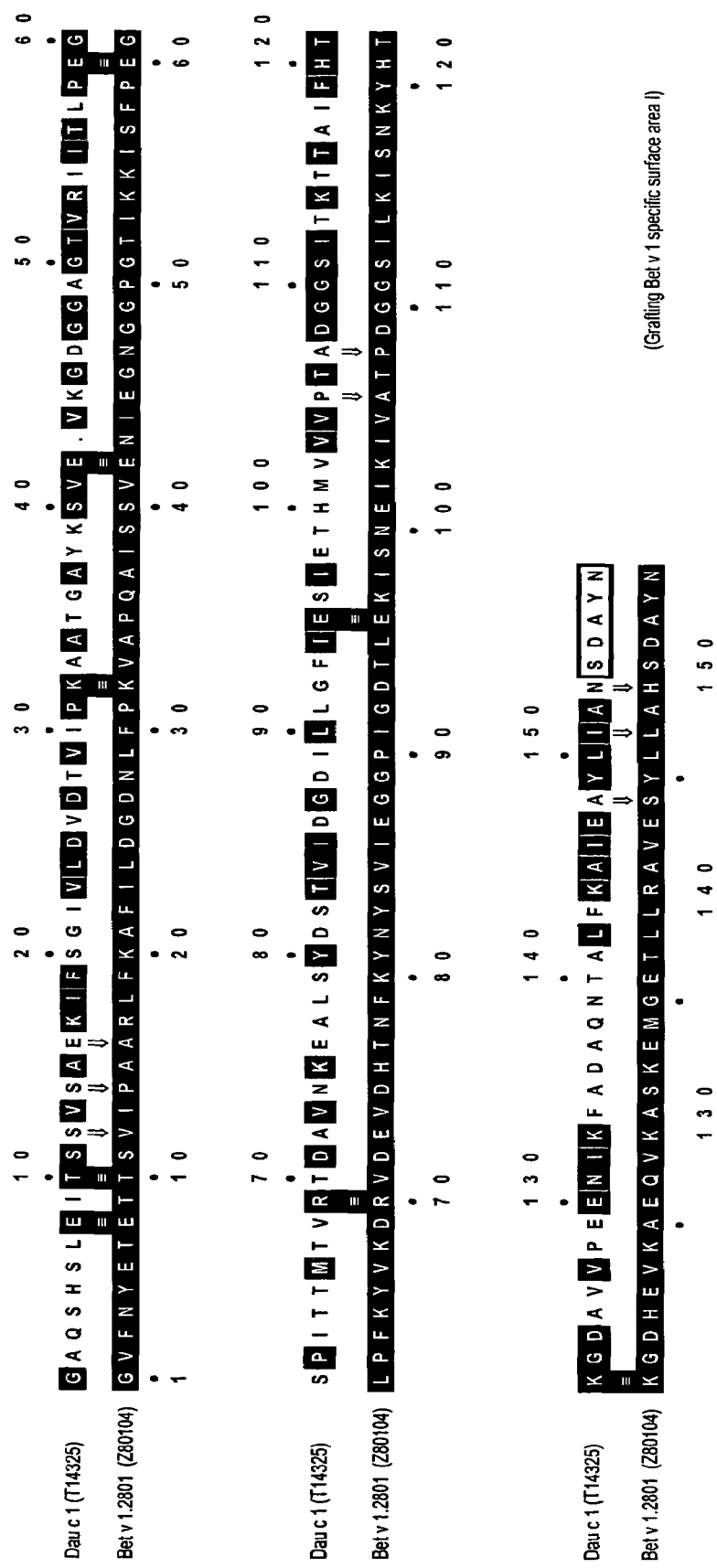

FIG. 16: Grafting Bet v 1 specific surface area I. Amino acid alignment of Dau c 1 and Bet v 1. Position no. above sequences refers to Dau c 1 (T14325) (SEQ ID NO: 4). Positions no. below sequences refers to Bet v 1 (z80104) (SEQ ID NO: 5). Black background shows positions in the polypeptide sequences having identical amino acid residues. Grey background shows positions in the polypeptide sequences having homologous amino acid residues. Amino acid positions that in example 1A are targeted for introduction of secondary mutations are indicated with triple bars on black background and amino acid positions for introduction of primary mutations are indicated with black arrows.

Figure 17:
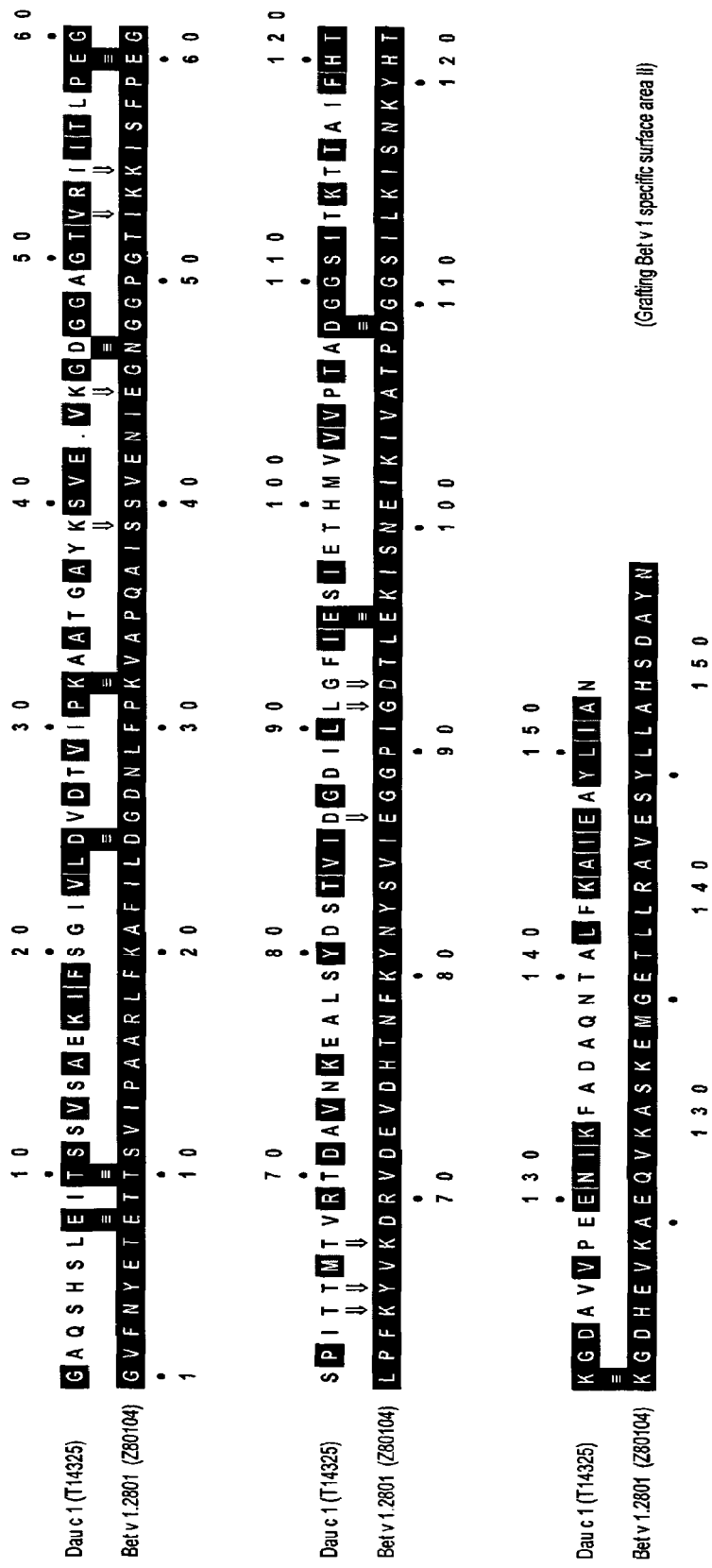

FIG. 17: Grafting Bet v 1 specific surface area II. Amino acid alignment of Dau c 1 and Bet v 1. Position no. above sequences refers to Dau c 1 (T14325) (SEQ ID NO: 6). Positions no. below sequences refers to Bet v 1 (z80104) (SEQ ID NO: 5). Black background shows positions in the polypeptide sequences having identical amino acid residues. Grey background shows positions in the polypeptide sequences having homologous amino acid residues. Amino acid positions that in example 1B are targeted for introduction of secondary mutations are indicated with triple bars on black background and amino acid positions for introduction of primary mutations are indicated with black arrows.

FIG. 18: Amino acid alignment of Lep d 2 and Der p 2. Position no. above sequences refers to Lep d 2 (S66499) (SEQ ID NO: 7). Positions no. below sequences refers to Der p 2 (P49278) (SEQ ID NO: 8). Black background shows positions in the polypeptide sequences having identical amino acid residues. Grey background shows positions in the polypeptide sequences having homologous amino acid residues. Amino acid positions that in example 2A are targeted for introduction of primary mutations are indicated with white arrows on black background. Amino acid positions that in example 2B are targeted for introduction of primary mutations are indicated with black arrows on white background. Amino acid positions suggested for introduction of secondary mutations in either example 2A or 2B are indicated with triple bars on black background.

FIG. 19: View of amino acid residue positions on Lep d 2: K6, S22, R30, K76, K81, V114 that are selected in example 2A as possible target positions for the introduction of secondary mutations. ABCD show molecular surfaces of Lep d 2 (accession no S66499) modeled at SWISS-MODEL using pdb entry 1ktj as template. A=front view, B=Turn 1 (front view turned 90° out of plane around the horizontal axes), C=Turn 2 (front view turned 180° out of plane around the horizontal axes), D=Turn 3 (front view turned 270° out of plane around the horizontal axes). Grey color shows α-carbon backbone atoms and side chain atoms on amino acid residues that are identical or homologous to Der p 2 specific amino acid residues in corresponding amino acid positions. White color shows amino acid residues that are specific for Lep d 2 (accession no S66499). Black color shows amino acid residues on Lep d 2 that in example 2A are selected as possible targets for the introduction of secondary mutations.

FIG. 20: View of amino acid residue positions on Lep d 2: D17, S19, Q32, K33, T35, N88, T92, A95, tat are selected in example 2A as possible target positions for the introduction of primary mutations. ABCD show molecular surfaces of Lep d 2 (accession no S66499) modeled at SWISS-MODEL using pdb entry 1 ktj as template. A=front view, B=Turn 1 (front view turned 90° out of plane around the horizontal axes), C=Turn 2 (front view turned 180° out of plane around the horizontal axes), D=Turn 3 (front view turned 2700 out of plane around the horizontal axes). Grey color shows .alpha.-carbon backbone atoms and side chain atoms on amino acid residues that are identical or homologous to Der p 2 specific amino acid residues in corresponding amino acid positions on Der p 2 (pdb entry 1 ktj). White color shows amino acid residues tat are specific for Lep d 2 (accession no s66499). Black color shows amino acid residues on Lep d 2 tat in example 2A are selected as possible targets for the introduction of primary mutations.

Figure 21:
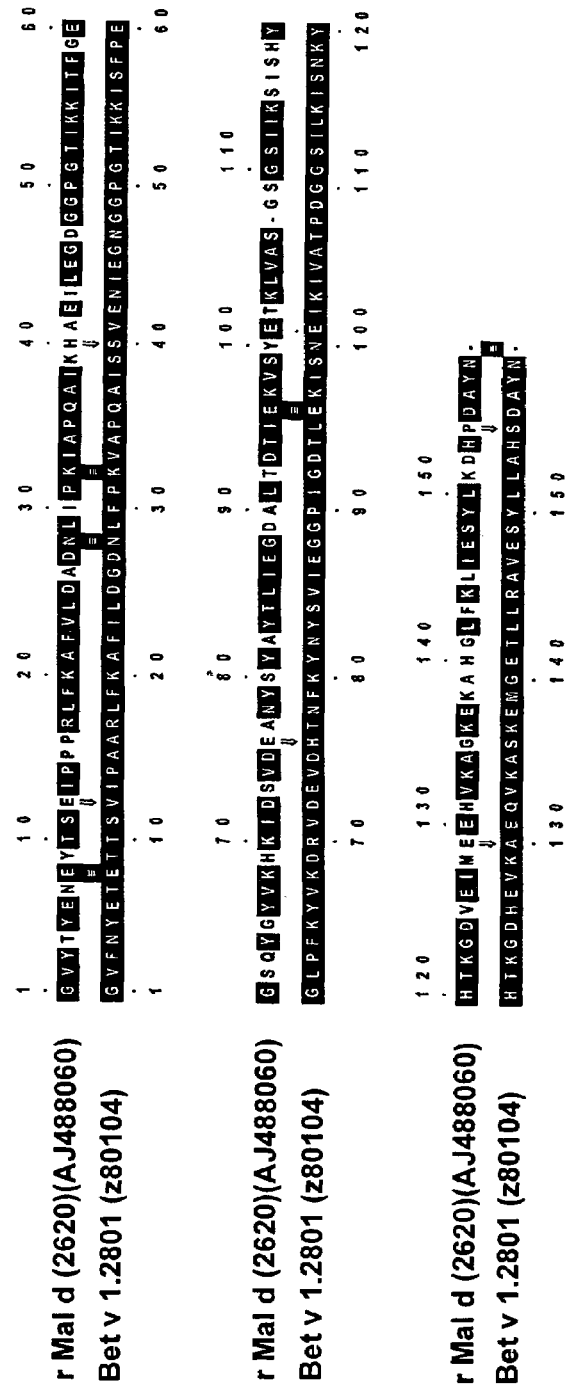

FIG. 21: Amino acid alignment of rMal d 1 (2620) and Bet v 1.2801. Position no. above sequences refers to Mal d 1 (accession no. AJ488060). Positions no. below sequences refers to Bet v 1 (accession no. Z80104). Black background shows positions in the polypeptide sequences having identical amino acid residues. Grey background shows positions in the polypeptide sequences having homologous amino acid residues. Amino acid positions that in example 3 are targeted for introduction of secondary mutations are indicated with triple bars on black background and amino acid positions for introduction of primary mutations are indicated with black arrows.

FIG. 22: Amino acid alignment of Gly d 2 and Der p 2. Position no. above sequences refers to Gly d 2 (AJ272216) (SEQ ID NO: 10). Positions no. below sequences refers to Der p 2 (P49278) (SEQ ID NO: 8). Black background shows positions in the polypeptide sequences having identical amino acid residues. Grey background shows positions in the polypeptide sequences having homologous amino acid residues. Amino acid positions that in example 4 are targeted for introduction of secondary mutations are indicated with triple bars on black background and amino acid positions for introduction of primary mutations are indicated with black arrows.

FIG. 23: View of amino acid residue positions on Gly d 2 that are selected in example 4 as possible target positions for the introduction of secondary mutations. ABCD show molecular surfaces of Gly d 2 (accession no. AJ272216) modeled at SWISS-MODEL using pdb entry 1 ktj as template. A=front view, B=Turn 1 (front view turned 90° out of plane round the horizontal axes), C=Turn 2 (front view turned 180° out of plane around the horizontal axes), D=Turn 3 (front view turned 270° out of plane around the horizontal axes). Grey color shows .alpha.-carbon backbone atoms and side chain atoms on amino acid residues that are identical or homologous to Der p 2 specific amino acid residues in corresponding amino acid positions on Der p 2 (pdb entry 1 ktj). White color shows amino acid residues that are specific for Gly d 2 (accession no. AJ272216). Black color shows amino acid residues on Gly d 2 that in example 4 are selected as possible targets for the introduction of secondary mutations.

FIG. 24: View of amino acid residue positions on Gly d 2 that are selected in example 4 as possible target positions for the introduction of primary mutations. ABCD show molecular surfaces of Gly d 2 (accession no. AJ272216) modeled at SWISS-MODEL using pdb entry 1 ktj as template. A=front view, B=Turn 1 (front view turned 90° out of plane around the horizontal axes), C=Turn 2 (front view turned 180° out of plane around the horizontal axes), D=Turn 3 (front view turned 270° out of plane around the horizontal axes). Grey color shows .alpha.-carbon backbone atoms and side chain atoms on amino acid residues that are identical or homologous to Der p 2 specific amino acid residues in corresponding amino acid positions on Der p 2 (pdb entry 1 ktj). White color show amino acid residues that are specific for Gly d 2 (accession no. AJ272216). Black color shows amino acid residues on Gly d 2 that in example 4 are selected as possible targets for the introduction of primary mutations.

Figure 25:
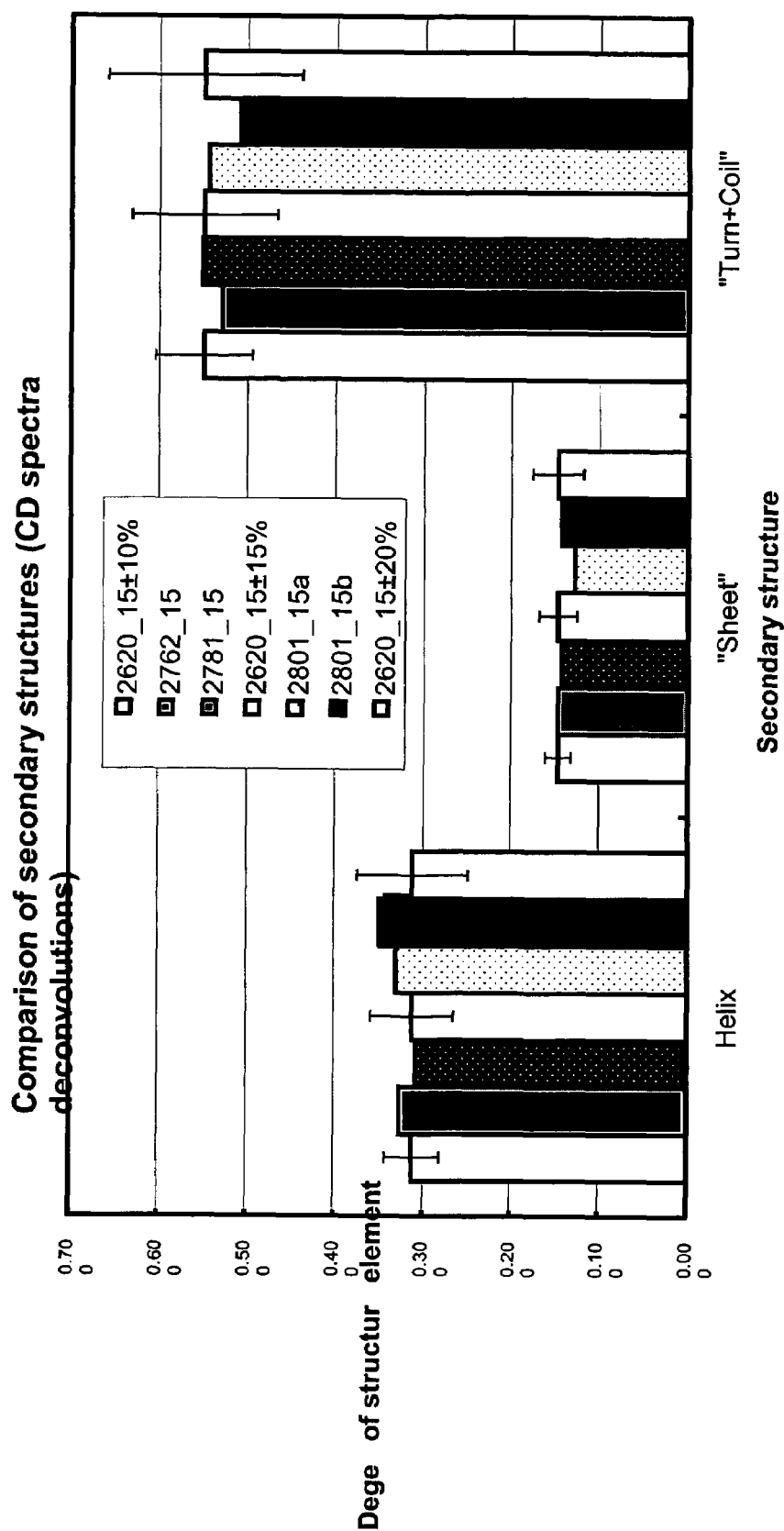

FIG. 25: Composition in secondary structure elements of rMal d 1 (2620), rMal d 1 (2762), rMal d 1 (2781) and Bet v 1.2801, obtained by the deconvolution of their CD spectra. The deconvolution sets of rMal d 1 (2762), rMal d 1 (2781) and Bet v 1.2801 fall within the acceptance boundaries determined for the reference protein, rMal d 1 (2620) (±15%), and therefore these four proteins may be considered to be structurally similar with respect to secondary structure.

Figure 26:
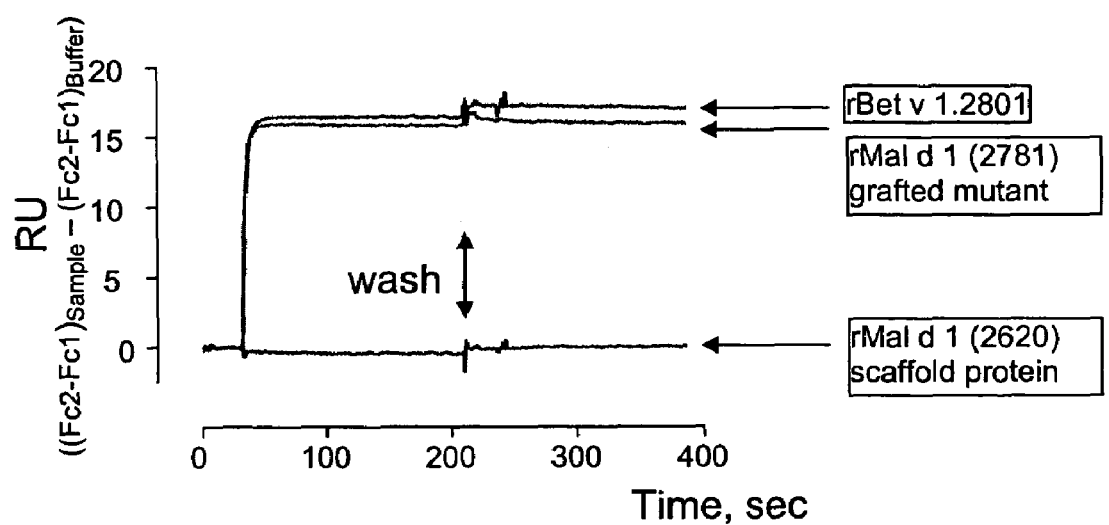

FIG. 26: Biacore experiment. Binding of the monoclonal antibody BV16 to rBet v 1.2801, non-mutated rMal d 1 (2620) and mutated rMal d 1 (2781). No binding was observed with non-mutated rMal d 1 (2620). rBet v 1.2801 and mutated rMal d 1 (2781) are both bound by BV16.

SUMMARY OF THE INVENTION

The present invention relates to a recombinant protein variant with the ability to induce a protective immune response to a naturally occurring allergen, wherein the protein variant is a variant of a scaffold protein, said scaffold protein having a three-dimensional folding pattern that is structurally similar to that of the naturally occurring allergen, compared to the scaffold protein, comprises two or more primary mutations spaced by at least one non-mutated amino acid residue, each primary mutation introducing into the scaffold protein at least one amino acid residue identical or homologous to the corresponding amino acid residue or residues in the naturally occurring allergen, and has, compared to the scaffold protein, an increased affinity and/or binding capacity to IgE antibodies that are specific to the naturally occurring allergen.

The present invention furthermore relates to the use of one or more protein variants for preparing a pharmaceutical composition for treatment of allergic individuals.

The present invention also relates to DNA sequences encoding protein variants according to the present invention as well as to vectors and host-cells hosting such DNA sequences and methods of producing recombinant proteins.

Also, the present invention relates to diagnostic assays.

DETAILED DESCRIPTION OF THE INVENTION

The idea of the present invention is to use a "scaffold protein" with a similar three-dimensional folding pattern but with little or no antibody cross-reactivity with a naturally occurring allergen as the basis for creating novel allergen mutants.

This scaffold protein can be used for creating novel recombinant protein variants that possess surface areas with and without antibody cross-reactivity with the allergen specific antibodies. There are several important advantages by using the scaffold protein as the basis for creating allergen vaccine candidates. It is usually required to perform a large number of mutations of an allergen in order to lower its allergen specific IgE reactivity and thereby the risk of inducing adverse effects during vaccination. Also, as a large number of mutations tend to destabilize the protein, these mutated allergens are often not suitable for use as vaccine candidates. The idea behind the invention is thus that a relatively small number of mutations are generally required in order to partly or fully establish allergen specific IgE recognizing contours on the surface of an appropriate scaffold protein. Such molecules have the potential of inducing new protective immune responses that can compete with IgE binding upon allergen exposure leading to a reduced risk of inducing IgE-mediated allergic responses.

One aspect of the invention is to generate a mutated protein variant with one allergen homologous surface area. A preferred scaffold protein according to this aspect is a scaffold with little or no binding to IgE antibodies specific to the naturally occurring allergen as a stating point thereby minimizing the need for introduction of secondary mutations. A scaffold with some binding to to allergen specific antibodies may also be suitable. Introduction of one or more secondary mutations in such a scaffold protein may limit or eliminate potential cross-reactivity. The ability of scaffold proteins and scaffold protein variants to bind antibodies specific to the naturally occurring allergen can be tested by RAST inhibition using a panel of sera from patients allergic to the allergen in question (Nolte et al (1987) Allergy, 42:366-373). Devoid in antibody binding means a reduction in antibody affinity by a factor of $10^3$, more preferably $10^4$, most preferably $10^5$ or more.

Comparison of structural similarities between the scaffold protein and the allergen in question includes assessment of three-dimensional structures and/or amino acid sequence. Folding pattern similarity is preferably assessed by comparison of scaffold and allergen three-dimensional structures. In absence of a known three-dimensional structure of the scaffold protein and/or the naturally occurring allergen, proteins having sequence identity greater than 10%, preferably greater than 20% to the allergen can in general be anticipated to have homologous folding patterns and thus be applied as scaffold proteins. However, even protein with amino acid identity less than 10% (exemplified by accession no. AAH05642 and pdb entry 1jss) have been known to have the same folding pattern as the allergen to which is compared e.g. in this case Bet v 1.

The three-dimensional structure of the scaffold protein may also be modeled based on the known structure of the allergen in question, or vice versa. More preferably amino acid sequence identity between the scaffold molecule and the allergen in question should be below 67%, more preferably between 20 and 60%, more preferably between 20 and 50%, and even more preferable 30-50%.

A number of amino acids on the molecular surface of the scaffold molecule are identical with amino acids on the surface of the allergen in question, and positioned in corresponding positions in the homologous structure. This can be visualized by comparison of the three-dimensional models or predicted three-dimensional structures.

A surface area is selected for "epitope grafting", preferentially an area comprising as many identically positioned amino acid residues in the scaffold and the allergen respectively as possible. The number of artificial mutations needed to fully or partly establish a surface area that mimics an allergen on the surface of the scaffold protein is thereby minimized. Preferably, the generated surface area comprises between 1000 and 3600 Å$^2$, and not larger than 5000 Å$^2$. It has been estimated that around 2000 Å$^2$ is masked upon binding by the CDR region alone. Furthermore there will be steric hindrance caused by the presence of the entire antibody. Thus, an area of up to 5000 Å$^2$ is therefore inaccessible to binding by other antibody molecules.

Within the selected area of the scaffold protein, surface amino acids that are different between the scaffold protein and the allergen in question are mutated in such a way that most or preferably all of the surface exposed amino acid residues within the selected area become homologous, or identical to surface exposed amino acids of the allergen in question.

In a further aspect surface areas may be modified to become less identical or homologous to the allergen surface in order to avoid cross-reaction to these surfaces of allergen specific antibodies. In such surface areas, amino acid residues that are identical or homologous to amino acid residues in the corresponding position of the allergen are substituted by residues that are different or less homologous.

The three-dimensional structure of the resulting mutated scaffold protein, i.e. the recombinant protein variant may be verified with respect to its overall folding pattern as well as the conformation of the "grafted" epitope area. Methods of determining secondary and tertiary structures of a protein include X-ray crystallography, NMR spectroscopy, and circular dichroism spectroscopy. The stability of the resulting mutated molecule may be assessed by circular dichroism spectroscopy applying a range of variations in urea concentration, pH, ion strength, temperature, or other parameters.

In a vaccination scenario, protein variants or preferentially a mixture of protein variants with non-overlapping allergen specific surface areas, are expected to be safe, since two IgE antibodies specific for the allergen in question preferably cannot bind simultaneously, and hence do not trigger allergic reactions. Furthermore they are expected to be efficient in stimulating protective IgG antibody responses, wherein the IgGs are reactive with the natural allergen in question, within surface areas covered by the allergen specific surface areas.

According to the other aspect of the invention, mutated protein variant with several grafted areas distributed over parts of or the entire molecule are generated. Scaffold proteins may be mutated so as to reduce or increase antibody binding affinity or both, thereby eliminating fully or partly epitope areas and/or establishing epitopes areas on other parts of the scaffold protein. The idea is to achieve a general low affinity interaction over the entire surface with respect to binding of allergen specific IgE antibodies.

A number of amino acid residues on the surface of the scaffold protein are identical with amino acid residues on the surface of the allergen in question. This can be visualized by comparison of the three-dimensional structures of the allergen and the scaffold protein.

The surface areas that are selected for reducing IgE affinity of the scaffold protein are coherent surface areas comprising amino acid residues that are homologous or identical between the allergen and the scaffold protein. Such amino acid residues are then mutated to amino acid residues that are related or non-related to amino acid residues in the allergen in question.

In surface areas that are selected for increasing the allergen specific antibody cross-reactivity of the protein variant, surface amino acid residues, which are different comparing the scaffold molecule and the allergen are selected. These amino acid residues are then mutated to amino acids that are homologous, or more preferably identical, with the allergen in question.

The surface of a recombinant protein variant(-s) comprises areas of amino acids that are identical as well as areas of amino acids that are non-identical with the allergen in question. When the surface of the recombinant protein variant is graphically represented, it can be visualized that the surface comprises at least one essentially circular area that is homologous or identical with the corresponding area of the naturally occurring allergen. This area covers about 300-900 Å$^2$, more preferably 500-800 Å$^2$, and most preferably 500-600 Å$^2$.

Accordingly, preferably the scaffold protein does not have any immunogenic reactivity with naturally occurring allergen specific antibodies. However, it is possible to use a scaffold protein having reactivity with natural occurring allergen specific antibodies, in which case preferable one or more of the epitopes are modified in order to eliminate or decrease the antibody binding affinity of these epitopes.

In other words, the main aspect of the present invention relates to a recombinant protein variant with the ability to induce a protective immune response to a naturally occurring allergen, wherein the protein variant is a variant of a scaffold protein, said scaffold protein has a three-dimensional folding pattern that is structurally similar to that of the naturally occurring allergen, compared to the scaffold protein, comprises two or more primary mutations spaced by at least one non-mutated amino acid residue, each primary mutation introducing into the scaffold protein at least one amino acid residue identical or homologous to the corresponding amino acid residue or residues in the naturally occurring allergen, and has, compared to the scaffold protein, an increased affinity and/or binding capacity to IgE antibodies that are specific to the naturally occurring allergen.

A primary mutation according to the present invention might comprise a substitution a deletion and/or an addition. According to the invention, 2-50, preferably 2-40, more preferably 3-25, more preferably 4-15 and most preferably 5-12 primary mutations are performed. It is a very important aspect of the present invention that at least two primary mutations are performed, ensuring that three-dimensional epitope areas are established that can bind allergen specific antibodies are grafted onto the scaffold molecule.

The present invention furthermore comprises protein variants with one or more secondary mutations introducing into the scaffold protein amino acid residues, which are not present in the corresponding position in the natural occurring allergen. The purpose of introducing secondary mutations may e.g. be to stabilize the three-dimensional folding pattern of the protein variant or to decrease allergen specific IgE cross-reactivity.

According to the invention, 0-20, preferably 1-10, or most preferably 2-5 secondary mutations are performed.

In general, secondary mutations according to the present invention may be performed as a mutation of one or more amino acid residues with any amino acid residue that is not present in the particular position in either the scaffold protein or the naturally occurring allergen. Preferably the secondary mutation is a substitution of an amino acid residue that is not present in the naturally occurring allergen but is homologous to the scaffold amino acid in order to minimize the risk of destabilizing the protein variant.

A primary or secondary mutation according to the present invention may comprise mutations carried out by site-directed mutagenesis (insertion, deletion or substitution), DNA shuffling, and/or by gene library methods.

Any primary or secondary mutation according to the invention may consist of a number of consecutively mutated amino acids. 1-15, preferably 1-10 and most preferably 1-5 consecutive amino acids are mutated in a primary or secondary mutation according to the present invention. In many cases the surface exposed amino acids that are part of an epitope area are present as single amino acid "points" within the primary structure of an allergen. In such cases it is usually sufficient to point mutate such amino acids. However, in other cases it is necessary to mutate several consecutive amino acids in order to increase or decrease antibody binding affinity.

An aspect of the invention comprises a method of producing a recombinant protein variant with the ability to induce a protective immune response to a naturally occurring allergen, comprising the steps of:
  selecting a scaffold protein, said scaffold protein having a three-dimensional folding pattern that is structurally similar to that of the naturally occurring allergen,
  introducing two or more primary mutations, that are spaced by at least one non-mutated amino acid residue, into the scaffold protein, each primary mutation introducing into the scaffold protein at least one amino acid residue identical or homologous to the corresponding amino acid residue or residues in the naturally occurring allergen, and
  thereby producing a protein variant that has, compared to the scaffold protein, an increased affinity and/or binding capacity to IgE antibodies that are specific to the naturally occurring allergen.

A product obtainable by the above method is also included within the scope of the present invention.

In one embodiment, a protein variant according to the present invention compared with the scaffold protein has an increased binding capacity with respect to antibodies specific to the naturally occurring allergen. Said binding capacity is preferably increased to at least 10%, preferably to at least 50%, and up to 100% of the antibody binding capacity of the natural allergen. Said protein variant furthermore preferably has a reduced ability to induce histamine release compared to the naturally occurring allergen. The reduction in histamine release potential of the protein variant is preferably reduced by 2 fold, more preferably by 10 fold, even more preferably by 100 fold, even more preferably by 1000 fold and most preferably by a 10,000 fold or more reduction compared with the ability of the naturally occurring allergen.

By ensuring that the ability of the protein variant to induce histamine release is greatly reduced i.a. the ability of the variant to cross-link the IgE receptor the protein variant thus constitutes a more safe alternative to the natural allergen as the active component of an allergen vaccine, since the ability to cause histamine release is largely associated with and responsible for adverse effects associated with the immediate type allergy response and allergy vaccination.

According to a second embodiment, a protein variant according to the present invention has a three-dimensional folding pattern or α-carbon backbone tertiary structure that closely resembles that of the scaffold protein as measured as described in Example 4. The surface contour making up an epitope is supported by the folding pattern of the peptide α-carbon backbone.

According to a preferred embodiment a protein variant according to the invention is therefore preferably derived from a scaffold protein that has a level of amino acid identity with the naturally occurring allergen of between 20 and 60%, preferably between 30 and 50%.

According to a third embodiment, a protein variant according to the present invention has all the primary mutations located in a surface region having an area of about 600-900 Å$^2$ so as to ensure that the primary mutations constitute an epitope area that can be recognized by the complementarity determining region of an allergen specific antibody. Furthermore, a protein variant according to the invention preferably comprises primary mutations of surface-exposed amino acids. A surface exposed amino acid has a solvent accessibility of above 20%, preferably above 30%, more preferably above 40%, and most preferably above 50%.

According to a fourth embodiment of the present invention, the naturally occurring allergen is an inhalation allergen, preferably originating from the taxonomic order of Fagales, Oleales or Pinales, and most preferably Bet v 1 (database accession number: Z80104). A preferred Bet v 1 scaffold protein is Mal d 1.

In other preferred embodiments, scaffold proteins of the major birch pollen allergen Bet v 1 are e.g. isoforms of Aln g 1 (alder) exemplified by accession number S50892, isoforms of Car b 1 (hornbeam) exemplified by Q96382, Q96381, CAA47367, Q96377, Q96378, Q96379, Q96503, Q96501, CAA47366, Q96380, isoforms of Fag s 1 (beech) exemplified by AJ130889, isoforms of Cas s 1 [*Castanea sativa*] exemplified by AJ417550, isoforms of Mal d 1 (apple) exemplified by accession numbers AJ488060, Q43550, Q43551, Q43552, Q43549, AAK13027, AAK13028, Q40280, AAD13683, Q9SYV2, Q9SYV3, Q9SYV4, Q9SYV6, Q9SYV9, Q9SYW3, Q9SYV5, AAK13029, Q9SYV7, Q9SYV8, JC4276, S51119, isoforms of Pru av 1 (cherry) exemplified by accession numbers O22521 O24248, O50001 and gi13787043, isoforms of Pyr c 1 (pear) exemplified by accession numbers AF057030, isoforms of Api g 1 (celery) exemplified by accession numbers p49372, p92918, isoforms of Dau c 1 (carrot) exemplified by accession numbers 004298, t14322, t14325, isoforms of Lupin exemplified by accession number p52779 (pdb entry 1IFV_A), isoforms of other Patogenesis Related proteins exemplified by accession numbers CAA10719, S20517, P93333, AB17_PEA, AB18_PEA, T14817 and other proteins that contains the same arrangement of secondary structure elements exemplified by accession number AAH05642 (pdb entry 1jss).

In an embodiment, where rMal d 1 (2620) (database accession number: AJ488060) is the Bet v 1 scaffold protein, a protein variant comprises at least two primary mutations selected from the group consisting of: (E12V, E12I, E12M, E12L), P16A, (H40S, H40T), I43N, L44I, D47N, G65K, K70R, (E76H, E76R, E76K, E76Q), S107T, G108P, +109D, S110G, E129A, K152L, (P154S, P154T), P155S and optionally one or more secondary mutations are selected from the group consisting of: N28X, preferably N28T, K32X, preferably K32Q, E45S, E96X, +159X. In this context, as well as in the following examples, the first letter and number corresponds to the original amino acid code in a particular amino acid position. The following letter is the amino acid that can be substituted with the original amino acid. Parenthesis means that there are a number of different options when choosing to mutate in a given amino acid position. One of these can be chosen.

In a specific embodiment, a Mal d 1 protein variant (rMal d 1 (2760)) comprises the sequence defined in SEQ ID NO 1:

GVYTYENEYTSEIPPPRLFKAFVLDADTLIPQIAPQAIKHAEILSGDGGP

GTIKKITFGEGSQYGYVKHKIDSVDEANYSYAYTLIEGDALTDTIEKVSY

ETKLVASGSGSIIKSISHYHTKGDVEIMEEHVKAGKEKAHGLFKLIESYL

KDHPDAYN, said variant comprising the following secondary mutations: N28T, K32Q, E45S. The rMal d 1 (2760) variant is an example of a scaffold protein according to the present invention that comprises a number of secondary mutations that together decrease the Bet v 1 specific IgE reactivity of the scaffold protein, as illustrated in detail in the examples.

In another specific embodiment, a protein variant of a Mal d 1 protein variant (rMal d 1 (2781)) comprises the sequence defined in SEQ ID NO 2:

GVYTYENEYTSEIPPPRLFKAFVLDADNLIPKIAPQAIKHAENIEGNGGP

GTIKKITFGEGSQYKYVKHRIDSVDHANYSYAYTLIEGDALTDTIEKVSY

ETKLVASGSGSIIKSISHYHTKGDVEIMEEHVKAGKEKAHGLFKLIESYL

KDHPDAYN, said variant comprising the following primary mutations: I43N, L44I, D47N, G65K, K70R, E76Q. The rMal d 1 (2781) variant is an example of a protein variant according to the present invention that has increased Bet v 1 specific IgE reactivity in comparison with the "native" rMal d 1 2620. This is illustrated in detail in the Examples.

In yet another specific embodiment, a protein variant of a Mal d 1 protein variant (rMal d 1 (2762)) comprises the sequence as defined in SEQ ID NO 3:

GVYTYENEYTSVIPPARLFKAFVLDADNLIPKIAPQAIKHAEILEGDGGP

GTIKKITFGEGSQYGYVKHKIDSVDEANYSYAYTLIEGDALTDTIEKVSY

ETKLVATPDGGSIIKSISHYHTKGDVEIMEEHVKAGKEKAHGLFKLIESY

LLDHSDAYN, said variant comprising the following mutations: E12V, P16A, K152L, P155S, S107T, G108P, +109D, S110G. "+" means in this context insertion of an amino acid at the indicated position. The rMal d 1 (2762) variant is an example of a protein variant according to the present invention that has increased Bet v 1 specific IgE reactivity in comparison with the "native" rMal d 1. This is illustrated in detail in the Examples.

In an embodiment demonstrating that a protein variant of Mal d 1 may comprise both primary and secondary mutations, such a protein variant comprises at least two primary mutations selected from the group consisting of: (E12V, E12I, E12M, E12L), (H40S, H40T), (E76H, E76R, E76K), E129A, (P154S, P154T), and optionally one or more secondary mutations selected from the group consisting of: E8X, N28X, K32X, E96X, +159X.

According to a fifth embodiment a protein variant of the present invention is a protein variant wherein Dau c 1 (database accession number: T14325) is a scaffold protein of Bet v 1. According to this embodiment, a protein variant of Dau c 1 comprises at least two primary mutations selected from the group consisting of: (S12V, S12L, S12I, S12M), S14P, E16A, P105A, A107P, (A148S, A148T), (I151L, I151V, I151M), (N153H, N153K, N153R), (+154S, +154T), (+155D, +155E), +156A, (+157Y, +157F), (+158N, +158Q), (K39S, K39T), (K44E, K44D), (V52I, V52M, V52L), (I54K, I54R, I54H), (T64K, T64R, T64H), (T65Y, T65F, T65W), (T67K, T67R, T67H), D86E, L91G, (G92D, G92E) and optionally one or more secondary mutations are selected from the group consisting of: K32X, E42X, E59X, R69X, E95X, K122X, E8X, T10X, D25X, D46X, D108X.

In a specific embodiment, a Dau c 1 protein variant comprises at least two primary mutations selected from the group consisting of: (S12V, S12L, S12I, S12M), S14P, E16A, P105A, A107P, (A148S, A148T), (I151L, I151V, I151M), (N153H, N153K, N153R), (+154S, +154T), (+155D, +155E), +156A, (+157Y, +157F), (+158N, +158Q) and optionally one or more secondary mutations selected from the groups consisting of: K32X, E42X, E59X, R69X, E95X, K122X. This embodiment is a demonstration of establishment of a single epitope area on the surface of a scaffold protein while other areas have been mutated so as to decrease antibody affinity.

In another specific embodiment, a Dau c 1 variant comprises comprises at least two primary mutations selected from the group consisting of: (K39S, K39T), (K44E, K44D), (V52I, V52M, V52L), (I54K, I54R, I54H), (T64K, T64R, T64H), (T65Y, T65F, T65W), (T67K, T67R, T67H), D86E, L91G, (G92D, G92E) and optionally at least one secondary mutation is selected from the group consisting of: E8X, T10X, D25X, K32X, D46X, E59X, E95X, D108X, K122X. This embodiment is another example of establishment of a single epitope area on the surface of a scaffold protein and decrease of antibody affinity of other parts of the molecule.

In a sixth embodiment of the present invention, the naturally occurring allergen originates from the taxonomic order of Poales, Asterales or Urticales. Examples of scaffold proteins of the major grass pollen allergen Phl p 1 are isoforms of Zea m 1 exemplified by accession number Q07154, isoforms of Gly m 1 exemplified by accession number U03860, isoforms of Ory s 1 exemplified by accession number U31771, isoforms of β-expansins exemplified by accession numbers: U95968, AC001229, U95967, s53082, U30477, U85246, Y07782, U30479, U30481, U30480, U30478, U30476, U30460, U30382, U64890, U64891, U64892, U64893, U82123, D26459, D88415, isoforms of Group 2 and group 3 grass allergens exemplified by accession numbers: P14947, X73363, A48595, P43214, P14948, U25343, Z50867. Phl p 5 is another example of a grass pollen allergen. Examples of Phleum pratense group 5 allergen, Phl p 5 scaffold proteins include: P93466, O81342, Q9SBE0, O81343, O81344, 2023228A, S38584. Examples of Lolium perenne group 5 allergen, Lol p 5 scaffold proteins include CAB64344, Q9XF24, a38582. Examples of Poa pratensis group 5 allergen, Poa p 5 scaffold proteins include: Q9FPR0, B39098. Isoforms of Holcus lanatus group 5 allergen, Hol 15 exemplified by (O23971, O23972, Q9FPQ9). Isoforms of Phalaris aquatica group 5 allergen, Pha a 5 exemplified by (MP51_PHAAQ). Isoforms of Dactylis glomerata group 5 allergen, Dac g 5 exemplified by (Q93XE0, Q93XD9). Isoforms of Hordeum vulgare group 5 allergen, Hor v 5 also referred to as Hor v 9 exemplified by (O04828). Isoforms of Phleum pratense group 6 allergen, Phl p 6 exemplified by (O65868, CAA76557).

In a seventh embodiment of the present invention, the naturally occurring allergen is a dust mite allergen, preferably originating from Dermatophagoides, and preferably Der p 2 (database accession number: P49278). Preferred Der p 2 scaffold proteins are Eur m 1 (database accession number: P25780), Gly d 2 (database accession number: AJ272216), and Lep d 2 (database accession number: S66499).

A specific embodiment of a Lep d 2 protein variant is a protein variant that comprises at least two primary mutations selected from the group consisting of: D17L, D17I, D17V, D17M, S19P, Q32K, Q32R, Q32H, K33P, T35Q, T35N, N88K, N88R, N88H, T92N, T92Q, A95K, A95R, A95H and optionally one or more secondary mutations selected from the group consisting of: K6X, S22X, R30X, K76S, K81X, V114X. This is an example of a Lep d 2 protein variant with a single epitope area established on the surface of the protein, optionally with downregulation of Der p 2 antibody cross-reactivity at other parts of the surface.

Another specific embodiment of a Lep d 2 protein variant is a protein variant that comprises at least two primary mutations within a single epitope area selected from the group consisting of: D45N, D45Q, N47K, N47R, N47H, K48T, K48S, T50K, T50R, T50H, K52E, K52D, L54K, L54R, L54H, E107K, E107R, E107M, H112D, H112E, T119I, T119L, T119V, T199M and optionally one or more secondary mutations selected from the group consisting of: K6X, S22X, K29X, R30X, K76X, K81X.

A specific embodiment of a Gly d 2 protein variant is a protein variant that comprises at least two primary mutations selected from the group consisting of: K2Q, K2N, K4D, K4E, K10N, K10Q, T14K, T14R, S22H, S22R, S22K, K39V, K39L, K39I, K39M, D45N, D45Q, T60L, T60V, T60I, T60M, Q6three-dimensional, Q63E, K80V, K80L, K80I, K80M, T91S, H112D, H112E, R122I, R122V, R122L, R122M and optionally one or more secondary mutations selected from the group consisting of: K6X, preferably K6R or K6H, R30X, preferably R30K or R30H, F74X, preferably F74Y or, F74W, K81X, preferably K81R or K81H, K88X, preferably K88R or K88H, T90X, and V114X, preferably V114L, V114I or V114M. This is an example of a protein variant with increased IgE reactivity in comparison with Der p 2 and optionally with secondary mutations where amino acids are substituted with homologous amino acids in order to avoid destabilization of the protein variant.

Other specific embodiments of Der p 2 scaffold proteins are isoforms of group 2 dust mite Tyrophagus putrescentiae allergens Tyr p 2 exemplified by accession number O02380, isoforms of storage mite Lepidoglyphus destructor group 2 allergens Led d 2 (mistakenly referred to as Led d 1 in some publications) exemplified by accession numbers: P80384, S48727, 2118249B, isoforms of Gly d 2 exemplified by accession numbers: CAB76459, Q9U5P7, isoforms from the group of homologous proteins exemplified by accession numbers 097763, P79345, Q9VQ62, Q9Z0J0, AAF99719, Q28895.

In a further preferred embodiment scaffold proteins of the major house dust mite allergen Der p 1 is Derf 1 (accession numbers P16311).

In an eighth embodiment of the present invention the naturally occurring allergen is a insect allergen from cockroach (*Blatella germanica* (allergens: Bla g 1 or Bla g 2), *Periplenata Americana* (allergen: Per a 1) or midges (Chironimus Spp.—allergen: Chi t 1)

In a ninth embodiment of the specific invention, the naturally occurring allergen is an animal allergen, preferably a mammalian allergen, preferably originating from a cat, dog, rat, mouse or horse, preferably the Fel d 1 allergen from cat.

In a tenth embodiment of the present invention, the naturally occurring allergen is a venom allergen, preferably originating from the taxonomic order of Hymenoptera, Vespidae, Apidae, or Formicoidae. A preferred venom allergen is Ves v 5. Possible Ves v 5 scaffold proteins include: P35783, P35760, P35785, P35784, P35787, P35736, P35786, P10737, Q05108, P35781, P35782, P81657, P81656, P35780, P35759, Q05109, P35779, P35778). Furthermore other low homologous proteins exemplified by (P54108, O19010, P16562, Q16937, P48060, Q60477, P35795, P35795, Q09566, P47033, Q40374, P12020, Q41359, P47032, Q91055, Q034401, P08299, P11670, P36110, P16563, P54107, Q08697, Q04108, P79845, P07053, P09042, P35794, P04284, Q03402, P33154, P35792, Q05968, P35793, Q00008, Q41495, P16547, P13390, O22456, Q15335, Q62871, 088487, Q13409, P54131, Q9LRZ5, P18859, O04067.

In an eleventh embodiment of the present invention, the naturally occurring allergen is a food allergen from peanut, soya, cows milk, hens egg white or yolk, shrimp or cod.

In a twelfth embodiment of the present invention, the scaffold protein is homologous to a plant, grass, food, or mite allergens. Protein variants according to this embodiment comprise at least one primary mutation. Protein variant furthermore have deconvoluted CD-spectra that deviate less than 30%, preferably less than 20%, and even more preferably less than 10% compared to the deconvoluted CD-spectra of the naturally occurring allergen. Preferably, the scaffold protein has a level of sequence identity with the naturally occurring allergen of between 30 and 50%, and preferably, the α-carbon backbone tertiary structures of the scaffold protein and the natural occurring allergen resemble each other to the extent that the deviation between their circular dichroism spectra should deviate by less than 30%, preferably less than 20%, and even more preferably less than 10 (Example 4).

In a thirteenth preferred embodiment of the present invention, the naturally occurring allergen is a fungal protein.

Preferably, a protein variant of the invention comprises at least one T-cell epitope capable of stimulating a T-cell clone or T-cell line specific for the naturally occurring allergen.

Accordingly, a protein variant preferably induces a new allergen specific Th0/1 T-cell immune response on top of the Th2 T-cell response or the scaffold protein variants induce T-cells anergy or a shift of the response of the T-cells from the Th2-type to the Th1-type The invention further relates to the use of protein variants according to the present invention for use as a pharmaceutical as well the manufacture of a medicament for the treatment or prevention of allergy. Preferably, a pharmaceutical composition comprises two or more different recombinant protein variants according to the present invention, wherein each variant is defined by having at least one primary mutation, which is absent in at least one of the other variants. In this way, presentation of different epitope areas that mimick epitopes of the naturally allergen can be achieved while ensuring that the risk of IgE cross-binding on the surface of e.g. mast-cells is minimized. A composition according to the present invention preferably comprises 2-12, preferably 3-10, more preferably 4-8, and most preferably 5-7 different protein variants. Such compositions can be used for preparing a pharmaceutical for preventing and/or treating allergy.

Pharmaceutical compositions according to the present invention preferably further comprise a physiological or a pharmaceutically acceptable carrier and/or excipient and/or an adjuvant. "Carriers" or excipients include any carrier or excipient commonly used with pharmaceuticals such as oils, starch, sucrose and lactose. The compositions according to the present invention may be in a form suited for oral intake including, capsules, pills, tablets and syrups. Alternatively, compositions according to the present invention may be in the form of a parenteral formulation suitable for e.g. intravenous, subcutaneous, etc. administration.

"Adjuvants" refers to a substance that stimulates and prolongs antibody synthesis when injected together with an antigen. An example of an adjuvant includes Freunds complete/incomplete adjuvans and aluminium hydroxide gels. A pharmaceutical composition according to the present invention is preferably in the form of a vaccine against allergic reactions elicited by a naturally occurring allergen in patients suffering from allergy.

Included in the scope of the present invention is methods of vaccination or treatment of an individual by generating an immune response in the individual comprising administering to the subject a recombinant protein variant or a pharmaceutical composition according to the invention.

Also comprised in the scope of the present invention are processes for preparing a pharmaceutical composition mixing a recombinant protein variant or a composition according to the present invention with pharmaceutically acceptable substances and/or excipients and/or adjuvants.

A further aspect of the present invention includes methods of preparing a recombinant protein variant wherein the recombinant protein variant is produced from a DNA sequence obtained by DNA shuffling (molecular breeding) of DNA sequences encoding the scaffold protein and the naturally occurring allergen.

Finally the present invention relates to DNA sequences encoding recombinant protein variants. Likewise, the present invention comprises expression vectors and host-cells that contain DNA sequences according to the present invention and are capable of producing recombinant protein variants. Also, methods of producing recombinant protein variants comprising the step of cultivating such host-cells with vectors are included in the present invention. Diagnostic assays for assessing relevance, safety, or outcome of therapy of a subject using a recombinant protein variant are also included in the invention, wherein an IgE containing sample of the subject is mixed with said protein variant or said composition and assessed for the level of reactivity between the IgE in said sample and said protein variant.

Definitions

Scaffold protein: The scaffold protein is a naturally occurring protein that often has a significant degree of amino acid sequence homology with the allergen that is selected for allergy vaccination. Furthermore, the scaffold protein has a three-dimensional folding pattern resembling that of the naturally occurring allergen. It is difficult to give an exact definition on which criteria must be fulfilled in order for two proteins to have a similar folding pattern. However, the man skilled in the art knows that proteins or protein domains with more than 10% amino acid homology have a high probability of being folded in a similar way and sharing similar amounts of α-helices, random coil, and β-sheets. This can be measured by e.g. circular dichroism, wherein the deviation between the two protein spectra should deviate by less than 30%, preferably less than 20%, and even more preferably less than 10.

Preferably, there is little or no measurable reactivity of the scaffold protein with allergen specific IgE, thereby enabling establishment of an allergen specific surface area, i.e. an epitope structure on the scaffold protein. A mutated scaffold protein with only one allergen specific epitope area is thus unable to bind more than one IgE molecule and thus unable to cause cross-binding of IgE molecules attached to the surface of e.g. mast-cells. Protein variant surface areas that resemble allergen epitopes are herein referred to as e.g. "epitope area", "mimicking an epitope", etc.

"Allergen specific antibodies", e.g. Bet v 1 specific antibodies mean antibodies which react with the naturally occurring allergen. Such antibodies may further react with other structurally related proteins including the mutant variants.

The decree of sequence homology between the scaffold protein and the allergen is between 0 and 95%, preferably between 5 and 90%, more preferably between 10 and 67%, even more preferably between 20 and 60%, and most preferably between 30 and 50%. 67% is often chosen as the lowest degree of sequence identity in order to characterize two proteins as isoforms or homologous proteins (King et al, (1995) J. Allergy Clin. Immunol. 96:5-14). The scaffold protein is preferably not an isoform or a homologous protein of the naturally occurring allergen, thereby ensuring that the scaffold protein has a low degree of antibody cross-reactivity with the allergen.

The protein variant compared to the scaffold protein has an increased binding capacity with respect to antibodies that are specific to the naturally occurring allergen: This statement can be regarded as both relating to the complete protein variant as well as to a single epitope.

Scaffold protein devoid of binding to IgE antibodies specific to the naturally occurring allergen: The scaffold molecule selected for mutation may be devoid in binding antibodies specific for the allergen in question, or preferably some IgE antibodies from an average patient allergic to the allergen in question may be cross-reactive. Devoid in antibody binding means a reduction in average antibody affinity of a factor of $10^3$, more preferably $10^4$, most preferably $10^5$ or more. For polyclonal antibodies affinity is normally an average affinity. For monoclonal antiobodies the affinity is also referred to as avidity Primary mutations (creation of epitopes, stabilizing backbone, etc.) Introduction of a primary mutation may be a substitution, a deletion or an addition. Preferably the primary mutation is a substitution of at least one scaffold amino acid residue with residue(-s) identical or homologous to the amino acid found in a corresponding position in the natural allergen. Preferably, the protein variant comprises 2-50, more preferably 2-40, more preferably 3-25, more preferably 4-15 and most preferably 5-12 primary mutations. Also, the protein variant may comprise one or more mutated sequence fragments consisting of a number of consecutive mutated amino acids. Preferably, the mutated sequence fragment consists of 2-15, more preferably 3-12 and most preferably 5-10 amino acids.

In a preferred embodiment of the invention, all primary mutations of the protein variant are located in a surface region having an area of about 900 Å$^2$. In this preferred embodiment of the invention the protein variant only has one epitope reactive to IgE antibodies specific to the naturally occurring allergen. It is believed that such a protein variant has the advantage that it will not give rise to an undesirable immune response, e.g. an anaphylactic reaction, since such responses require IgE cross-linking to be triggered, i.e. such responses require that the allergen has at least two non-overlapping epitopes.

Preferably, the primary amino acid residues to be mutated are surface-exposed amino acids. It is preferred that the amino acid residues to be mutated have a solvent accessibility of above 20%, preferably above 30%, more preferably above 40%, and most preferably above 50%.

In addition to or as an alternative to mutation of surface exposed amino acids, i.e. the amino acid constituting the epitopes, the amino acids of the backbone of the protein, i.e. amino acids located in the interior of the tertiary protein structure may be mutated. Such mutations can potentially modify the folding of the molecule and thereby change the binding properties of the epitopes on the surface of the protein. One purpose of the mutations may be to stabilise the folding of the backbone and hence the tertiary structure of the protein. An example could be the introduction of disulphide bridges.

In one embodiment of the invention, one or more of the mutations are carried out by site-directed mutagenesis. Site directed mutagenesis can be carried out as described in detail in e.g. "Molecular cloning" by Sambrook & Rusell (2001) Cold Spring Harbor Laboratory Press.

DNA shuffling: DNA shuffling is a term that encompasses a number of recombinant methods whereby a number of sequences or sequence fragments that share significant homologies are disrupted by e.g. digestion, sonication, etc. By religation and subsequent PCR (polymerase chain reaction) a large number of novel variants are generated on a random basis. DNA shuffling can also be carried out in a more controlled manner, by e.g introducing primers with well defined sequences into the reaction.

Gene library methods: Gene library methods include construction, expression and screening of any form of DNA library encoding mutated variants of a protein. The protein coding DNA sequence can either be mutated semi-randomly or randomly. A non-limiting example that describes a semi-random library could be a library where mutated gene variants are mutated with respect to DNA codons representing surface exposed amino acid residues only. Another example is any restrains in respect to the outcome of the mutation i.e. if mutation only allows for substitution to certain amino acid residues i.e. homologous amino acid residues, small or charged/non-charged amino acid residues. In one example the diversity is introduced by the use of degenerated oligo nucleotide primers and PCR-techniques. In another example the mutation diversity is introduced by use of a host organism that introduces mutations at a high frequency. One or more mutations are introduced by a semi-random library methodology.

Secondary mutations (weakening/elimination of epitopes): The secondary amino acid mutations are mutations introducing into the scaffold protein amino acid residues, which are not present in the corresponding position in the naturally occurring allergen.

The secondary amino acid mutation may be a substitution, a deletion or an addition. Preferably, the protein variant comprises 0-50, more preferably 1-40, more preferably 2-25, more preferably 3-15 and most preferably 4-12 secondary mutations. Also, the protein variant may comprise one or more secondary mutations each consisting of a number of consecutive mutated amino acids. Preferably, the mutated sequence fragment consists of 2-15, more preferably 3-12 and most preferably 5-10 amino acids.

The purpose of the secondary mutation as mentioned above is to modify an epitope of the scaffold protein to eliminate or reduce its antibody binding effect, and hence IgE cross-linking and risk of inducing anaphylactic reactions.

Epitope grafting: Epitope grafting is understood as establishment of allergen specific antibody binding properties on the surface of a scaffold protein. This "grafted" scaffold protein variant represents an attractive vaccine candidate against allergies due to the capacity of raising a protective immune response.

Protective immune response: Raising a protective immune response means to alter the reaction of the immune system towards a naturally occurring allergen in order to avoid the adverse effects associated with allergy. The protective immune response is thought to be mediated largely by generation of a large number of IgG antibodies that presumably block the interaction between allergen and IgE antibodies. A protective immune response most likely also involves stimulation of T-cells.

Surface structure/contour: Whereas the three-dimensional folding of a protein is determined by the tertiary folding of the α-carbon backbone, the nature of the molecular surface structures/contours with regard to topography and charge distribution of a protein is in part determined by the nature and composition of amino acid chains that is present at the surface and hence show some degree of solvent accessibility. Introduction of primary and/or secondary mutations at the protein surface will therefore alter the nature of the protein surface structures/contours.

Composition of the invention: A composition or a pharmaceutical composition according to the invention may comprise at least one scaffold protein variant as well as any other pharmaceutical or non-pharmaceutical reagents, exhibients, adjuvants, carriers, vehicles or drug delivery systems.

Protein variant: A protein having an amino acid sequence, which differs from a natural occurring protein by one or more amino acids. Preferably, a protein variant according to the present invention is a recombinant protein variant of a scaffold protein, said protein variant can react with patient sera from individuals that are allergic to an allergen that has significant amino acid sequence homology with a naturally occurring allergen. However, the protein variant has a lower degree of IgE reactivity compared with naturally occurring allergen.

Level of amino acid identity: The level of amino acid identity is here defined by the percentage of amino acid residues that in two primary protein sequences with respect to corresponding positions are identical.

Level of amino acid homology: The level of amino acid homology is herein defined by the percentage of amino acid residues that in two primary protein sequences with respect to corresponding positions are either identical or homologous amino acid residues.

Allergen: An allergen according to the present invention is any naturally occurring protein that has been reported to induce allergic, i.e. IgE mediated reactions upon their repeated exposure to an individual. Examples of naturally occurring allergens include inhalation allergens (tree- and grass pollen allergens, mite allergens, insect allergens (inhalant and venom allergens), animal hair and dandruff allergens from e.g. dog, cat, horse, etc.), and food allergens.

Modulation of an immune response: Following vaccination with a recombinant protein variant that partly mimics the structure of the allergen, an "immune response" is thought to occur at several levels: (a) the protein variant may bind to preformed IgE that are either prebound to e.g. mast-cells or found in the circulation, without causing IgE cross-binding on the surface of the mast-cells, (b) novel IgG antibodies may be formed or existing IgG antibodies might become "matured" in order to increase epitope affinity, and (c) novel or existing T-cells may become activated. Modulation of the immune response in the context of the present invention is thus interpreted as the ability of a recombinant protein variant to induce a protective IgG response and preferably also stimulating T-cells while at the same time reducing the risk of IgE cross-binding on the surface of e.g. mast-cells. It is primarily the IgE cross-binding on the surface of mast-cells that is thought to be responsible for the adverse effects following allergen exposure.

It can be measured in several ways whether an allergen variant raises "an immune response corresponding to that of a naturally occurring allergen". Not limiting to the invention a preferred way of measuring this is by measuring in a statistically significant manner (p<0.05) in at least one immunoassay the ability of the scaffold protein variant to bind to serum IgE from an allergic subject or to inhibit the binding of serum IgE from an allergic subject to the naturally occurring allergen. Another preferred way is the measurement of the ability of antibodies in a serum sample from scaffold protein variant immunized animals to compete with binding to allergen specific IgE in an immunoassay.

Affinity of antibody-antigen interaction: Specificity and affinity of antibody-antigen interactions are two sides of the same coin. The reason for this is that the binding strength, i.e. the affinity, is determined not only by the attractive forces (enthalpic contribution), i.e. ionic interactions, hydrogen bonds and Van der Waals interactions, but also by the almost complete displacement of water molecules from the interface between the two molecules in the complex (entropy contribution). In common language this means that a perfect fit in the topographical contours of the molecular surfaces is of crucial importance.

Reduced fit, e.g. as a consequence of mutation, will almost always lead to reduced affinity of the interaction. The complex will still be formed, but at higher concentration, and in kinetic terms the equilibrium will be displaced, so that at any given time a higher proportion of the antigen and antibody molecules will be in free solution and conversely a lower proportion of the molecules will be bound in complexes.

Thus, increasing the concentration of any of the reactants, i.e. antigen or antibody, will lead to increased concentration of the complex—regardless of the affinity. In common language this means that any antigen will bind to any antibody provided that the concentrations are high enough. This in turn means that some restrictions should be imposed on the concentrations of the reactants in order to assure that the reaction will take place in concentrations that are close to physiological concentrations, i.e. a specific interaction.

It also follows that $K_d$ is a direct measure of the affinity of the interaction. Practically speaking, however, $K_d$ is a difficult measure, since polyclonal antibodies usually will be employed.

If [AgAb] is plotted as a function of log [Ag] at constant [Ab] an S-shaped curve is obtained. The [Ag] at half maximal binding is a practical useful measure—but of a combination of $K_d$ and $B_{max}$. The [AgAb] at saturation is a constant, $B_{max}$, at a given [Ab]. $B_{max}$ is conceptually easier to understand since it is the maximal level of binding, however, in practice it can be difficult to achieve high enough concentrations of Ag. $B_{max}$ is the binding capacity. Thus, relative measures of binding capacities at given [Ab] can be compared.

An antigen which has been mutated in such a way that a section of the surface is significantly altered has a lower binding capacity with respect to polyclonal antibodies specific for the non-mutated antigen. The average affinity of the interaction between the mutated antigen and a polyclonal antibody is also likely to be reduced. However, if the specificities of the polyclonal antibodies are not randomly dispersed over the entire surface (which is a known situation for some IgE from individual patients), or in the case of a monoclonal antibody, the binding capacity as well as the average affinity may be unaffected by the mutations, i.e. if the epitopes recognized by the antibodies are outside the area affected by the mutations. The chance of this situation is reduced in the case of pools of patient sera or polyclonal antibodies raised in experimental animals by massive immunization.

According to the current invention, mutations might be introduced in some surface areas in order to reduce the average affinity in these areas, and vice versa in other, which are different for the purpose of achieving an equalized low-affinity interaction on the entire surface for antibodies specific for the allergen in question. These scaffold protein variants have antibody binding capacity similar to the allergen in question, but with considerably reduced average affinity. The ability to release histamine by cross-linking receptor-bound IgE on the surface of mast-cells or basophils in an in vitro test system can be used to assess these combined features of the scaffold protein variants. The potential to release histamine to some degree reflects the average affinity, and to some degree it mirrors the relevant clinical reaction. Furthermore, such scaffold protein variants stimulate production of IgG antibodies, which will most likely interact with low affinity with the natural allergen. Due to the great abundance of IgG antibodies in comparison to IgE, even low affinity IgG interactions are thought to have the capacity to interfere beneficially with the high affinity interaction between the natural allergen and a low concentration of IgE.

Assesment of IgE reactivity e.g. Binding Capacity and Binding Affintity

Experimental approach addressing the evaluation of scaffold protein variant IgE reactivity can be performed in many ways. For instance; $K_d$, i.e. the average affinity of the antibody-antigen interaction, and $B_{max}$, i.e. the binding capacity, can be experimentally addressed in solid phase immuno-inhibition assays or in direct binding assays.

In solid phase immuno-inhibition assays the antibody may be coupled to the solid phase. The experiments can also be performed using solid phase coupled antigen. The binding of a purified and labeled allergen is then inhibited by a dilution series of the test antigen, i.e. mutated scaffold, and compared to a similar experiment performed using the non-mutated molecule. In a plot of inhibition percentage as a function of the logarithm of inhibitor concentration the relationship corresponds to an S-shaped curve. If a mutated antigen has modified $K_d$ but identical $B_{max}$ this will correspond to a parallel displacement of the curve along the x-axis. A higher affinity will shift the curve to the left and vice verca. A change in $B_{max}$ will affect the maximal level of the curve as well as the slope of the linear section of the S-shaped curve. In all cases where a mutated antigen is compared to a non-mutated molecule, the linear sections of the curves can be statistically tested for linearity and it can be tested whether the linear sections of the curves are parallel, or the comparison between the parameters obtained from a complete curve fit, i.e. four parameter logistic curve fit, can be used for the statistical analysis. If the curves are parallel and displaced relative to each other this is an indication of a different affinity of the antibody-antigen interaction. If the slopes are different this is an indication of a change in epitope composition, i.e. binding capacity or a change in both binding capacity and affinity.

Surface-exposed amino acid: Means that the amino acid residue is located at the surface of the three-dimensional structure in such a manner that when the allergen is in solution at least a part of at least one atom of the amino acid residue is accessible for contact with the surrounding solvent. Preferably, the amino acid residue in the three-dimensional structure has a solvent (water) accessibility of at least 20%, suitably at least 30%, more suitably at least 40% and most preferably at least 50%.

Solvent accessibility: Defined as the area of the molecule accessible to a sphere with a radius comparable to a solvent (water, r=1.4 Å) molecule. The expressions "surface-exposed", "surface amino acid", and "solvent-exposed" are used interchangeably.

Homologous amino acid residues: Homologous amino acid residues are characterised by sharing essentially the same chemical features. An example of grouping amino acids is to characterize Ala, Val, Leu, Ile, and sometimes Gly and Pro as "aliphatic residues". Other "groups" include hydroxyl residues (Ser and Thr), acidic residues (Asp and Glu), amide residues (Asn and Gln), basic residues (Lys and Arg), and the aromatic residues (Phe, Tyr, and Trp). Other groupings of amino acids into groups sharing similar chemical characteristics are of course possible, e.g. division of amino acids into hydrophobic and hydrophilic residues.

The present invention is further illustrated by the following non-limiting examples.

EXAMPLES

Example 1

Modification of Scaffold Proteins Homologous to Bet v 1

Site Directed Mutagenesis

All Mal d 1 mutants were generated as follows. First (I), each single mutation (or several mutations if located closely together in the DNA sequence) were introduced into DNA sequences coding for rMal d 1 (2620) (accession number: AJ488060) using sense and anti-sense mutation-specific oligonucleotide primers accommodating each mutation(s) along with sense and anti-sense oligonucleotide primers accommodating either upstream or downstream neighbour mutations or the N-terminus/C-terminus of Mal d 1, respectively as schematically illustrated in FIG. 1 (I). Secondly, PCR products from PCR reactions (I) were purified by agarose gel electrophoresis and PCR gel purification, mixed and used as templates for an additional PCR reaction (II) with oligonucleotide primers accommodating the N-terminus and C-terminus of Mal d 1 as schematically illustrated in FIG. 1 (II). The PCR products were purified by gel electrophoresis and PCR gel purification followed by ethanol precipitation, cut with restriction enzymes (Sac/EcoRI) or (SacI/XbaI), and ligated directionally into pMAL-c restricted with the same enzymes.

Nucleotide Sequencing

Plasmid DNA from 10 ml of bacterial culture grown to saturation overnight in LB medium supplemented with 0.1 g/l ampicillin were purified on tip 20 columns (QIAGEN) and sequenced using the Ready reaction dye terminator cycle sequencing kit and a Fluorescence Sequencer AB PRISM 377, both from (Perkin Elmer), following the recommendations of the supplier.

Protein Expression and Purification

Recombinant Mal d 1 (2620) and mutants were over-expressed in *Escherichia coli* DH 5α cells in operon with the amino-terminal *E. coli* fusion partner, maltose binding protein (MBP). Six 5L flasks containing 1L of LB-medium supplemented with 100 mg/L ampicillin were inoculated with 10 ml of overnight cultures of transformed *E. coli* cells grown with shaking at 37° C. to an optical density of 0.75 at 600 nm before induced by addition of 5 ml 100 mM of IPTG and harvested by centrifugation 3 hours post induction. Cells from 6L of culture were re-suspended in 2×150 ml lysis buffer (30 mM NaCl, 10 mM EDTA, 1 mM Benzamidine, 10 μg/ml SBTI 10 mM Na2HPO4.12H2O/NaH2PO4.H2O buffer pH 7.0, 0.02% NaN3) added 3 mM PMSF and lysed by sonication for 10 minutes on ice. After sonication removal of DNA was performed by adding 1.5 ml 1 mg/ml DNAse, 5 mM MgCl2 and 40 ml 4M NaCl before 30 minutes incubation at room temperature. Cell lysates were centrifuged 30 minutes 12000 rpm, 4 C. Supernatants (300 ml) were pooled and filtered using 0.45 μm filters before addition 1200 ml of dilution buffer (0.5 M NaCl, 2 mM EDTA, 1 mM Benzamidine, 10 μg/ml SBTI, 10 mM Na2HPO4.12H2O/NaH2PO4.H2O buffer pH 7.0, 0.02% NaN3). Recombinant fusion protein was isolated by amylose affinity chromatography by operating 200 ml amylose columns with the Äkta explorer system (Pharmacia Biotech, Sweden) equipped with the Unicore 4.0 software. Eluted fusion protein was concentrated using amicon pressure cells equipped with 30 kDa cuttoff filters to 30 ml and dialyzed against 2×5 L 20 mM TRIS-HCl pH 8.0 overnight.

All MBP-Mal d 1 fusion proteins, were cleaved at 20° C. for 20 hours with slow stirring with 1% 1 mg/ml Factor Xa in cleavage buffer (20 mM TRIS-HCl pH 8.0, 100 mM NaCl, 2 mM CaCl2, 0.02% SDS to 1.00%) at fusion protein concentrations between OD280=4-6. Factor Xa cleavage was stopped by adding 5 mM benzaminide and 10 mM EDTA. Protein solutions were concentrated using amicon pressure cells equipped with 10 kDa cuttoff filters to 20 ml added to a 50 ml superloop before subjected to FPLC using Pharmacia Sephadex G-75 column for 10 loops operated by the Äkta explorer system following the recommendations of the supplier. Protein fractions containing Mal d 1 were pooled added NaCl to 200 mM and DTT to 5 mM and filtered (45 μm) before subjected to a second round of amylose afinity chromatography. Protein Fractions containing purified Mal d 1 were pooled and dialyzed against 2×5L of TRIS-HCl buffer pH 7.5 before concentrated using amicon pressure cells equipped with 3 or 10 kDa cuttoff filters to >1 mg/ml for storage at 4° C. or −80° C. Mal d 1 mutants with authentic amino-terminals were purified to electrophoretic homogeneity at 2-5 mg yields per liter of culture medium. All purified Mal d 1 preparations appeared as single bands after silver-stained SDS-polyacrylamide electrophoresis with an apparent molecular weight of 17.5 kDa.

Circular Dichroism Spectroscopy

Circular dichroism spectra were obtained using an OLIS DSM 10 CD spectrophotometer (On Line Instrument Systems, Bogart, Geo, USA), equipped with cylindrical (31-Q-1/CD) or square (21-Q-1/CD) 0.1 cm light path quartz cuvettes (Starna, Essex, UK). The spectra were recorded from 260 nm to 184 nm collecting data at every second nm, 38 data points per spectrum. The temperature of the cuvette was maintained constant using a Julabo Model F30-C bath/circulator temperature control module (Julabo Labortechnik, Seelbach, Germany). Spectra were obtained in 0.01M sodium phosphate buffer, pH 7.2, at a concentration of 0.1 mg protein per mL. Each spectrum represents the arithmetic mean of four determinations corrected for buffer absorption and normalized to $\Delta\epsilon=0$ at 260 nm. The mDeg recorded was transformed to $\Delta\epsilon$ using:

$$\Delta\epsilon = mDeg/(32980 \cdot c \cdot l) Abs_{units}/(M \cdot cm)$$

Where mDeg is the circular dichroism signal, c is the concentration in mol/L as measured by amino acid analysis and l is the length of the light path in cm.

IqE-binding Experiments

Sera from individual patients or a pool of equal volumes of sera from several birch pollen allergic patients were used for specific serum IgE inhibition assays. rBet v 1.2801 (database accession number: Z80104) expressed and purified as described for rMal d 1, was biotinylated at a molar ratio of 1:5 (Bet v 1:biotin). The inhibition assay was performed on ADVIA Centaur System (Bayer, Denmark) as follows: A serum sample (25 µl) was incubated with paramagnetic beads (solid phase) coated with a monoclonal mouse anti human IgE antibody (ALK-Abelló, Denmark), washed, resuspended and incubated with a mixture of biotinylated Bet v 1 and inhibitor (non-biotinylated Bet v 1, rMal d 1 (2620) or mutated rMal d 1 allergens) in dilution series. The amount of biotinylated Bet v 1 bound to the serum IgE on the solid phase was estimated from the measured relative light units (RLU) after incubation with acridiniumester labelled streptavidin. The degree of inhibition was calculated as the ratio between the RLU's obtained using buffer and mutant as inhibitor.

Histamine Release Experiments (rMal d 1 (2762) and (2781))

100 µl of pipes buffer pH 7.4 or 100 µl of allergen dilutions in Pipes buffer pH 7.4, 1 ng, 3 ng, 10 ng, 30 ng, 100 ng, 1000 ng of rBet v 1.2801, rMal d 1 (2620) or mutated rMal d 1 (2762) or (2781) were added to 96 well plates in triplicates. Plates were preheated to 37° C. before 100 µl of preheated (37° C.) blood, diluted 1:5 with Pipes buffer pH 7.4, were added to wells with different allergen dilutions or Pipes buffer. Plates were then incubated 30 minutes at 37° C. before centrifuged 10 minutes at 800 g in a centrifuge with a plate-rotor. Supernatants from each of the wells were transferred to wells in new microtiter-plates that were lid and sealed with sealing tape before incubated at 0° C.

Histamine release in each sample was measured using the ELISA based Enzyme Immunoassay Kit ref. 2015 (Immunotech, France) following the recommendations of the supplier. 100 µl of sample or standard solutions were acylated with 25 µl of acylation buffer and 25 µl of acylation reagent to permit later binding to anti-histamine-antibodies. 50 µl of acylated histamine samples, standards or negative controls were then added to anti-histamine-antibody coated wells along with 200 µl of alkaline phosphatase conjugated histamine and incubated 2 hours at 5° C. with shaking. Plates were rinsed 3 times with diluted wash solution before 200 µl of Para-nitrophenylphosphate (pNPP) substrate solution was added to the plates that were incubated 30 minutes at room temperature with shaking before 50 µl of stop solution was added. The ability of the histamine samples and histamine standards (1 nM, 3 nM, 10 nM, 30 nM, 100 nM, 1000 nM) to inhibit binding of alkaline phosphatase conjugated histamine to anti-histamine antibody coated wells were measured as relative absorbance at 405 nm.

Results

Figure 1:
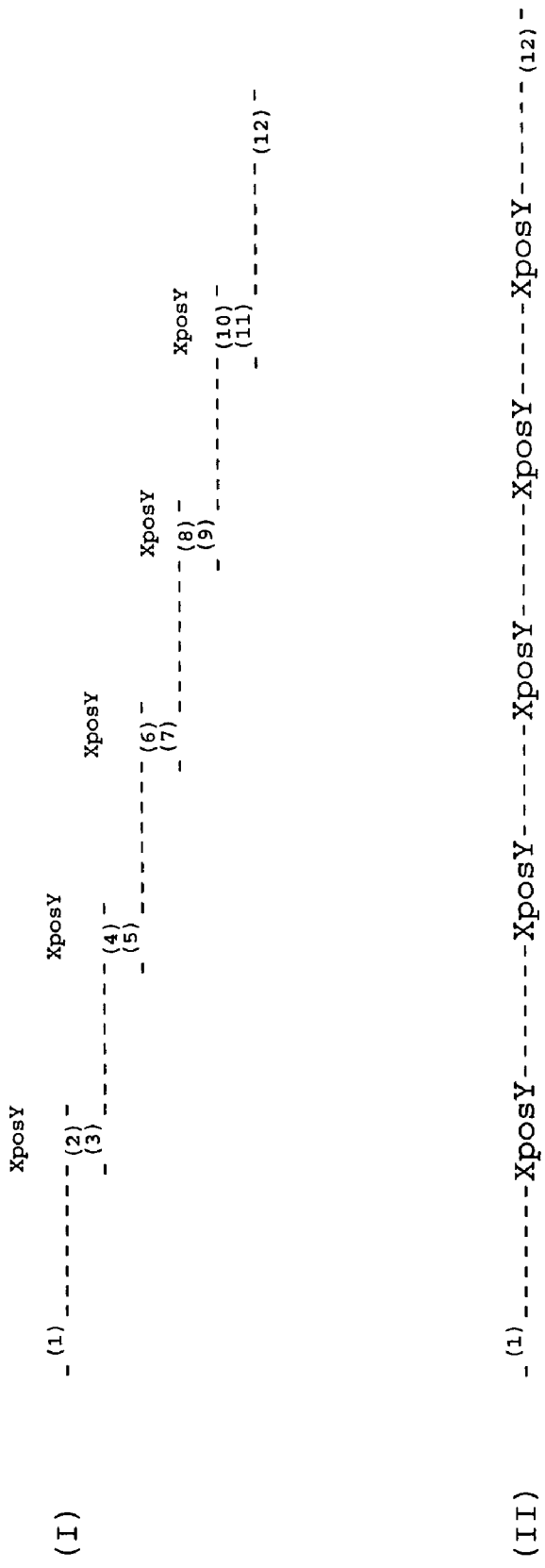
FIG. 1: Mutation by site directed mutagenesis. Punctured lines represent DNA sequences. Numbers in parentheses above lines represents sense oligonucleotide primers: (1), (3), (5), (7), (9), (11). Numbers in parentheses below lines represents anti-sense oligonucleotide primers: (2), (4), (6), (8), (10), (12). Notation X (position (pos)) Y represents mutations at different positions. (1) Represents the sense oligonucleotide primer accommodating the protein N-terminus. (12) Represents the anti-sense oligonucleotide primer accommodating the protein C-terminus.
Figure 2:
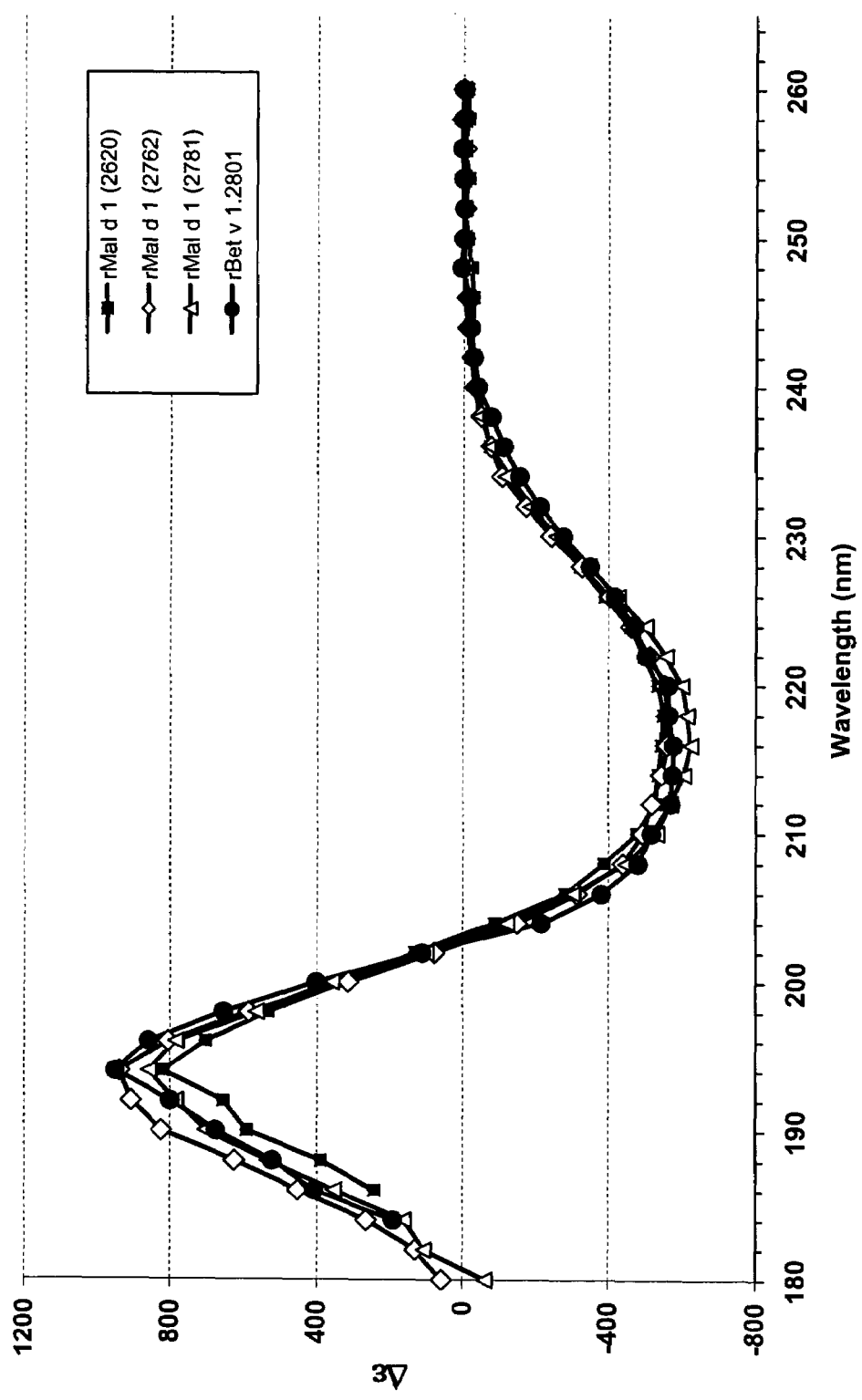
FIG. 2: Circular dichroism (CD) spectroscopy. CD spectra of rMal d 1 (2620) (■), rBet v 1.2801 (●), mutated rMal d 1 (2762) (◇) and mutated rMal d 1 (2781)(Δ).

The polypeptide backbone absorbs and is optically active in the far UV region below 260 nm and the magnitude of the absorbance is dependent upon the conformation of the backbone. Measuring differences in absorption of left- and right-circulary polarized light circular dichroism spectroscopy is able to detect alterations in secondary protein structure such as α-helices, β-sheets or random coil elements. In addition, measuring of circular dichroism spectra during protein heat-denaturation provides information about protein stability. To assess protein stability with respect to long term storage or buffer shifts circular dichroism spectroscopy was applied to all protein preparations prior to biological testing. Heat denaturation was applied to rMal d 1 (2620). Non-mutated rMal d 1 (2620) and rMal d 1 mutants (2781 and 2762) all had circular dichroism (CD) spectra with comparable shape as the CD spectrum of native folded rBet v 1.2801 (see FIG. 2). This shows that the rMal d 1 molecules contain the same secondary structure elements as rBet v 1.2801.

Figure 3A:
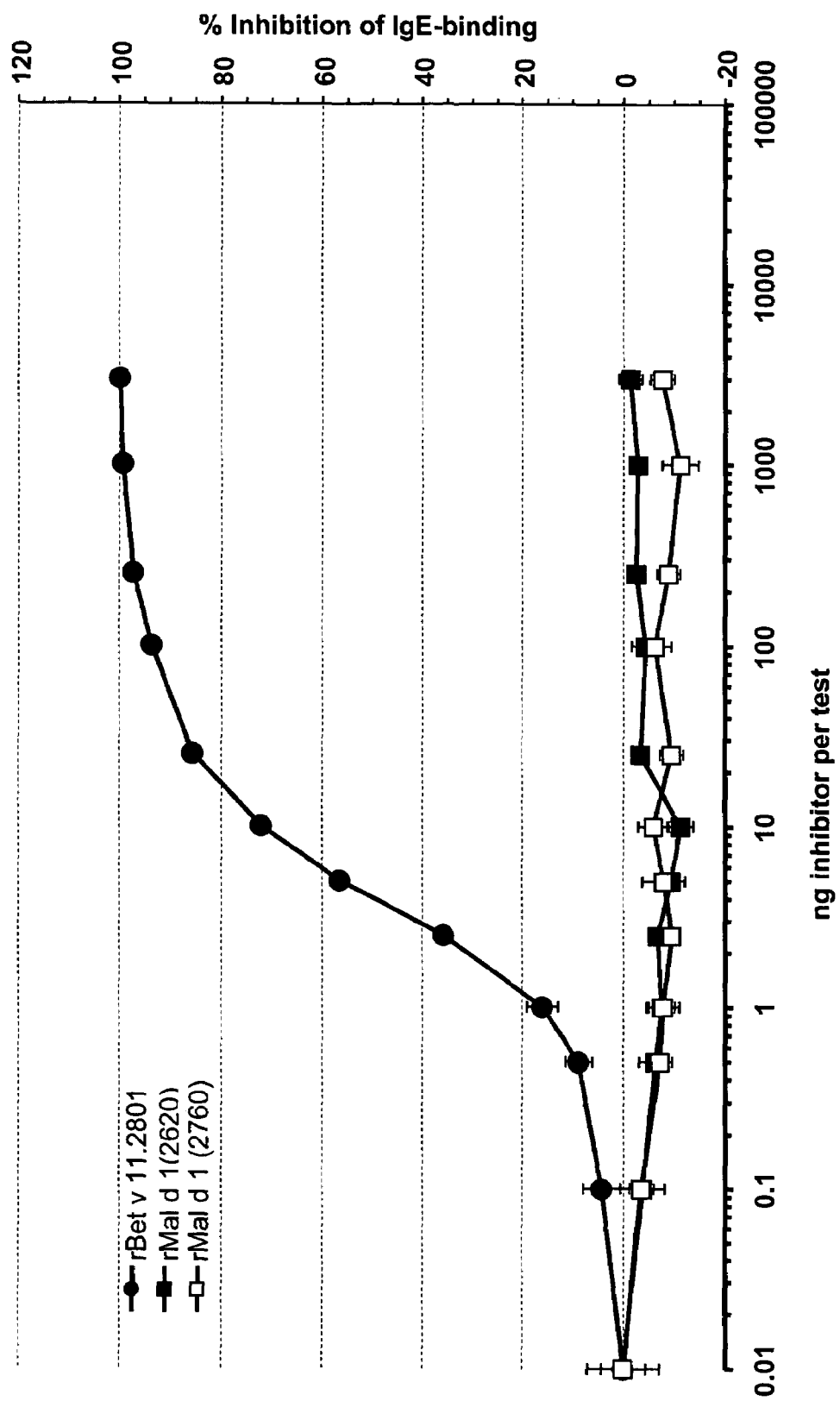
FIGS. 3A and 3B: Inhibition of the binding of biotinylated rBet v 1.2801 to pooled IgE serum from birch allergic patients by rBet v 1.2801 (●), rMal d 1 (2620) [■] or mutated rMal d 1 (2760) [□] with three secondary mutations. A=serum pool 0202/148. B=serum pool 11-97.
Figure 3B:
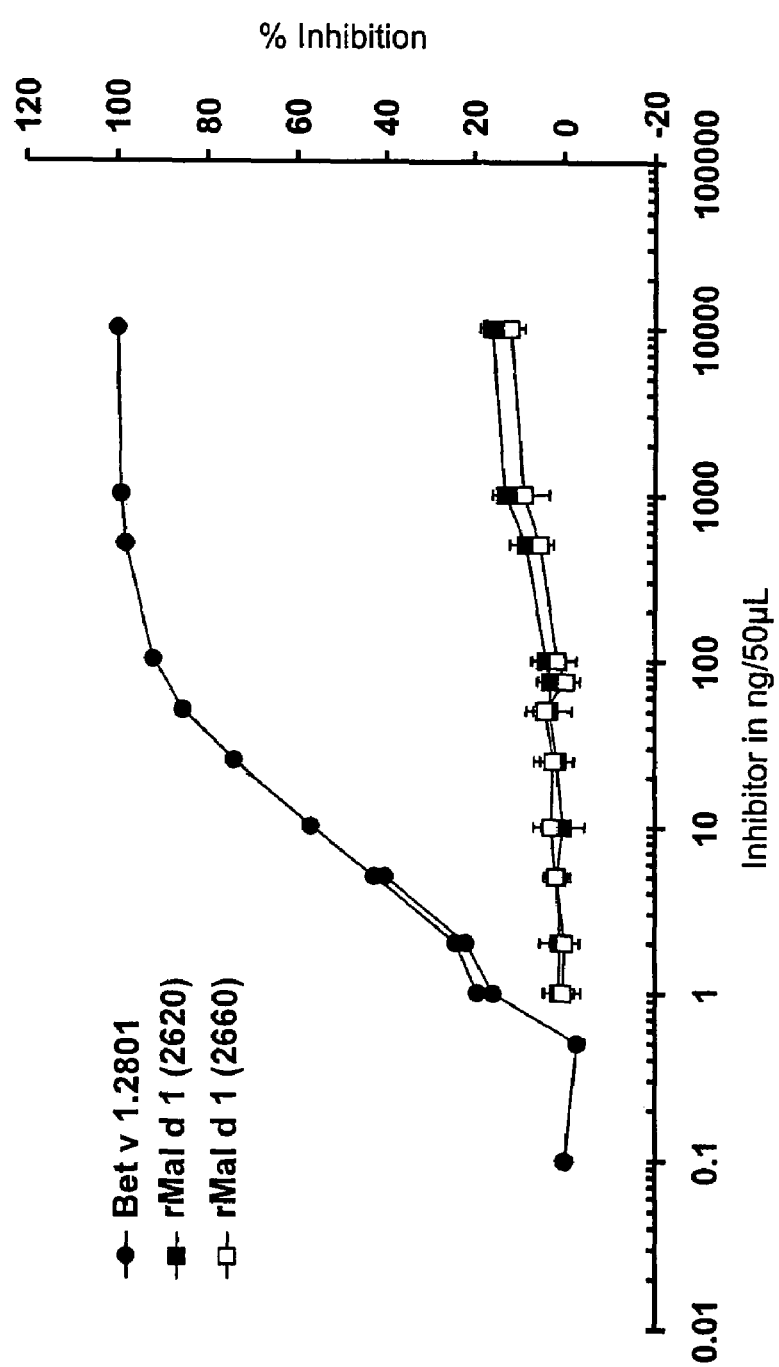
Figure 4:
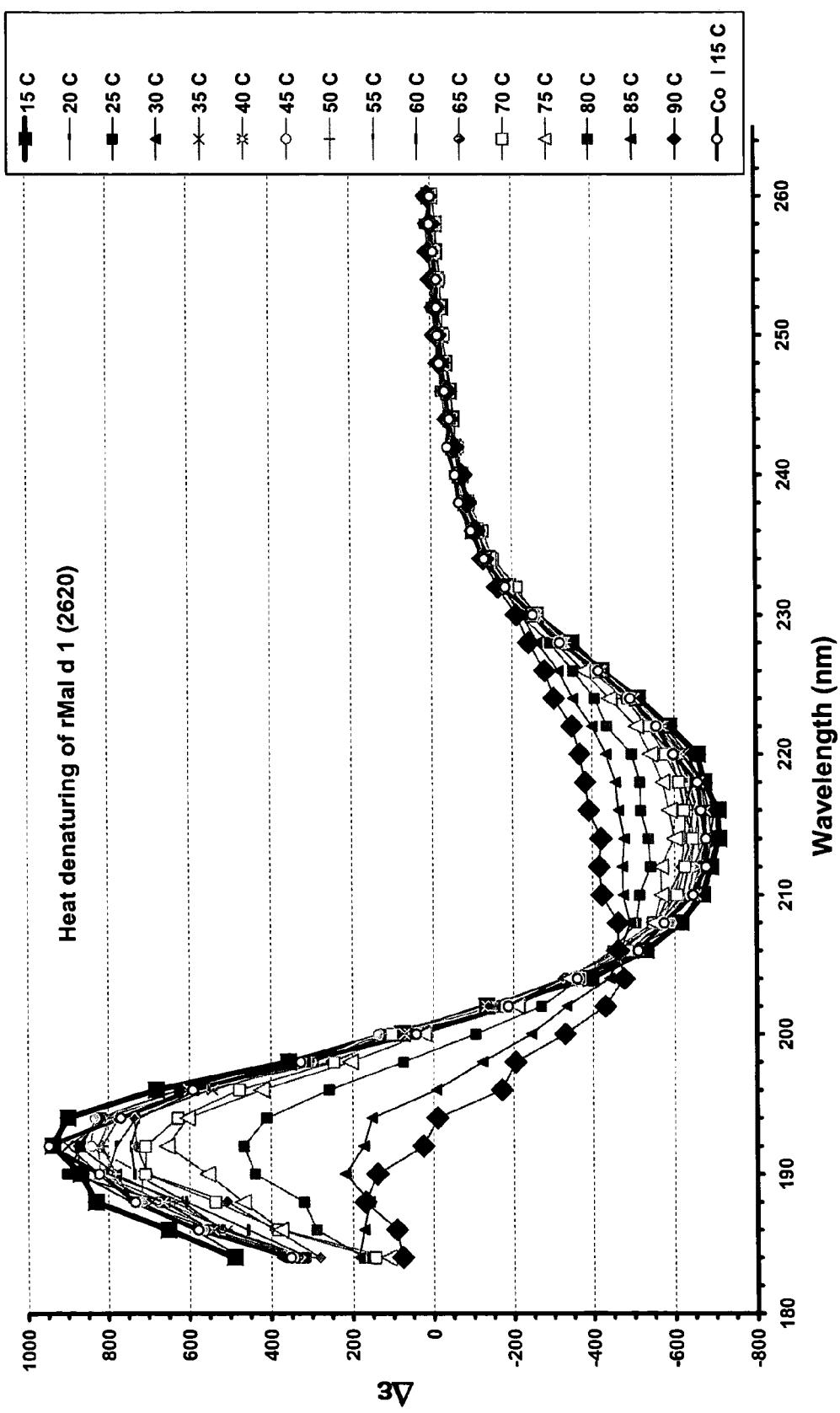
FIG. 4: Heat-denaturing of rMal d 1 (2620). Overlay of circular dichroism (CD) spectra obtained at 15° C. to 90° C. are shown. Native folded (15° C.) rMal d 1 (2620) has negative and positive amplitudes at 214-216 nm and 192-194 nm, respectively. Heat denatured (90° C.) rMal d 1 (2620) protein preparations have negative amplitudes at 204 nm and considerably less negative and positive values at 214-216 nm and 192-194 nm, respectively, compared to native folded allergen. The protein preparation heated to 90° C. was cooled down for an additional recording at 15° C. (o) which is overlapping with the spectrum of native folded protein preparations. Furthermore, the CD-spectra of rMal d 1 (2620) recorded at 70° C. are only slightly altered compared to the spectrum recorded at 15C.

Isoforms of Mal d 1 from apple have from 50-60% amino acid identity with Bet v 1 and show limited reactivity with Bet v 1 specific IgE. This is illustrated in FIGS. 3A and 3B showing the binding of birch pollen allergic patients serum IgE, from two different serum pools to biotinylated rBet v 1.2801, inhibited by rMal d 1 (2620)[■]. The inhibition curves show that serum pool A is unable to bind rMal d 1 (2620) and that rMal d 1 (2620) binds less than 20% of rBet v 1 specific IgE-antibodies in serum pool B. Being a naturally occurring isoform rMal d 1 (2620) is a stable protein. This is illustrated in FIG. 4 where heat denaturing experiments show that rMal d 1 (2620) maintain most of its secondary structure elements at temperatures up to 70° C. Furthermore, the heat denaturation experiment shows the ability of the protein to refold completely.

Isoforms of Mal d 1, e.g. rMal d 1 (2620) are thus regarded as suitable scaffold candidates for Bet v 1.

Figure 5A:
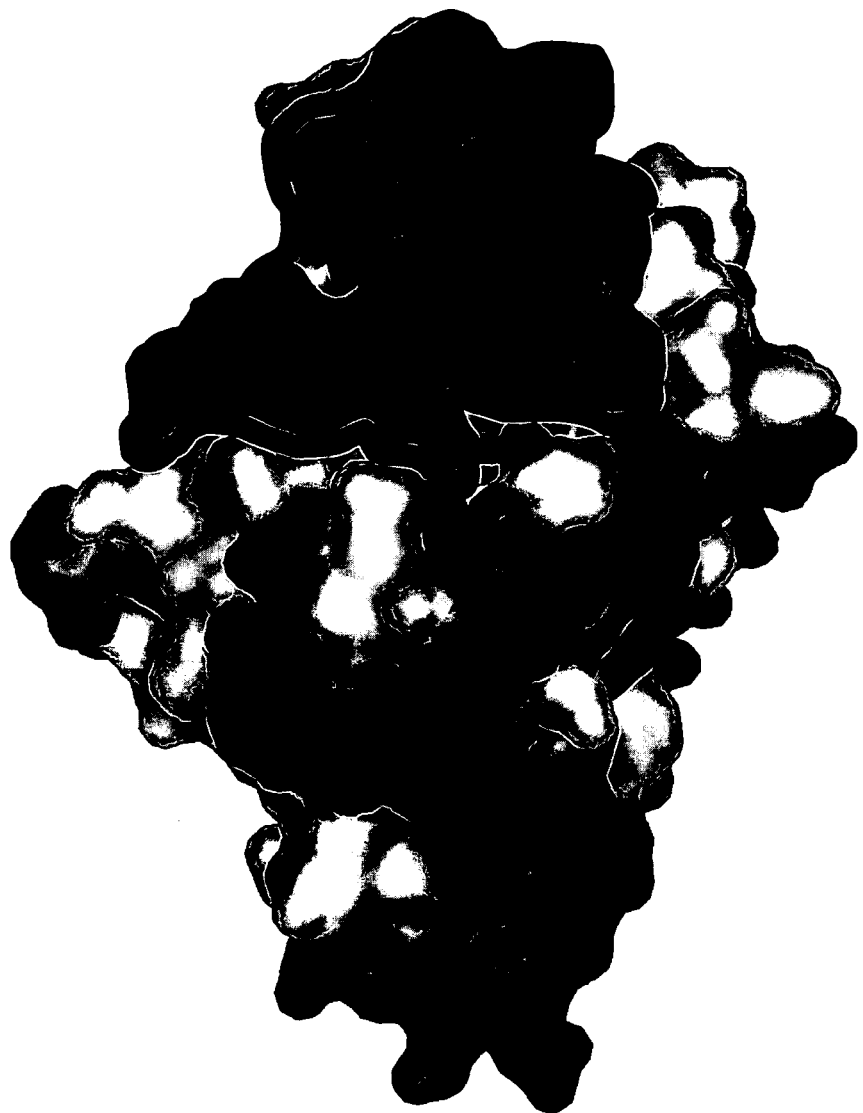
FIGS. 5A, B and C: Models of three-dimensional-structures of rMal d 1 (2620) (A,B) and rMal d 1 (2760) (C). Molecular surfaces are shown. Grey surface areas show Bet v 1.2801 specific amino acid residues on Mal d 1. White surface areas show Mal d 1 (2620) specific amino acid residues. A and C=front view. B=back view. One large birch-apple antibody cross-reactive surface area is framed in black in figure A. In figure C three secondary mutations N28T, K32Q, E45S in rMal d 1 (2760) are shown in black. Two of the secondary mutations N28T, K32Q affect both the topography as well as the amino acid charge distribution in the large birch-apple antibody cross-reactive surface area.
Figure 5B:
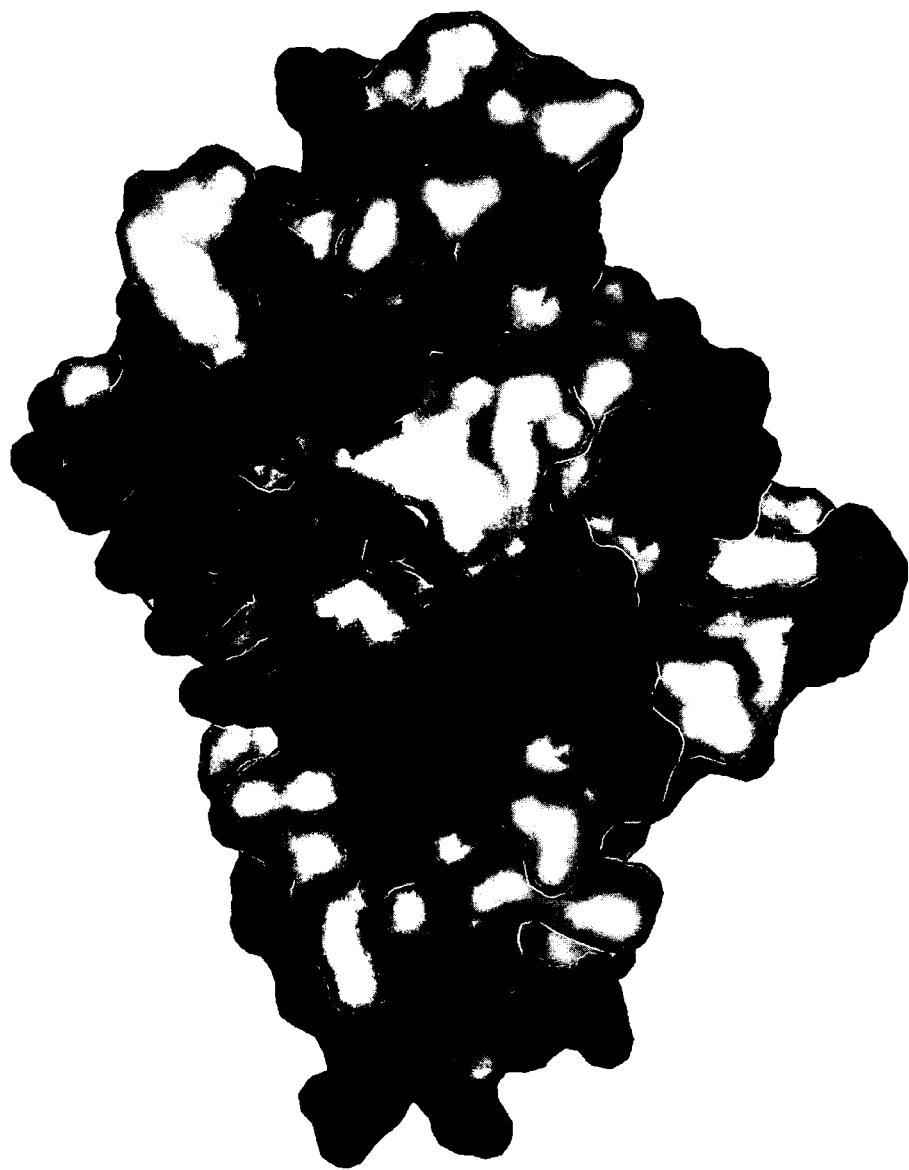
Figure 5C:
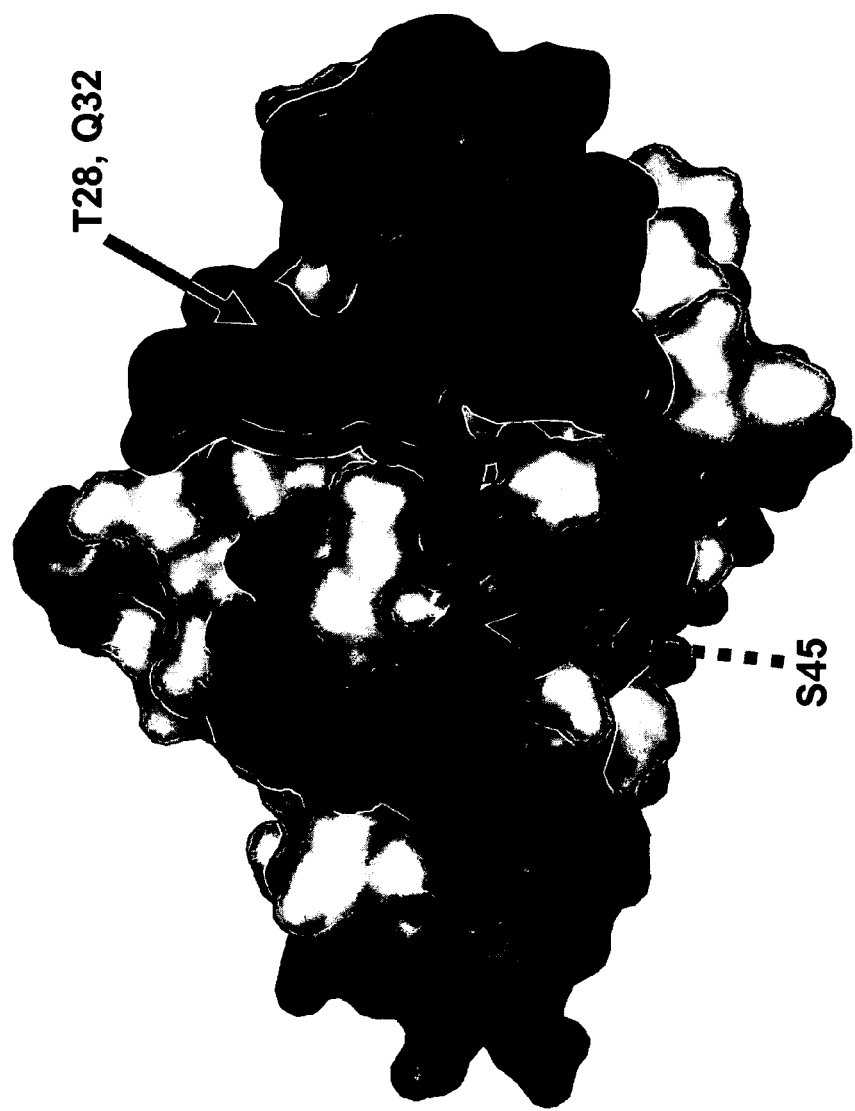
Figure 6A:
FIGS. 6A, B and C: Models of three-dimensional-structures of rMal d 1 (2620) (A), rMal d 1 (2781) (B) and rBet v 1.2801 (C). Molecular surfaces (front views) are shown. Grey surface areas show Bet v 1.2801 specific amino acid residues. White surface areas show Mal d 1 (2620) specific amino acid residues. In figure B, the six primary mutations introduced in rMal d 1 (2781) are shown in black. Figure C shows the same amino acid residues in black in Bet v 1.2801. Comparing figure A, B and C show that the six primary mutations in rMal d 1 (2781) introduce Bet v 1 specific surface structures onto one surface area on rMal d 1.
Figure 6B:
Figure 6C:
Figure 7A:
FIGS. 7A, B and C: Models of three-dimensional-structures of rMal d 1 (2620) (A), rMal d 1 (2762) (B) and rBet v 1.2801 (C). Molecular surfaces (back views) are shown. Grey surface areas show Bet v 1.2801 specific amino acid residues. White surface areas show Mal d 1 (2620) specific amino acid residues. In figure B the eight primary mutations introduced in rMal d 1 (2762) are shown in black color. Figure C shows the same amino acid residues in black in Bet v 1.2801. Comparing figure A, B and C show that the eight primary mutations in rMal d 1 (2762) introduce Bet v 1 specific surface structures onto one surface area on rMal d 1.
Figure 7B:
Figure 7C:

Despite some amino acid variation, one large surface area (see FIGS. 5A and 5B) has a high degree of structural similarity with Bet v 1 IgE. Cross-reactivity in this area is to a great extent responsible for apple induced oral allergy syndrome (OAS) in some birch pollen allergic patients. To reduce the potential of the scaffold protein rMal d 1 (2620) to trigger histamine release in birch pollen allergic patients three secondary mutations N28T, K32Q, E45S were introduced in surface areas on rMal d 1 (2620) common between birch and apple proteins (see FIG. 5C) This Mutant is named rMal d 1 (2760). Other surface areas on rMal d 1 (2620) have a very high density of Mal d 1 specific residues not found in Bet v 1 and cross-reactivity is therefore not expected to occur in these areas. To increase the potential of such surface structures to bind to Bet v 1 specific antibodies, specific amino acid residues were introduced into Mal d 1 specific surface areas on the scaffold protein. Two examples of rMal d 1 mutants that contain such primary mutations are rMal d 1 (2781) (SEQ ID NO 2) (see FIGS. 6A, B and C) and rMal d 1 (2762) (SEQ ID NO 3) (see FIGS. 7A, B and C).

Primary Mutations

In rMal d 1 (2762) and rMal d 1 (2781) introduction of 8 and 6 primary mutations, respectively, substantially increased the capacity of the mutants to bind birch pollen allergic patients serum IgE compared to rMal d 1 (2620).

Figure 8A:
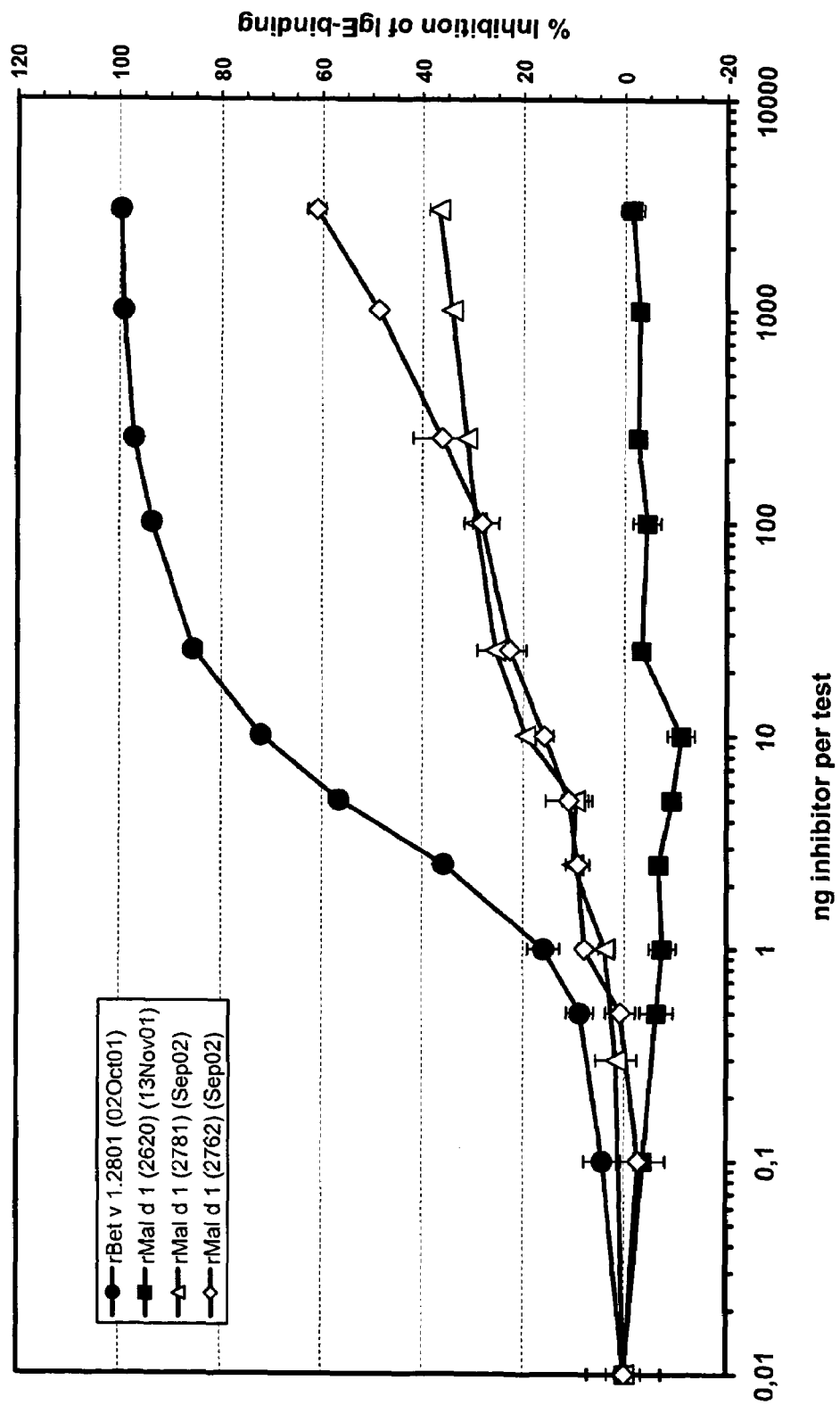
FIGS. 8A and B: A. Inhibition of the binding of biotinylated rBet v 1.2801 to pooled IgE serum from birch allergic patients by rBet v 1.2801 (●), rMal d 1 (2620) (■) or mutated rMal d 1 (2762) [◇] or (2781) [Δ] with 8 and 6 primary mutations, respectively.

This is shown in FIG. 8A where the ability of rMal d 1 (2762) and rMal d 1 (2781) to inhibit binding of serum-IgE to biotinylated rBet v 1.2801 were increased from 0% to 62% and 39%, respectively, at inhibitor concentrations of 3000 ng/test. Still, compared to rBet v 1.2801 reaching 62% and 39% IgE inhibition with the mutants, respectively, required 500-fold and 1000-fold higher antigen concentrations, respectively, showing that the rMal d 1 mutants bind IgE with considerable lower affinities than rBet v 1.2801.

Figure 8B:
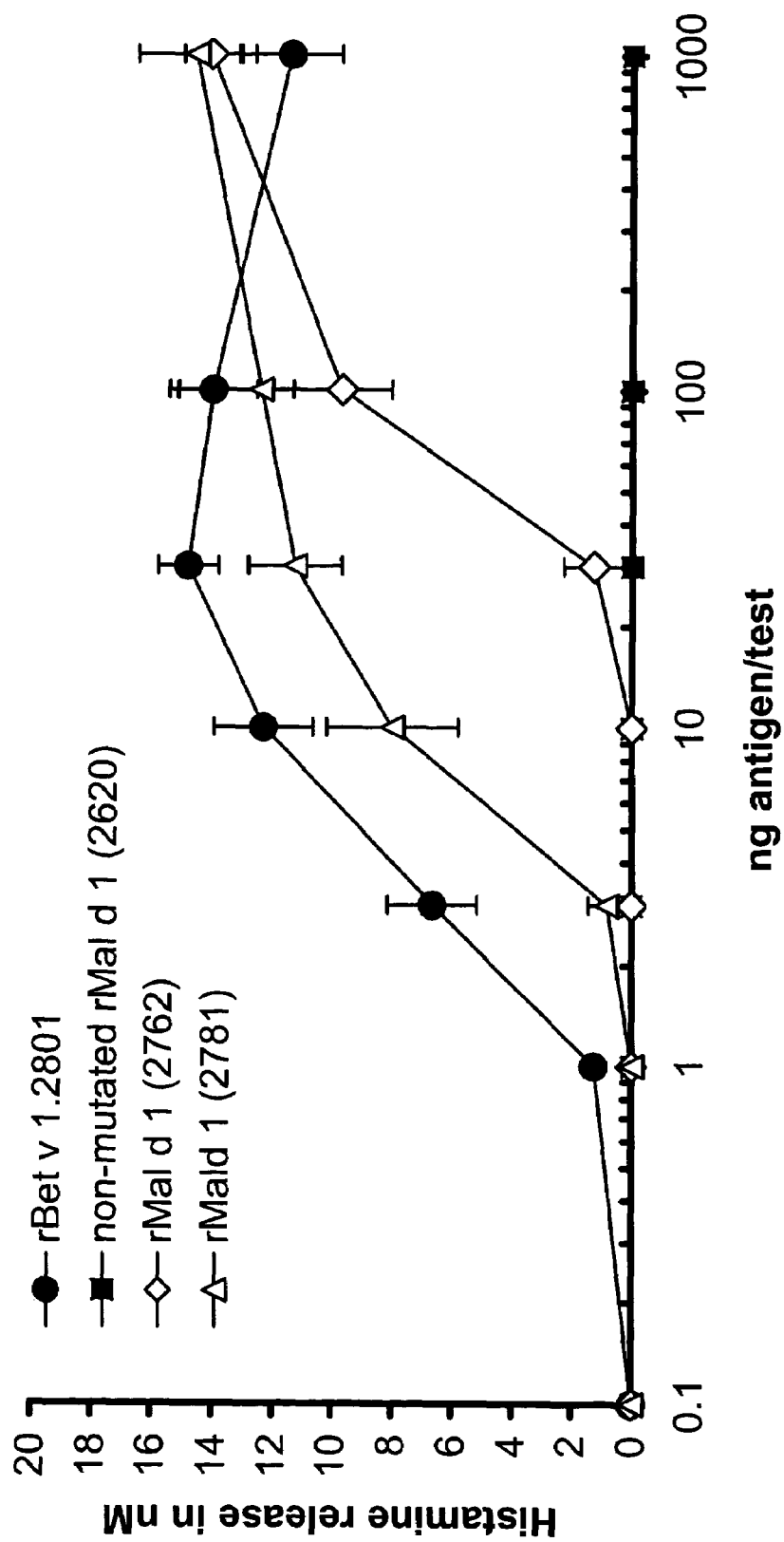

The mutated rMal d 1 molecules were further tested in human basophil histamine release assays. No histamine release occurred with non-mutated rMal d 1 (2620) in the measured antigen concentration range. rBet v 1.2801 and mutated rMal d 1 all triggered histamine release. The histamine release curves of mutated rMal d 1 (2781) and (2762) are shifted 2-fold and 20-fold, respectively, toward higher antigen concentrations compared to rBet v 1.2801 as shown in FIG. 8B.

Secondary Mutations

In FIG. 9 (right side) the scaffold protein rMal d 1 (2620) and mutated rMal d 1 (2760) inhibits binding of human serum IgE to rBet v 1.2801 from 0% to 30% in individual patients. rMal d 1 (2620) did show substantially reduced capacity to trigger histamine release compared to rBet v 1.2801 in some but not all birch pollen allergic patients basophils as shown in FIG. 9 (left side) Introduction of three secondary mutations Asn28Thr, Lys32Gln and Glu45Ser in Bet v 1 specific surface structures on the scaffold protein (rMal d 1 (2760) further reduced the capacity to trigger histamine in two birch pollen allergic patients basophils (o, p) as shown in FIG. 9 (left side). Here introduction of 3 secondary mutations abolished histamine release in the measured antigen concentration range in patient (O) and 100-fold higher concentration of rMal d 1 (2760) was required to trigger histamine release in patient (p) compared to rBet v 1.2801.

Primary and Secondary Mutations

Figure 10B:
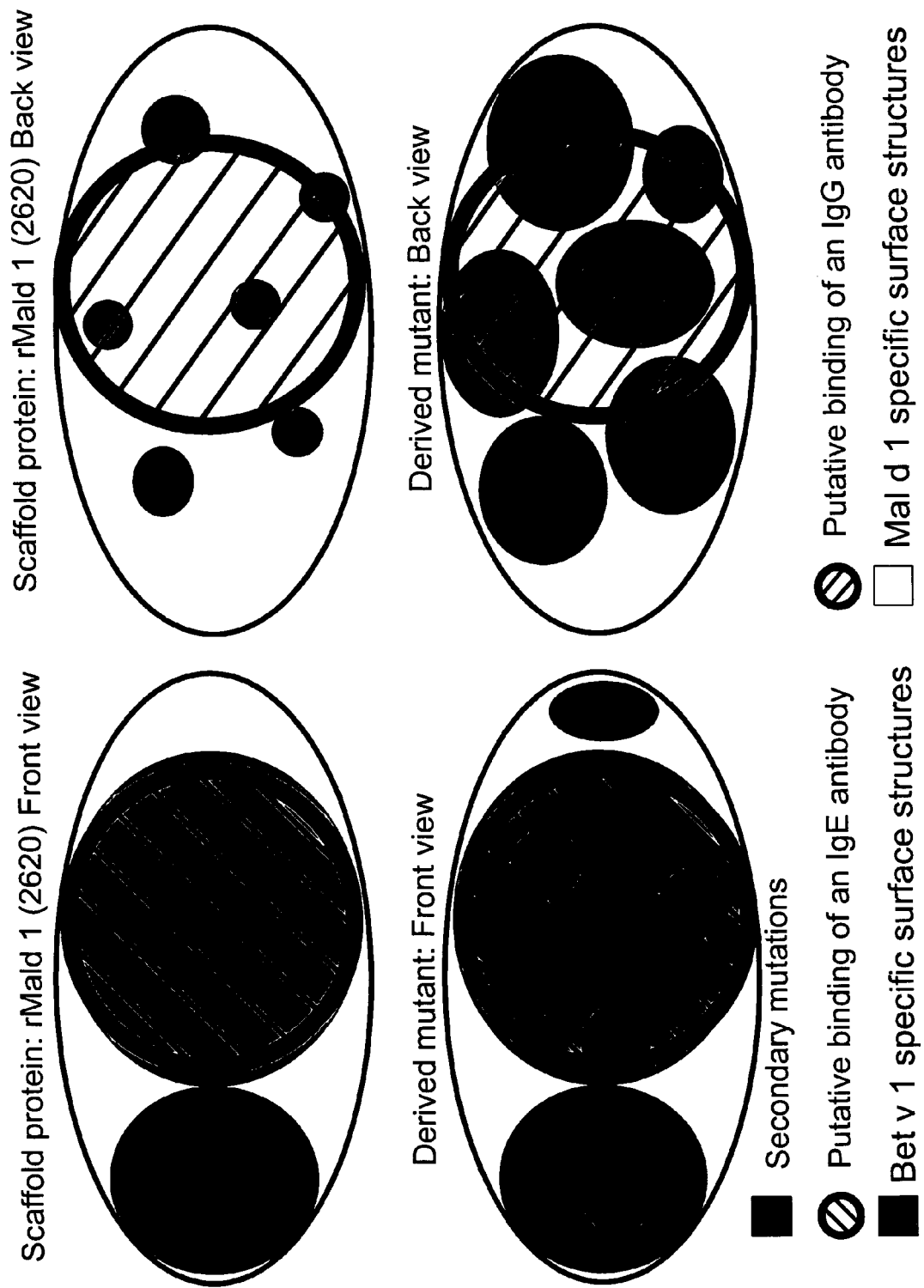

In FIGS. 10A and B a schematic illustration of a scaffold protein and a scaffold variant derived from the scaffold protein by introducing primary and secondary mutations is shown. rMal d 1 (2620) is used as a example. Front and back side of the proteins are illustrated. Scaffold (Mal d 1) specific surface structures are shown in white color. Bet v 1 and Mal d 1 common surface structures are shown in grey color. Secondary mutations are shown in black color. Top front view shows two large surface areas on the scaffold protein that binds Bet v 1 specific human serum IgE with high affinity. Bottom front view show four secondary mutations introduced in the scaffold protein in order to reduce IgE-binding affinity. Top back view shows a surface area on the scaffold protein with few common surface structures. Bottom back view shows the result of introducing primary mutations to increase the density of common surface structures where against blocking antibodies cross-reactive with natural Bet v 1 isoallergens can be directed. FIG. 10B. Top and bottom front views: A reduced fit of a putative Bet v 1 specific IgE antibody caused by introduction of 3 secondary mutations are illustrated. Top back view illustrates the generation of a blocking antibody (IgG) with poor antibody cross-reactivity to Bet v 1. Bottom back view illustrates the generation of a blocking antibody (IgG) with increased cross-reactivity to Bet v 1

T-cell Response to Recombinant wt and Mutated Mal d 1 Allergens

Changes in the amino acid sequence of an allergen can potentially provoke the elimination and/or addition of T-cell epitopes. In such cases, the modified allergens may elicit a reduced T-cell response compared to the response to the wild type allergen, and/or they will activate T-cells that recognize new epitopes. Theoretically, it is of importance to maintain the T-cell stimulation properties of the Bet v 1 hypoallergenic Mal d 1 mutants to modify the existing allergen-specific T-cell population and to support the production of blocking non-IgE antibodies. Therefore the T-cell activating properties of the rMal d 1 allergens were tested.

Two cell types were analysed in both cases cells were derived from birch allergic individuals:

1) Freshly isolated blood cells (PBL) containing polyclonal T-cells. These T-cells have the ability to respond to Bet v 1-specific epitopes and Mal d 1-specific epitopes as well as new epitopes originating from changes in the sequence. The blood cells were cultured for seven days in the presence of allergen before being subject to analysis. PBL from three individual donors was tested.

2) Allergen-specific cell lines generated by repeated stimulation with nBet v 1. These cells can be kept in culture and tested over a long period of time. T-cells are cultured with the allergen for three days. Autologous PBL cells are added as antigen presenting cells (APC). These T-cells respond primarily to original Bet v 1-specific epitopes and show the level of T-cell activation within the existing Bet v 1-specific T-cell population of the allergic patient. Four Bet v 1-specific T-cell lines were tested.

The T-cell response to the rMal d 1 allergens has been analysed by means of two assays:

1) Stimulation of T-cell proliferation, measuring the incorporation of radioactive labelled thymidin into DNA during 18 hours of culturing.

2) Stimulation of cytokine production, measured in the cell supernatant by means of CBA, a FACS-based assay that measures 6 different Th1/Th2 cytokines.

FIG. 11 shows the results from PBL stimulation assays from three individual donors, summarized in FIG. 12. In these experiments the wt Mal d 1 allergen (2620) and the triple Mal d 1 mutant (2760) do not induce any T-cell activation. The mutants 2762, in one patient, and 2781, in three out of three PBL assays performed, induced T-cell proliferation comparable to the activation induced by rBet v 1 (2801), indicating that T-cell epitopes may have been restored by the amino acid substitutions introduced in these molecules. Alternatively new epitopes may have been introduced leading to a comparable T-cell activation. As expected, all T-cell lines respond to nBet v 1.

FIG. 13 shows the T-cell proliferative response of one of the four Bet v 1-specific T-cell lines tested. This T-cell line exhibit clear cross-reactivity to the wt Mal d 1 molecule (2620), but does not recognise the mutant 2760 suggesting that the mutations introduced in this molecule disrupt a Bet v 1/Mal d 1 cross-reacting T-cell epitope recognised by this T-cell line. In contrast, the mutants 2762 and 2781 both induce proliferation.

The cytokine production in PBL cultures (FIG. 14) and in the cross-reactive T-cell line (FIG. 15) confirms the T-cell activation demonstrated in the proliferation assays. Significant changes in the cytokine production profiles were not observed when the response to Bet v 1.2801 and the Mal d 1 allergens were compared, suggesting that the difference between Bet v 1 and Mal d 1 or the changes introduced through the mutations do not lead to increased or selective Th1 activation. Induction of the inhibitory cytokine IL-10 was not observed.

In conclusion, the Mal d 1 mutants 2762 and especially 2781 seems to induce increased T-cell activation compared to the wt Mal d 1 allergen (2620) with both Bet v 1-specific T-cell lines and in freshly isolated blood cell cultures of allergic patients.

Example 2

Modification of Bet v 1 Homologous Scaffold Proteins (Surface Area I)

This example is based on modification of Dau c 1 (accession no.T14325). Amino acid residue position numbering in the following refers to T14325 as shown in FIG. 16. The example is based on the introduction of one or more of the following secondary mutations: K32X, E42X, E59X, R69X, E95X, K122X where X can be any type of amino acid residue but preferably amino acid residues that are absent in corresponding positions of known isoforms of Bet v 1. The example further includes the introduction of one or more of the following primary mutations in which residues are substituted to residues that are homologous, or more preferably, identical to corresponding amino acid residues in any known isoforms of Bet v 1. Homologous amino acid residues are: E=D, V=L=I=M, S=T, Y=F=W, K=R=H, N=Q, where (=) indicates that two or more amino acid residues are homologous. The following mutations are suggested: S12V or S12L or S12I or S12M, S14P, E16A, P105A, A107P, A148S or A148T, I151L or I151V or I151M, N153H or N153K or N153R, and elongation of the amino acid sequence with one or more of the following amino acid residues +154S or +154T, +155D or +155E, +156A, +157Y or 157F, +158N or +158Q. Protein sequences with mutated amino acid residues are shown in FIG. 16.

Modification of Bet v 1 Homologous Scaffold Proteins (Surface Area II)

This example is based on modification of Dau c 1 (accession no.T14325). Amino acid residue position numbering in the following refers to T14325 as shown in FIG. 17. The example is based on the introduction of one or more of the following secondary mutations: E8X, T10X, D25X, K32X, D46X, E59X, E95X, D108X, K122X where X can be any type of amino acid residue but preferably amino acid residues that are absent in corresponding positions of known isoforms of Bet v 1. The example further includes the introduction of one or more of the following primary mutations, in which residues are substituted to residues that are homologous, or more preferably, identical to corresponding amino acid residues in any known isoforms of Bet v 1. Homologous amino acid residues are: E=D, V=L=I=M, S=T, Y=F=W, K=R=H, N=Q, where (=) indicates that two or more amino acid residues are homologous. The following mutations are suggested: K39S or K39T, K44E or K44D, V52I or V52M or V52L, I54K or I54R or I54H, T64K or T64R or T64H, T65Y or T65F or T65W, T67K or T67R or T67H, D86E, L91G, G92D or G92E. Schematic illustration of protein sequence with mutated amino acid residues are shown in FIG. 17.

Modification of Der p 2 Homologous Scaffold Proteins (Surface Area I)

This example is based on modification of Lep d 2 (accession no. S66499). Amino acid residue position numbering in the following refers to S66499 as shown in FIG. 18. The example is based on the introduction of one or more of the following secondary mutations: K6X, S22X, R30X, K76X, K81X, V114X where X can be any amino acid residue but preferably amino acid residues that are absent in corresponding positions of known isoforms of nDer p 2 or nDer f 2 or Eur m 2. The example further includes the introduction of one or more of the following primary mutations that are homologous, or more preferably identical to corresponding amino acid residues in any known isoforms of nDer p 2 or nDer f 2 or nEur m 2. Homologous amino acid residues are: E=D, V=L=I=M, S=T, Y=F=W, K=R=H, N=Q, where (=) indicates that two or more amino acid residues are homologous. The following mutations are suggested: D17L or D17I or D17V or D17M, S19P, Q32K or Q32R or Q32H, K33P, T35Q or T35N, N88K or N88R or N88H, T92N or T92Q, A95K or A95R or A95H. Protein sequences with mutated amino acid residues are shown in FIG. 18. 3-D models of the mutants are shown in FIGS. 19A, B, C and D and in FIGS. 20A, B, C and D.

Modification of Der p 2 Homologous Scaffold Proteins (Surface Area II)

This example is based on modification of Lep d 2 (accession no. S66499). Amino acid residue position numbering in the following refers to S66499. The example is based on the introduction of one or more of the following secondary mutations: K6X, S22X, H29X, R30X, K76X, K81X where X can be any amino acid residue but preferably amino acid residues that are absent in corresponding positions of known isoforms of nDer p 2 or nDer f 2 or Eur m 2. The example further includes the introduction of one or more of the following primary mutations that are homologous more preferably identical to corresponding amino acid residues in any known isoforms of nDer p 2 or nDer f 2 or nEur m 2. Homologous amino acid residues are: E=D, V=L=I=M, S=T, Y=F=W, K=R=H, N=Q, where (=) indicates that two or more amino acid residues are homologous. The following mutations are suggested: D45N or D45Q, N47K or N47R or N47H, K48T or K48S, T50K or T50R or T50H, K52E or K52D, L54K or L54R or L54H, E107K, E107R or E107H, H112D or H112E, T119I or T119L or T119V or T119M. Protein sequences with mutated amino acid residues are shown in FIG. 18 (shown previously).

Example 3

Modification of Bet v 1 Homologous Scaffold Proteins

This example is based on modification of rMal d 1 (2620) (accession no. AJ488060). Amino acid residue position numbering in the following refers to AJ488060 as shown in FIG. 21. The example is based on the introduction of one or more of the following secondary mutations: E8X, N28X, K32X, E96X and amino acid insertion +X159 (X being any amino acid residue). In one preferable embodiment of the invention one or more of the introduced amino acid residues (X) may be amino acid residues that are homologous to Bet v 1 specific residues for each of the individually corresponding positions. Homologous amino acid residues are: E=D, V=L=I=M, S=T, Y=F=W, K=R=H, N=Q, where (=) indicates that two or more amino acid residues are homologous. The following mutations are suggested: E8D, N28Q, K32R or K32H, E96D. The example further includes the introduction of one or more of the following primary mutations where introduced mutations are residues that are identical or homologous to corresponding amino acid residues in any known isoforms of Bet v 1. The following mutations are suggested: E12V or E12I or E12M or E12L, H40S or H40T, E76H or E76R or E76K, E129A, P154S or P154T. Protein sequences with mutated amino acid residues are shown in FIG. 21.

Modification of Der p 2 Homologous Scaffold Proteins

This example is based on modification of Gly d 2 (accession no. AJ272216). Amino acid residue position numbering in the following refers to AJ272216 as shown in FIG. 22. The example is based on the introduction of one or more of the following secondary mutations: K6X, R30X, F74X, K81X, K88X, T90X, V114X (X being any amino acid residue).

In one preferable embodiment of the invention one or more of the introduced amino acid residues (X) may be amino acid residues that are homologous to Der p 2 or Der f 2 or Eur m 2 specific residues for each of the individually corresponding positions. Homologous amino acid residues are: E=D, V=L=I=M, S=T, Y=F=W, K=R=H, N=Q, where (=) indicates that two or more amino acid residues are homologous. The following mutations are suggested: K6R or K6H, R30K or R30H, F74Y or F74W, K81R or K81H, K88R or K88H, T91S, V114L or V114I or V114M. The example further includes the introduction of one or more of the following primary mutations that are identical or homologous to corresponding amino acid residues in any known isoforms of Der p 2 or Der f 2 or Eur m 2.

The following mutations are suggested: K2Q or K2N, K4D or K4E, K10N or K10Q, T14K OR T14R, S22H or S22R or S22K, K39V or K39L or K39I or K39M, D45N or D45Q, T60L or T60V or T60I or T60M, Q63D, or Q63E, K80V or K80L or K80I or K80M, H112D or H112E, R122I or R122V or R122L or R122M. Protein sequences with mutated amino acid residues are shown in FIG. 22. 3-D models of the mutants are shown in FIGS. 23A, B, C and D and in FIGS. 24A, B, C and D.

Example 4

Comparison of Secondary Structure Elements in Homogeneous Preparations of Homogeneously Folded Proteins by CD Spectroscopy or an Experimental Approach to Determine if the Three Dimensional Structures of Two Proteins Share Significant Homologies:

Visual comparison of CD spectra determined for different or homologous proteins may be performed by an expert in the field. If the spectra seem to be reasonably superimposable one may assume that the proteins probably belong to the same structural class and a deconvolution process may confirm this classification.

CD spectra recorded in the wavelength range 260 nm to at least 184 nm were deconvoluted by the program CDNN.

The deconvolution was performed as follows:

CD data (as a comma delimited txt file (nm;mDeg)) were loaded into the software and appropriate parameters were provided (Mw, concentration (mg/ml), number of amino acids) and the spectra was deconvoluted using a training base spectra set of 33.

The concentration of the protein was adjusted to a value giving a total of secondary structure elements of 100%±1% (185-260 nm).

The secondary structure elements were transformed into three values Helix, "Sheet"=anti-parallel+parallel and Turn+coil=Beta-turn+random coil. The proteins were considered to be structurally similar if their deconvolution set (Helix, Sheet, Turn+coil) were within the values of the deconvolution set determined for the reference protein ±20%.

According to FIG. 25, the deconvolution sets of rMal d 1 (2762), rMal d 1 (2781) and Bet v 1.2801 fall within the acceptance boundaries determined for the reference protein, rMal d 1 (2620) (±15%), and therefore these proteins may be considered to be structurally (secondary structure) similar.

Example 5

Antibody Reactivity of Bet v 1 and Mutated Mal d 1:

The kinetic parameters for the interactions between a monoclonal mouse IgG antibody (BV16) raised against nBet v 1 and two allergens rBet v 1.2801 and modified rMal d 1 (2781), respectively, were measured by surface plasmon resonance (SPR).

Recombinant proteins were prepared as described in example 1. The Biacore experiments were set up according to the manufactures recommendations (Biacore® 2000 Instrument Handbook, January 2001; Getting started Biacore® 3000, October, 1998). In brief, the monoclonal Monoclonal antibody BV16 (ALK, Hørsholm, Denmark) (1 to 10 µg/ml in HBS-EP biacore buffer) was injected into the four flow-channels on the Biacore Sensor Chip CAA5 for 300 sec at a flow rate of 30 µL/min (charging phase), followed by a 150 sec flow (30 µL/min) of HBS-EP buffer (equilibrium phase). The antigen, i.e. rBet v 1.2801, rMal d 1 (2620) or mutated rMal d 1 (2781), was injected for 180 sec (association phase), followed by a HBS-EP buffer flow (30 µ/L/min) for up to 1000 sec (dissociation phase), and the flow-channels were regenerated by a pulse of 10 mM glycine solution, pH 1.8 for 30 sec at a flow rate of 30 µL/min. The data used to estimate k1 (M−1·s−1), k−1 (s−1) and Kd (M) values were obtained from experiments performed with 5 different antigen concentrations (1 to 150 µg/mL).

The results from the Biacore experiments are graphically shown in FIG. 26. The kinetic parameters are shown in table 1.

TABLE 1

| Complexes | $k_1 \pm S.E.$ $M^{-1}s^{-1}$ | $k_{-1} \pm S.E.$ $s^{-1}$ | $\sim K_d \pm S.E.M$ |
|---|---|---|---|
| BV16 rBetv 1.2801 | $(1.0 \pm 0.1) * 10^5$ | $(2.5 \pm 1.4) * 10^{-5}$ | $=(2.4 \pm 1.4) * 10^{-10}$ |
| BV16 rMal d 1 (2781) | $(1.2 \pm 0.1) * 10^5$ | $(3.2 \pm 0.3) * 10^5$ | $=(2.7 \pm 0.4) * 10^{-10}$ |

Table 1: Kinetic parameters for the interactions between the monoclonal antibody BV16 and the two allergens, rBet v 1.2801 and mutated rMal d 1 (2781). The kinetic parameters were calculated based on several measurements at different antigen concentrations and time periods up to 1000 seconds.

The Kd values obtained for the two antibody/allergen complexes were virtually identical. This strongly indicates that the proteins have very similar α-carbon backbone folding patterns. Furthermore, the epitope recognized by BV16 antibodies includes amino acid residues located in several of the strands in the anti-parallel β-sheet present in the crystallographic structure of rBet v 1.2801 (pdb entry 1bv1). In conclusion, not only has an essentially complete and functional epitope been grafted from rBet v 1 to rMal d 1. Also, the virtually identical Kd values suggest that the complete structural BV16 epitope has been introduced onto the surface of Mal d 1.

The invention claimed is:

1. A recombinant protein variant (rMal d 1 (2781)), comprising the sequence defined in SEQ ID NO: 2 with the ability to induce a protective immune response to a naturally occurring allergen, wherein the naturally occurring allergen is Bet v 1.

2. A recombinant protein variant (rMal d 1 (2762)) comprising the sequence as defined in SEQ ID NO: 3, with the ability to induce a protective immune response to a naturally occurring allergen, wherein the naturally occurring allergen is Bet v 1.

3. A recombinant protein variant with the ability to induce a protective immune response to a naturally occurring allergen, wherein the naturally occurring allergen is Bet v 1, wherein the protein variant is a variant of a scaffold protein Dau c 1 comprising the sequence as defined in SEQ ID NO: 4, said variant consisting of at least two primary mutations that are selected from the group consisting of: (S12V, S12L, S12I, S12M), S14P, E16A, P105A, A107P, (A148S, A148T), (I151L, I151V, I151M), (N153H, N153K, N153R), (+154S, +154T), (+155D, +155E), +156A, (+157Y, +157F), (+158N, +158Q), (K39S, K39T), (K44E, K44D), (V52I, V52M, V52L), (I54K, I54R, I54H), (T64K, T64R, T64H), (T65Y, T65F, T65W), (T67K, T67R, T67H), D86E, L91G, (G92D, G92E) and optionally one or more secondary mutations are selected from the group consisting of: K32X, E42X, E59X, R69X, E95X, K122X, E8X, T10X, D25X, D64X, and D108X.

4. A protein variant according to claim 3 wherein the Dau c 1 scaffold protein is Accession No. T14325 comprising the sequence as defined in SEQ ID NO:4 and comprises at least two primary mutations selected from the group consisting of: (S12V, S12L, S12I, S12M), S14P, E16A, P105A, A107P, (A148S, A148T), (I151L, I151V, I151M), (N153H, N153K, N153R), (+154S, +154T), (+155D, +155E), +156A, (+157Y, +157F), (+158N, +158Q) and optionally one or more secondary mutations selected from the groups consisting of: K32X, E42X, E59X, R69X, E95X, and K122X.

5. A protein variant according to claim 3 wherein the Dau c 1 scaffold protein is Accession No. T14325 comprising the sequence as defined in SEQ ID NO:4 and comprises at least two primary mutations selected from the group consisting of: (K39S, K39T), (K44E, K44D), (V52I, V52M, V52L), (I54K, I54R, I54H), (T64K, T64R, T64H), (T65Y, T65F, T65W), (T67K, T67R, T67H), D86E, L91G, (G92D, G92E) and optionally at least one secondary mutation is selected from the group consisting of: E8X, T10X, D25X, K32X, D46X, E59X, E95X, D108X, and K122X.

* * * * *